United States Patent [19]
Lee et al.

[11] Patent Number: 5,955,366
[45] Date of Patent: Sep. 21, 1999

[54] POLYNUCLEOTIDES ENCODING CYTOKINE SUPPRESSIVE ANTI-INFLAMMATORY DRUG BINDING PROTEINS

[75] Inventors: John C. Lee, Radnor; Jerry L. Adams, Wayne; Timothy F. Gallagher, Harleysville; David W. Green, Bryn Mawr; John Richard Heys, Malvern; Peter C. McDonnell, Fort Washington; Dean E. McNulty, Philadelphia, all of Pa.; James E. Strickler, Milton, Mass.; Peter R. Young, Lawrenceville, N.J.

[73] Assignee: SmithKline Beecham Corporation, Philadelphia, Pa.

[21] Appl. No.: 08/950,449

[22] Filed: Oct. 14, 1997

Related U.S. Application Data

[63] Continuation of application No. 08/250,975, May 31, 1994, Pat. No. 5,783,664, which is a continuation-in-part of application No. 08/123,175, Sep. 17, 1993, abandoned.

[51] Int. Cl.$^6$ .............................. C12N 15/12; C12N 5/10; C12N 1/11; C12N 1/20
[52] U.S. Cl. ...................... 435/471; 435/455; 435/476; 435/320.1; 435/325; 435/252.3; 536/23.1; 536/23.5
[58] Field of Search .................................. 435/471, 455, 435/476, 320.1, 325, 252.3; 536/23.1, 23.5

[56] References Cited

U.S. PATENT DOCUMENTS

| | | | |
|---|---|---|---|
| 4,778,806 | 10/1988 | Bender et al. | 514/336 |
| 4,780,470 | 10/1988 | Bender et al. | 514/341 |
| 4,794,114 | 12/1988 | Bender et al. | 514/333 |
| 5,317,019 | 5/1994 | Bender et al. | 514/224.2 |
| 5,512,473 | 4/1996 | Brent et al. | 435/252.33 |

OTHER PUBLICATIONS

Payne, et al., 1991, *EMBO J. 10*: 885–892.
Boulton, et al., 1991, *Cell 65*: 663–675.
Lee, et al., 1989, *Agents and Actions 27*: 277–279.
Lee, et al., 1990, *Int. J. Immunother. 6*: 1–12.
Griswold, et al., 1993, *Drugs Exptl. Clin. Res. 19*: 243–248.
Han, et al., 1995, *Biochimia et Biophysica Acta 1265*: 224–227.
Rouse, et al., 1994, *Cell 78*: 1027–37.
Cuenda, et al., *FEBS Letters*, 364: pp. 229–233 (1995).
Lee, et al., *Nature*, 372: 22/29, pp. 739–746 (1994).
Lee, et al., 1988, *Int. J. Immunopharmac.*, 10: 835–843.

*Primary Examiner*—Elizabeth Kemmerer
*Attorney, Agent, or Firm*—William T. King; Elizabeth J. Hecht

[57] ABSTRACT

This invention relates to drug binding proteins, to genes encoding same and to assays and methods for screening pharmaceuticals. More specifically, this invention relates to a Cytokine Suppressive Anti-Inflammatory Drug (CSAID) binding protein, to a gene encoding same and to assays and screens useful in the evaluation and characterization of drugs of this pharmacologic class.

25 Claims, 26 Drawing Sheets

VALUES ARE IC$_{50}$, μM

| COMPOUND | R1/R2 | X-Y | IL-1 | TNF | THP-1 CYTOSOL BINDING |
|---|---|---|---|---|---|
| XI(a) | 4-pyridyl/4-FPh | -CH2CH2S- | 0.5 | 0.4 | <0.1 |
| XI(b) | 4-FPh/4-pyridyl | -CH2CH2S- | >5 | >5 | 10 |
| XI(c) | 4-pyridyl/4-FPh | -CH2CH2CH2- | 0.2 | 0.2 | <0.1 |
| XI(d) | 4-FPh/4-pyridyl | -CH2CH2CH2- | >5 | >5 | >10 |
| XI(e) | 4-pyridyl/4-MeSPh | -CH2CH2CH2- | 2.7 | 2.7 | 3.4 |
| XI(f) | 4-MeSPh/4-pyridyl | -CH2CH2CH2- | >5 | >5 | 5 |
| XI(g) | 4-pyridyl/4-FPh | -CH2CH2OAC,H | 0.5 | 3 | 0.5 |
| XI(h) | 4-FPh/4-pyridyl | -CH2CH2OAC,H | 5 | 5 | >10 |

```
  1  AACATTGTGAAATGTCAGAAGCTTACAGAATGACCATGTTCAGTTCCTTATCTACCAAATT   60
     AsnIleValLysCysGlnLysLeuThrAspHisValGlnPheLeuIleTyrGlnIle

61  CTCCGAGGTCTAAAGTATATACATTCAGCTGACATAATTCACAGGACCTAAAACCTAGT  120
     LeuArgGlyLeuLysTyrIleHisSerAlaAspIleIleHisArgAspLeuLysProSer

121  AATCTAGCTGTGAATGAAGACTGTGAGCTGGAAGATTCTGGATTTTGGACTGGCTCGGCAC  180
     AsnLeuAlaValAsnGluAspCysGluLeuLysIleLeuAspPheGlyLeuAlaArgHis

181  ACAGATGATGAAATGACAGGCTACGTGGCCACTAGGTGGTACAGGCTCCTGAGATCATG  240
     ThrAspAspGluMetThrGlyTyrValAlaThrArgTrpTyrArgAlaProGluIleMet

241  CTGAACTGGATGCATTACAACCAGACAGGTGGTATTTGGGTCAAG                285
     LeuAsnTrpMetHisTyrAsnGlnThrGlyGlyIleTrpValLys
```

FIG.13

CAAGTCCCAATCCTCCCCAACCACAGCAAGTTGAATTTATCAACCATGTTGGGTTGTAAA

TGCTCGTGTGATTTCCTACAAGAAATACCTGCTCTGAATATTTTTGTAATAAAGGTCTTT

GCACATGTGACCCACAATACGTGTTAGGAGCCTGCATGCTCTGGAAGCCTGGACTCTAAG

CTGGAGCTCTTGGAAGAGCTCTTCGGTTTCTGAGCATAATGCTCCCATCTCCTGATTTCT

CTGAACAGAAAACAAAAGAGAGAATGAGGGAAATTGCTATTTTATTTGTATTCATGAACT

TGGCTGTAATCAGTTATGCCGTATAGGATGTCAGACAATACCACTGGTTAAAATAAAGCC

TATTTTTCAAATTTAAAAAAAAAAAAAAAAAA

FIG.14

```
..355nts..GCCGCTGGAAAATGTCTCAGGAGAGGCCCACGTTCTACCGGCAGGAGCTGAACAAGACAATCTGG    420
                   M  S  Q  E  R  P  T  F  Y  R  Q  E  L  N  K  T  I  W      18

GAGGTGCCCGAGCGTTACCAGAACCTGTCTCCAGTGGGCTCTGGCGCCTATGGGTCTGTGTGTGCTTTTGAC    495
 E  V  P  E  R  Y  Q  N  L  S  P  V  G  S  G  A  Y  G  S  V  C  A  A  F  D   43

ACAAAACGGGGTTACGTGTGGCAGTGAAGAAGCTCTCCAGACCATTCATTCAGTCCGAAAAGAACC          570
 T  K  R  G  L  R  V  A  V  K  K  L  S  R  P  F  Q  S  I  H  A  K  R  T      68

TACAGAGAACTGCGGGTTACTTAAACTTAAAACATATGAAAACATGAAAATGTGATTGGTCTGTTGGACGTTTTACACCTGCA   645
 Y  R  E  L  R  L  L  K  H  M  K  H  E  N  V  I  G  L  L  D  V  F  T  P  A   93

AGGTCTCTGGAGGAATTCAATGATGTGTATCTGGTGACCCATCTGATGGGGCAGATCTGAACAACATTGTGAAA           720
 R  S  L  E  E  F  N  D  V  Y  L  V  T  H  L  M  G  A  D  L  N  N  I  V  K   118

TGTCAGAAGCTTACAGATGACCATGTTCAGTTCCTTATCTTACCAAATTCTCCGAGGTCTAAAGTATATACATTCA         795
 C  Q  K  L  T  D  D  H  V  Q  F  L  I  Y  Q  I  L  R  G  L  K  Y  I  H  S   143

GCTGACATAATTCACAGGGACCTAAAACCTAGTAATCTAGCTGTGAATGAAGATTGTGAGCTGAAGATTCTGGAT          870
 A  D  I  I  H  R  D  L  K  P  S  N  L  A  V  N  E  D  C  E  L  K  I  L  D   168

TTTGGACTGGCTCGGCACACAGATGATGAAATGACAGGCTACGTGGCCACTAGGTGGTACAGGGCTCCTGAGATC          945
 F  G  L  A  R  H  T  D  D  E  M  T  G  Y  V  A  T  R  W  Y  R  A  P  E  I   193
```

FIG. 16A

```
ATGCTGAACTGGATGCATTACAACCAGACAGTTGATATTTGGTCAGTGGGATGCATAATGGCCGAGCTGTTGACT      1020
 M  L  N  W  M  H  Y  N  Q  T  V  D  I  W  S  V  G  C  I  M  A  E  L  L  T        218

GGAAGAACATTGTTCCTGGTACAGACCATATTAACCAGCTTCAGCAGATTATGCGTCTGACAGGAACACCCCCC      1095
 G  R  T  L  F  P  G  T  D  H  I  N  Q  L  Q  Q  I  M  R  L  T  G  T  P  P       243

GCTTATCTCATTAACAGGATGCCAAGCCATGAGGCAAGAAACTATATTCAGTCTTTGACTCAGATGCCGAAGATG      1170
 A  Y  L  I  N  R  M  P  S  H  E  A  R  N  Y  I  Q  S  L  T  Q  M  P  K  M       268

AACTTTGCGAATGTATTTATTGGTGCCAATCCCCTGGCTGTGGACTTGCTGGAGAAGATGCTTGTATTGGACTCA      1245
 N  F  A  N  V  F  I  G  A  N  P  L  A  V  D  L  L  E  K  M  L  V  L  D  S       293

GATAAGAGAATTACAGCGGCCCAAGCCCTTGCACATGCCTACTTTGCTCAGTACCACGATCCTGATGATGAACCA      1320
 D  K  R  I  T  A  A  Q  A  L  A  H  A  Y  F  A  Q  Y  H  D  P  D  D  E  P       318

GTGGCCGATCCTTATGATCAGTCCTTTGAAAGCAGGGACCTCCTTATAGATGAGTGGAAAAGCCTGACCTATGAT      1395
 V  A  D  P  Y  D  Q  S  F  E  S  R  D  L  L  I  D  E  W  K  S  L  T  Y  D       343

GAAGTCATCAGCTTTGTGCCACACCCCTTGACCAAGAAGAGAGATGGAGTCCTGAGCACCT...2330nts..
 E  V  I  S  F  V  P  H  P  L  T  K  K  R  D  G  V  L  S  T  *
```

FIG. 16B

```
                                                                                                    1128
                                                                                                     255
AACCAGCTTCAGCAGATTATGCGTCTGACAGGAACACCCCCGCTTATCTCATTAACAGGATGCCAAGCCATGAG
 N  Q  L  Q  Q  I  M  R  L  T  G  T  P  P  A  Y  L  I  N  R  M  P  S  H  E

D  Q  L  K  L  I  L  R  L  V  G  T  P  G  A  E  L  L  K  K  I  S  S  E  S
GATCAGTTGAAGCTCATTTTAAGACTCGTTGGAACTCCAGGGGCTGAGCTTTTGAAGAAAATCTCCTCAGAGTCT
                                                                                                     255
                                                                                                    1128
```

FIG.17

```
                 1                                                            50
Human Erk1    MAAAAAQGGG GGEPRRTEGV GPGVPGEVEM VKGQ....PF DVGPRYTQLQ
Human Erk2    MAAAAAAGAG P..........  ........EM VRGQ....VF DVGPRYTNLS
       Csbp   .......... .......... ..MSQERPTF YRQELNKTIW EVPERYQNLS
 Yeast Hog1   .......... .......... ...MTTNEEF IRTQIFGTVF EITNRYNDLN
    Identity .......... .......... .......... .......... ....RY..L.

51      I                    II                  III    100
Human Erk1    YIGEGAYGMV SSAYDHVRKT RVAIKKIS.P FEHQTYCQRT LREIQILLRF
Human Erk2    YIGEGAYGMV CSAYDNVNKV RVAIKKIS.P FEHQTYCQRT LREIKILLRF
       Csbp   PVGSGAYGSV CAAFDTKTGL RVAVKKLSRP FQSIIHAKRT YRELRLLKHM
 Yeast Hog1   PVGMGAFGLV CSATDTLTSQ PVAIKKIMKP ESTAVLAKRT YRELKLLKHL
    Identity ..G.GA.G.V ..A.D..... .VA.KK...P F.......RT .RE...L...

101    IV                   V                          150
Human Erk1    RHENVIGIRD IL.RASTLEA MRDVYIVQDL METDLYKLLK SQQLSNDHIC
Human Erk2    RHENIIGIND II.RAPTIEQ MKDVYIVQDL METDLYKLLK TQHLSNDHIC
       Csbp   KHENVIGLLD VFTPARSLEE FNDVYLVTHL MGADLNNIVK CQKLTDDHVQ
 Yeast Hog1   RHENLICLQD IF.....LSP LEDIYFVTEL QGTDLHRLLQ TRPLEKQFVQ
    Identity .HEN.I...D .......... ..D.Y.V..L ...DL..... ...L......

151       VI                                    VII    200
Human Erk1    YFLYQILRGL KYIHSANVLH RDLKPSNLLI NTTCDLKICD FGLARIADPE
Human Erk2    YFLYQILRGL KYIHSANVLH RDLKPSNLLL NTTCDLKICD FGLARVADPD
       Csbp   FLIYQILRGL KYIHSADIIH RDLKPSNLAV NEDCELKILD FGLARHTDDE
 Yeast Hog1   YFLYQILRGL KYVHSAGVIH RDLKPSNILI NENCDLKICD FGLARIQDPQ
    Identity ...YQILRGL KY.HSA...H RDLKPSN... N..C.LKI.D FGLAR..D..

201     *  *    VIII                   IX              250
Human Erk1    HDHTGFLTEY VATRWYRAPE IMLNSKGYTK SIDIWSVGCI LAEMLSNRPI
Human Erk2    HDHTGFLTEY VATRWYRAPE IMLNSKGYTK SIDIWSVGCI LAEMLSNRPI
       Csbp   ......MTGY VATRWYRAPE IMLNWMHYNQ TVDIWSVGCI MAELLTGRTL
 Yeast Hog1   ......MTGY VSTRYYRAPE IMLTWQKYDV EVDIWSAGCI FAEMIEGKPL
    Identity .......T.. V.TR.YRAPE IML....Y.. ..DIWS.GCI .AE.......

251                 X                                  300
Human Erk1    FPGKHYLDQL NHILGILGSP SQEDLNCIIN MKARNYLQSL PSKTKVAWAK
Human Erk2    FPGKHYLDQL NHILGILGSP SQEDLNCIIN LKARNYLLSL PHKNKVPWNR
       Csbp   FPGTDHINQL QQIMRLTGTP PAYLINRMPS HEARNYIQSL TQMPKMNFAN
      Csbp2   -------DQL KLILRLVGTP GAELLKKISS ES-----.-- ----------
 Yeast Hog1 · FPGKDHVHQF SIITDLLGSP PKDVINTICS ENTLKFVTSL PHRDPIPFSE
    Identify FPG.....Q. ..I....G.P .......... .........SL ..........

301          XI                                        350
Human Erk1    LFPKSDSKAL DLLDRMLTFN PNKRITVEEA LAHPYLEQYY DPTDEPVAEE
Human Erk2    LFPNADSKAL DLLDKMLTFN PHKRIEVEQA LAHPYLEQYY DPSDEPIAEA
       Csbp   VEIGANPLAV DLLEKMLVLD SDKRITAAQA LAHAYFAQYH DPDDEPVADP
 Yeast Hog1   RFKTVEPDAV DLLEKMLVFD PKKRITAADA LAHPYSAPYH DPTDEPVADA
    Identity .F......A. DLL..ML... ..KRI....A LAH.Y...Y. DP.DEP.A..

351                                                    400
Human Erk1    PFTFAMELDD LPKERLKELI FQETARFQPG VLEAP..... ..........
Human Erk2    PFKFDMELDD LPKEKLKELI FEETARFQPG YRS....... ..........
       Csbp   .YDQSFESRD LIDEWKSLT YDEVISFVPP PLDQEEMES. ..........
 Yeast Hog1   KFDWHFNDAD LPVDTWRVMM YSEILDFHKI GGSDGQIDIS ATFDDQVAAA
    Identity .........D L......... ....E...F... .......... ..........
```

```
  1  GGAACCGCGACCACTGGAGCCTTAGCGGGGCCAGCTGGAACGGAGTACTGCGACCAGCCCGAGTCGCC

76  TTGTAGGGGCGAAGGTGCAGGGAGATCGCGGGGAGTCTTGAGCGCGTCCCTGCCCTTAGCGG

151  GGCTTGCCCCAGTCGCAGGGCACATCCAGCCGCTGACAGCCGCTGGGCGGGAGTCTGCGGGTC

226  GCGGCAGCCGCACCTGCGGGCGACCAGCGGCAAGTCCCCGCGGGCGGGGCAGCAAGGCGCGGGAGAG

301  GGTGCGGGTGCAGGGGCCCCACAGGCCCACCTTCTGCCCGGGCGTGCCCGCTGAAAATGTCTCAGGAGA
-19                                                                MetSerGlnGluA

376  GGCCCACGTTCTACCGGCAGGAGCTGAACAAGACAATCTGGGAGGTGCCCGAGCGTTACCAGAACCTGTCTCCAG
  6  rgProThrPheTyrArgGlnGluLeuAsnLysThrIleTrpGluValProGluArgTyrGlnAsnLeuSerProV

451  TGGGCTCTGGCGCCTATGGCTCTGTCGTCTTTGACACAAAAACGGGGTTACGGTGCAGTGAAGAAGC
 31  alGlySerGlyAlaTyrGlySerValCysAlaAlaPheAspThrLysThrGlyLeuArgValAlaValLysL

526  TCTCCAGACCATTCAGTCGATCCATCATTCATGCGAAAAGAACCTACAGAGAACTGCGTTACTTAAACATATGAAAC
 56  euSerArgProPheGlnSerIleIleHisAlaLysArgThrTyrArgGluLeuArgLeuLeuLysHisMetLysH
```

601 ATGAAAATGTGATTGGTCTGTTGGACGTTTTTACACCTGCAAGTCTCTGGAGGAATTCAATGATGTGTATCTGG
81  isGluAsnValIleGlyLeuLeuAspValPheThrProAlaArgSerLeuGluPheAsnAspValTyrLeuV

676 TGACCCATCTCATGGGGCAGATCTGAACAACATTGTGAAATGTCAGAGAAGCTTACAGATGACCATGTTCAGTTCC
106 alThrHisLeuMetGlyAlaAspLeuAsnAsnIleValLysCysGlnLysLeuThrAspHisValGlnPheL

751 TTATCTACCAAATTCTCCGAGGTCTAAAGTATATACATTCAGCTGACATAATTCAGGACCTAAAACCTAGTA
131 euIleTyrGlnIleLeuArgGlyLeuLeuLysTyrIleHisSerAlaAspIleIleHisArgAspLeuLysProSerA

826 ATCTAGCTGTGAATGAAGACTGTGAGCTGAAGATTCTGATTTTGACTCTGGACTCGGCACACAGATGATGAAATGA
156 snLeuAlaValAlaAsnGluAspCysGluLeuLysIleLeuLeuAspPheGlyLeuAlaArgHisThrAspAspGluMetT

901 CAGGCTACGTGGCCACTAGTGGTACAGGGCTCCTGAGATCATCGTGAACTGATCATTACAACCAGACAGTTG
181 hrGlyTyrValAlaThrArgTrpTyrArgAlaProGluIleMetLeuAsnTrpMetHisTyrAsnGlnThrValA

976 ATATTTGGTCAGTGGGATGCATAATGCCCGAGCTGTTGACTCTGTTGGAAGAACATTGTTCCTGTACAGACCATATTA
206 spIleTrpSerValGlyCysIleMetAlaGluLeuLeuThrGlyArgThrLeuPheProGlyThrAspHisIleA

1051 AccagcttcagcagcagattatgcgtctgacaggatgccaagcatgagG
231  snGlnLeuGlnIleMetArgLeuThrGlyThrProProAlaTyrLeuIleAsnArgMetProSerHisGluA 1126 CAAGAAACTATATTCAGTCTTTGACTCTCAGATGCCAAGATGAACTTTGCAATGTATTATTGGTGCCAATCCCC
256  laArgAsnTyrIleGlnSerLeuThrGlnMetProLysMetAsnPheAlaAsnValPheIleGlyAlaAsnProL

FIG. 2IB

```
1201  TGGCTGTCGACTTGCTGCTGGAGAAGATGCTTGTATTGGACTCAGATAAGAGAATTACAGGGGCCCAAGCCCTTGCAC
281   euAlaValAspLeuLeuLeuGluLeuLysMetLeuValLeuAspSerAspLysArgIleThrAlaAlaGlnAlaLeuAlaH

1276  ATGCCTACTTTGCTCAGTACCACGATCCTGATGATGAACCAGTGGCCGATCCTTATGATCAGTCCTTTGAAAGCA
306   isAlaTyrPheAlaGlnTyrHisAspProAspAspGluProValAlaAspProTyrAspGlnSerPheGluSerA

1351  GGGACCTCCTTATAGATGAGTGGAAAAGCCTGACCTATGAAGTCATCAGCTTTGTGCCACCACCCCTGACC
331   rgAspLeuLeuIleAspGluTrpLysSerLeuThrTyrAspGluValIleSerPheValProProLeuAspG

1426  AAGAAGAGATGGAGTCCTGAGCACCTGGTTCTGTTCTGTGATCCCACTTCACTGTGAGGGAAGGCCTTTCA
356   lnGluGluMetGluSerEnd

1501  CGGGAACTCTCCAAATATTATTCAAGTGCCCTCTTGTTGCAGAGATTTCCTCCATGGTGAAGGGGTGTGCCGTGC

1576  GTGTGCGTGCGTGTAGTGTGTGTGCATGTGTGTGTCTTGTGTGGGAGGTAAGACAATATGAACAAACTAT

1651  GATCACAGTGACTTACAGAGGTTGTGATGCTCCAGGGCAGCCTCCACCTGCTCTTCCTTCTGAGTTGGC

1726  TCAGGCAGACAAGAGCTGCTGTCCTTTAGGAATATGTTCAATGCAAAGTAAAAAAATATGAATTGTCCCAATC
```

FIG. 2IC

```
1801  CCGGTCATGCTTTGCCACTTTGGCTTCTCCTGTGACCCCACCTTGACGGTGGGGGCGTAGACTTGACAACATCCC
1876  ACAGTGGCACGGAGAGAAGGCCCATACCTTCTGTGCTTCAGACCTGACACCGTCCCTCAGTGATACGTACAGC
1951  CAAAAGGACCAACTGGCTTCTGTGCACTAGCCTGTGATTAACTGCTTAGTATGGTTCTCAGATCTTGACAGTA
2026  TATTTGAAACTGTAAATATGTTTGCCTTAAAAGGAGAAGAAAGTGTAGATAGTTAAAGACTGCAGCTGCT
2101  GAAGTTCTGAGCCGGGCAAGTCGAGAGGGCTGTTGCACAGCTCTGTGGGCCCGGAGTAATCAGGCAGCCTTCA
2176  TAGGCGGTCATGTGTGCATGTGAGCACATGCCTATATGTGCGTCTCTCTTTCCCCCAGGTGTTGCCA
2251  TTTCTCTGCTTACCCCTTCACCTTTGGGTGTACTCTTTATTTCTAGCAGAGTCGCCCCAGTAGTCAGAAGCAGGTTCTTG
2326  ATGTCATGTACTTCCCTGTGTCCTGCTCTCTGCTCTCTTCAGGAGGATGTGTTTGCACGTGCTTGTATTGAGCA
2401  TGCACAGCTGCTTGTCCTGTCCCTGGTGTCAGGCAGGTTGCCAGTGAAGACTTCTTGGGTA
2476  GTTTAGATCCCATGTCACCTCAGCTGATATTATGGCAAGTGATATCACCTCTCTTCAGCCCTAGTGCTATTCTG
2551  TGTTGAACACAATTGATACTTCAGGTGCTTTTGATGTGAAAATCATGAAAAGAGGAACAGGTGGATGTATAGCAT
2626  TTTTATTCATGCCATCTGTTTCAACCAACTATTTTGAGGAATTATCATGGAAAAGACCAGGCTTTCCCAG
2701  GAATATCCCAAACTTCGGAAACAAGTTATTCTCTTCACTCCCAATAACTAATGCTAAGAAATGCTGAAAATCAAA
```

FIG.2ID

2776 GTAAAAATTAAAGCCCATAAGCCAGAAACTCCTTGCTGTCTTTCTCTAAATATGATTACTTAAATAAAA
2851 AAGTAACAAGGTGTCTTTTCCACTCCTATGGAAAAGGGTCTTCTTGGCAGCTTAACATGACTTCTTGGTTTGG
2926 GAGAAATAAATTTGTTCAGAATTTGTATATTGTAGGAATCCCTTTGAGAATGTGATTCCTTTGATGGGAG
3001 AAAGGGCAAATTATTTAATATTTGTATTTCAACTTTATAAAGATAAAATATCCTCAGGGTGAGAAGTGTC
3076 GTTTTCATAACTGCTGAATTTCAGGCATTTGTTCTACATGAGGACTCATATATTAAGCCTTTGTAATAA
3151 GAAAGTATAAAGTCACTTCCAGTGTTGGCTGTGTGACAGAATCTGTATTGGGCCAAGGTGTTTCCATTCTCA
3226 ATCAGTGCAGTGATACATGTACTCCAGAGGGACRGGGTGGAGCCCCCTGAGTCAACTGAGCAAGAAGGAGG
3301 CAGACTGATGGCGATTCCCTCTCACCCGGGACTCTCCCCCTTTCAAGGAAGTGAACCTTTAAAGTAAGGCCTC
3376 ATCTCCTTTATTGCAGTTCAGTCAAATCCTCAAATCTGCTCTGAATATTTGTAATAAAGGTCTTTGCACATGTTGGTTGTAAATG
3451 CTCGTGTGATTCCTACAGAAATACTGCTCTGAATATTTGTAATAAAGGTCTTTGCACATGTGACCACATACGT
3526 GTTAGGAGGCTGCATGCTCTAAGCCTGGAGCTCTTGGAAGAGCTCTTCGGTTTCTGAGCAT
3601 AATGCTCCCATCTCCTGATTTCTCTGAACAGAAACAAAGAGAGAATGAGGGAAATTGCTATTTTATTTGTATT
3676 CATGAACTTGGCTGTAATCAGTTATGCCGTATAGGATGTCAGACAATACCACTGGTTAAAATAAAGCCTATTTT
3751 CAAATTTAAAAAAAAAAAAAAAA 3775

FIG.2IE

```
1    CGCCCCAGTCGCAGGGCACATCCAGCCCGCTGACAGAGCCCGGGCCCGGGCCGAGTCTCGGGGTCGCGG

76   CAGCCGCACCTGCCGGGGCGACCAGGCCAAGGTCCCCCGGCTGGGGCGCAGCAAGGCCCGGGAGAGGGTG

151  CGGGTGCAGGGGCGGGGCCCCACAGGGCCACCTTCTGCCCGGGCCTGAAAATGTCTCAGGAGAGCC
-18                                              MetSerGlnGluArgPr

226  CACGTTCTACCGGCAGGAGCTGAACAAGACAATCTGGGAGGTGCCCGAGCGTTACCAGAACCTGTCTCAGTGG
7    oThrPheTyrArgGlnGluLeuAsnLysThrIleTrpGluValProGluArgTyrGlnAsnLeuSerProValGl

301  CTCTGGCGCCTATGGCTCTGTGTGTGCTTTGACACAAAAACGGGTTACGTGCACTGTGAAGAAGCTCTC
32   ySerGlyAlaTyrGlySerValCysAlaAlaPheAspThrLysThrGlyLeuArgValAlaValLysLysLeuSe

376  CAGACCATTCAGTCCATCATTGCGAAAGAACTACAGAGAACTGCGGTTACTAAACATATGAAACATGA
57   rArgProPheGlnSerIleIleHisAlaLysArgThrTyrArgGluLeuArgLeuLysHisMetLysHisGl

451  AAATGTGATTGGTCTCTTGGACGTTTTACACCTGCAAGGTCTCTGGAGGAATTCAATGATGTATCTGGTGAC
82   uAsnValIleGlyLeuLeuAspValPheThrProAlaArgSerLeuGluGluPheAsnAspValTyrLeuValTh

526  CCATCTCATGGGGCAGATCTGAACAACATGTGAAAATGTGAACGCTTACAGATGACCATGTTCAGTTCCTTAT
107  rHisLeuMetGlyAlaAspLeuAsnAsnIleValLysCysGlnLysLeuThrAspAspHisValGlnPheLeuIl

601  CTACCAAATTCTCCGAGTCTAAAGTATATACATTCAGCTGACATAATTCACAGGACCTAAAACCTAGTAATCT
132  eTyrGlnIleLeuArgGlyLeuLysTyrIleHisSerAlaAspIleIleHisArgAspLeuLysProSerAsnLe

676  AGCTGTGAATGAAGACTGTGAGCTGAAGATTCTGGATTTTGGACTTGCCAGATGATGAAATGACAGG
157  uAlaValAsnGluAspCysGluLeuLysIleLeuAspPheGlyLeuAlaArgHisThrAspGluMetThrGl
```

FIG.22A

```
751   CTAGGTGGCCACTAGGTGGTACAGGGCTCCTGAGATCATGCTGAACTGGATGCATTACAACCAGACAGTGATAT
182   yTyrValAlaThrArgTrpTyrArgAlaProGluIleMetLeuAsnTrpMetHisTyrAsnGlnThrValAspIl

826   TTGGTCAGTGGGATGCATAATGCCGAGCTGTTGACTGAAGAACATTGTTCCTGTACAGACCATATTGATCA
207   eTrpSerValGlyCysIleMetAlaGluLeuLeuThrGluHisCysSerCysThrAspHisIleAspGl

901   GTTGAAGCTCATTTTAAGACTCGTTGACAACCCCAGGGCTGAGCTTTTGAAGAAAATCTCCTCAGAGTCTGCAAG
232   nLeuLysLeuIleLeuArgLeuValGlyThrProGlyAlaGluLeuLeuLysLysIleSerSerGluSerAlaAr

976   AAACTATATTCAGTCTTTGACTCAGATGCCGAAGATGAACTTTGGAATGTATTATTGGTGCCAATCCCCTGCC
257   gAsnTyrIleGlnSerLeuThrGlnMetProLysMetAsnPheAlaAsnValPheIleGlyAlaAsnProLeuAl

1051  TGTCGACTTGCTGGAGAAGATGCTTGTATTGGACTCAGATAAGAGAATTACAGCGCCAAGCCCTTGCACATGC
282   aValAspLeuLeuGluLysMetLeuValLeuAspSerAspLysArgIleThrAlaAlaGlnAlaLeuAlaHisAl

1126  CTACTTTGCTCAGTACCACGATCCTGATGATGAACCAGTGGCCGATCCTTATGATCAGTCCTTTGAAAGCAGGA
307   aTyrPheAlaGlnTyrHisAspProAspAspGluProValAlaAspProTyrAspGlnSerPheGluSerArgAs

1201  CCTCCTTATAGATGAGTGGAAAAGCCTTGACCTATGAACTCATCAGCTTTGTCCACCCCCTGACCAAGA
332   pLeuLeuIleAspGluTrpLysSerLeuThrTyrAspGluValIleSerPheValProProProLeuAspGlnGl

1276  AGAGATGGAGTCCTGAGCACCTGGTTTCTGTTCTGTTGATCCCCACTTCACTGTGAGGGGAAGGCCTTTTCACGGG
357   uGluMetGluSerEnd

1351  AACTCTCCAAATATTATTCAAGTGCCAAAAA   1381
```

FIG.22B

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
       (A) LENGTH: 15 amino acids
       (B) TYPE: amino acid
       (C) STRANDEDNESS: single
       (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
       (A) ORGANISM: Homo sapiens
       (G) CELL TYPE: Monocyte
       (H) CELL LINE: THP.1

(xi) SEQUENCE DESCRIPTION: SEQ ID NO:1:

Ile Thr Ala Ala Gln Ala Leu Ala His Ala Tyr Phe Ala Gln Tyr
 1               5                  10                  15

(2) INFORMATION FOR SEQ ID NO:2:

(i) SEQUENCE CHARACTERISTICS:
       (A) LENGTH: 14 amino acids
       (B) TYPE: amino acid
       (C) STRANDEDNESS: single
       (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
       (A) ORGANISM: HOMO SAPIENS
       (G) CELL TYPE: MONOCYTE
       (H) CELL LINE: THP.1

(xi) SEQUENCE DESCRIPTION: SEQ ID NO:2:

Xaa Gln Leu Leu Asn Asn Ile Val Lys Phe Gln Lys Leu Thr
 1               5                  10

(2) INFORMATION FOR SEQ ID NO:3:

(i) SEQUENCE CHARACTERISTICS:
       (A) LENGTH: 22 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: YES (iv) ANTI-SENSE: NO (vi) ORIGINAL SOURCE:
       (A) ORGANISM: HOMO SAPIENS
       (G) CELL TYPE: MONOCYTE

```
       (xi) SEQUENCE DESCRIPTION: SEQ ID NO:3:

GCYCAYGCTA YTTYGCYCAR TA                                                      22

(2) INFORMATION FOR SEQ ID NO:4:

(i) SEQUENCE CHARACTERISTICS:
          (A) LENGTH: 22 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: YES (iv) ANTI-SENSE: NO (vi) ORIGINAL SOURCE:
          (A) ORGANISM: HOMO SAPIENS
          (G) CELL TYPE: MONOCYTE (xi) SEQUENCE DESCRIPTION: SEQ ID NO:4:

AAYAAYATYK TBAARTTYCA AA                                                      22

(2) INFORMATION FOR SEQ ID NO:5:

(i) SEQUENCE CHARACTERISTICS:
          (A) LENGTH: 9 amino acids
          (B) TYPE: amino acid
          (C) STRANDEDNESS: single
          (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
          (A) ORGANISM: HOMO SAPIENS
          (G) CELL TYPE: MONOCYTE
          (H) CELL LINE: THP.1

(xi) SEQUENCE DESCRIPTION: SEQ ID NO:5:

Asn Ile Val Lys Cys Gln Lys Leu Thr
       1               5

(2) INFORMATION FOR SEQ ID NO:6:

(i) SEQUENCE CHARACTERISTICS:
          (A) LENGTH: 285 base pairs
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (vi) ORIGINAL SOURCE:
          (A) ORGANISM: HOMO SAPIENS
          (G) CELL TYPE: MONOCYTE
          (H) CELL LINE: THP.1

(ix) FEATURE:
          (A) NAME/KEY: CDS
          (B) LOCATION: 1..285

(xi) SEQUENCE DESCRIPTION: SEQ ID NO:6:
```

```
AAC ATT GTG AAA TGT CAG AAG CTT ACA GAT GAC CAT GTT CAG TTC CTT        48
Asn Ile Val Lys Cys Gln Lys Leu Thr Asp Asp His Val Gln Phe Leu
 1               5                  10                  15

ATC TAC CAA ATT CTC CGA GGT CTA AAG TAT ATA CAT TCA GCT GAC ATA        96
Ile Tyr Gln Ile Leu Arg Gly Leu Lys Tyr Ile His Ser Ala Asp Ile
             20                  25                  30

ATT CAC AGG GAC CTA AAA CCT AGT AAT CTA GCT GTG AAT GAA GAC TGT       144
Ile His Arg Asp Leu Lys Pro Ser Asn Leu Ala Val Asn Glu Asp Cys
         35                  40                  45

GAG CTG AAG ATT CTG GAT TTT GGA CTG GCT CGG CAC ACA GAT GAT GAA       192
Glu Leu Lys Ile Leu Asp Phe Gly Leu Ala Arg His Thr Asp Asp Glu
 50                  55                  60

ATG ACA GGC TAC GTG GCC ACT AGG TGG TAC AGG GCT CCT GAG ATC ATG       240
Met Thr Gly Tyr Val Ala Thr Arg Trp Tyr Arg Ala Pro Glu Ile Met
 65                  70                  75                  80

CTG AAC TGG ATG CAT TAC AAC CAG ACA GGT GGT ATT TGG GTC AAG           285
Leu Asn Trp Met His Tyr Asn Gln Thr Gly Gly Ile Trp Val Lys
             85                  90                  95
```

(2) INFORMATION FOR SEQ ID NO:7:

(i) SEQUENCE CHARACTERISTICS:
        (A) LENGTH: 95 amino acids
        (B) TYPE: amino acid
        (D) TOPOLOGY: linear (ii) MOLECULE TYPE: protein (xi) SEQUENCE DESCRIPTION: SEQ ID NO:7:

```
Asn Ile Val Lys Cys Gln Lys Leu Thr Asp Asp His Val Gln Phe Leu
 1               5                  10                  15

Ile Tyr Gln Ile Leu Arg Gly Leu Lys Tyr Ile His Ser Ala Asp Ile
             20                  25                  30

Ile His Arg Asp Leu Lys Pro Ser Asn Leu Ala Val Asn Glu Asp Cys
         35                  40                  45

Glu Leu Lys Ile Leu Asp Phe Gly Leu Ala Arg His Thr Asp Asp Glu
 50                  55                  60

Met Thr Gly Tyr Val Ala Thr Arg Trp Tyr Arg Ala Pro Glu Ile Met
 65                  70                  75                  80

Leu Asn Trp Met His Tyr Asn Gln Thr Gly Gly Ile Trp Val Lys
             85                  90                  95
```

(2) INFORMATION FOR SEQ ID NO:8:

(i) SEQUENCE CHARACTERISTICS:
        (A) LENGTH: 392 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: HOMO SAPIENS
        (G) CELL TYPE: MONOCYTE
        (H) CELL LINE: THP.1

(ix) FEATURE:
        (A) NAME/KEY: 3'UTR
        (B) LOCATION: 1..392

(xi) SEQUENCE DESCRIPTION: SEQ ID NO:8:

```
CAAGTCCCAA TCCTCCCCAA CCACAGCAAG TTGAATTTAT CAACCATGTT GGGTTGTAAA        60

TGCTCGTGTG ATTTCCTACA AGAAATACCT GCTCTGAATA TTTTTGTAAT AAAGGTCTTT       120

GCACATGTGA CCCACAATAC GTGTTAGGAG CCTGCATGCT CTGGAAGCCT GGACTCTAAG       180

CTGGAGCTCT TGGAAGAGCT CTTCGGTTTC TGAGCATAAT GCTCCCATCT CCTGATTTCT       240

CTGAACAGAA AACAAAGAG AGAATGAGGG AAATTGCTAT TTTATTTGTA TTGATGAACT        300

TGGCTGTAAT CAGTTATGCC GTATAGGATG TCAGACAATA CCACTGGTTA AAATAAAGCC       360

TATTTTTCAA ATTTAAAAAA AAAAAAAAAA AA                                    392
```

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens
        (G) CELL TYPE: Monocyte (xi) SEQUENCE DESCRIPTION: SEQ ID NO:9:

```
CCTCGGAGAA TTTGGTAGAT AAGG                                              24
```

(2) INFORMATION FOR SEQ ID NO:10:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens
        (G) CELL TYPE: Monocyte (xi) SEQUENCE DESCRIPTION: SEQ ID NO:10:

```
AACATTGTGA AATGTCAGAA GCTTACAGAT GACCAT                                 36
```

(2) INFORMATION FOR SEQ ID NO:11:

(i) SEQUENCE CHARACTERISTICS:
        (A) LENGTH: 3774 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens
        (G) CELL TYPE: Monocyte (ix) FEATURE:

(A) NAME/KEY: CDS
(B) LOCATION: 379..1461

(xi) SEQUENCE DESCRIPTION: SEQ ID NO:11:

```
GGAACCGCGA CCACTGGAGC CTTAGCGGGC GCAGCAGCTG GAACGGGAGT ACTGCGACGC    60

AGCCCGGAGT CGGCCTTGTA GGGGCGAAGG TGCAGGGAGA TCGCGGCGGG CGCAGTCTTG   120

AGCGCCGGAG CGCGTCCCTG CCCTTAGCGG GGCTTGCCCC AGTCGCAGGG GCACATCCAG   180

CCGCTGCGGC TGACAGCAGC CGCGCGCGCG GGAGTCTGCG GGGTCGCGGC AGCCGCACCT   240

GCGCGGGCGA CCAGCGCAAG GTCCCCGCCC GGCTGGGCGG GCAGCAAGGG CCGGGGAGAG   300

GGTGCGGGTG CAGGCGGGGG CCCCACAGGG CCACCTTCTT GCCCGGCGGC TGCCGCTGGA   360

AAATGTCTCA GGAGAGGCCC ACGTTCTACC GGCAGGAGCT GAACAAGACA ATCTGGGAGG   420

TGCCCGAGCG TTACCAGAAC CTGTCTCCAG TGGGCTCTGG CGCCTATGGC TCTGTGTGTG   480

CTGCTTTTGA CACAAAAACG GGGTTACGTG TGGCAGTGAA GAAGCTCTCC AGACCATTTC   540

AGTCCATCAT TCATGCGAAA AGAACCTACA GAGAACTGCG GTTACTTAAA CATATGAAAC   600

ATGAAAATGT GATTGGTCTG TTGGACGTTT TTACACCTGC AAGGTCTCTG GAGGAATTCA   660

ATGATGTGTA TCTGGTGACC CATCTCATGG GGGCAGATCT GAACAACATT GTGAAATGTC   720

AGAAGCTTAC AGATGACCAT GTTCAGTTCC TTATCTACCA AATTCTCCGA GGTCTAAAGT   780

ATATACATTC AGCTGACATA ATTCACAGGG ACCTAAAACC TAGTAATCTA GCTGTGAATG   840

AAGACTGTGA GCTGAAGATT CTGGATTTTG GACTGGCTCG GCACACAGAT GATGAAATGA   900

CAGGCTACGT GGCCACTAGG TGGTACAGGG CTCCTGAGAT CATGCTGAAC TGGATGCATT   960

ACAACCAGAC AGTTGATATT TGGTCAGTGG GATGCATAAT GGCCGAGCTG TTGACTGGAA  1020

GAACATTGTT TCCTGGTACA GACCATATTA CCAGCTTCA GCAGATTATG CGTCTGACAG  1080

GAACACCCCC CGCTTATCTC ATTAACAGGA TGCCAAGCCA TGAGGCAAGA AACTATATTC  1140

AGTCTTTGAC TCAGATGCCG AAGATGAACT TTGCGAATGT ATTTATTGGT GCCAATCCCC  1200

TGGCTGTCGA CTTGCTGGAG AAGATGCTTG TATTGGACTC AGATAAGAGA ATTACAGCGG  1260

CCCAAGCCCT TGCACATGCC TACTTTGCTC AGTACCACGA TCCTGATGAT GAACCAGTGG  1320

CCGATCCTTA TGATCAGTCC TTTGAAAGCA GGGACCTCCT TATAGATGAG TGGAAAAGCC  1380

TGACCTATGA TGAAGTCATC AGCTTTGTGC CACCACCCCT TGACCAAGAA GAGATGGAGT  1440

CCTGAGCACC TGGTTTCTGT TCTGTTGATC CCACTTCACT GTGAGGGGAA GGCCTTTTCA  1500

CGGGAACTCT CCAAATATTA TTCAAGTGCC TCTTGTTGCA GAGATTTCCT CCATGGTGGA  1560

AGGGGGTGTG CGTGCGTGTG CGTGCGTGTT AGTGTGTGTG CATGTGTGTG TCTGTCTTTG  1620

TGGGAGGGTA AGACAATATG AACAAACTAT GATCACAGTG ACTTTACAGG AGGTTGTGGA  1680

TGCTCCAGGG CAGCCTCCAC CTTGCTCTTC TTTCTGAGAG TTGGCTCAGG CAGACAAGAG  1740

CTGCTGTCCT TTTAGGAATA TGTTCAATGC AAAGTAAAAA AATATGAATT GTCCCCAATC  1800

CCGGTCATGC TTTTGCCACT TTGGCTTCTC CTGTGACCCC ACCTTGACGG TGGGGCGTAG  1860

ACTTGACAAC ATCCCACAGT GGCACGGAGA GAAGGCCCAT ACCTTCTGGT GCTTCAGAC  1920

CTGACACCGT CCCTCAGTGA TACGTACAGC CAAAAGGAC CAACTGGCTT CTGTGCACTA  1980

GCCTGTGATT AACTTGCTTA GTATGGTTCT CAGATCTTGA CAGTATATTT GAAACTGTAA  2040

ATATGTTTGT GCCTTAAAAG GAGAGAAGAA AGTGTAGATA GTTAAAAGAC TGCAGCTGCT  2100

GAAGTTCTGA GCCGGGCAAG TCGAGAGGGC TGTTGGACAG CTGCTTGTGG GCCCGGAGTA  2160

ATCAGGCAGC CTTCATAGGC GGTCATGTGT GCATGTGAGC ACATGCGTAT ATGTGCGTCT  2220

CTCTTTCTCC CTCACCCCCA GGTGTTGCCA TTTCTCTGCT TACCCTTCAC CTTTGGTGCA  2280
```

```
GAGGTTTCTT GAATATCTGC CCCAGTAGTC AGAAGCAGGT TCTTGATGTC ATGTACTTCC    2340

TGTGTACTCT TTATTTCTAG CAGAGTGAGG ATGTGTTTTG CACGTCTTGC TATTTGAGCA    2400

TGCACAGCTG CTTGTCCTGC TCTCTTCAGG AGGCCCTGGT GTCAGGCAGG TTTGCCAGTG    2460

AAGACTTCTT GGGTAGTTTA GATCCCATGT CACCTCAGCT GATATTATGG CAAGTGATAT    2520

CACCTCTCTT CAGCCCCTAG TGCTATTCTG TGTTGAACAC AATTGATACT TCAGGTGCTT    2580

TTGATGTGAA AATCATGAAA AGAGGAACAG GTGGATGTAT AGCATTTTTA TTCATGCCAT    2640

CTGTTTTCAA CCAACTATTT TTGAGGAATT ATCATGGGAA AAGACCAGGG CTTTTCCCAG    2700

GAATATCCCA AACTTCGGAA ACAAGTTATT CTCTTCACTC CCAATAACTA ATGCTAAGAA    2760

ATGCTGAAAA TCAAAGTAAA AAATTAAAGC CCATAAGGCC AGAAACTCCT TTTGCTGTCT    2820

TTCTCTAAAT ATGATTACTT TAAAATAAAA AAGTAACAAG GTGTCTTTTC CACTCCTATG    2880

GAAAAGGGTC TTCTTGGCAG CTTAACATTG ACTTCTTGGT TTGGGGAGAA ATAAATTTTG    2940

TTTCAGAATT TTGTATATTG TAGGAATCCC TTTGAGAATG TGATTCCTTT TGATGGGGAG    3000

AAAGGGCAAA TTATTTTAAT ATTTTGTATT TTCAACTTTA TAAAGATAAA ATATCCTCAG    3060

GGGTGGAGAA GTGTCGTTTT CATAACTTGC TGAATTTCAG GCATTTTGTT CTACATGAGG    3120

ACTCATATAT TTAAGCCTTT TGTGTAATAA GAAAGTATAA AGTCACTTCC AGTGTTGGCT    3180

GTGTGACAGA ATCTTGTATT TGGGCCAAGG TGTTTCCATT TCTCAATCAG TGCAGTGATA    3240

CATGTACTCC AGAGGGACGG GTGGACCCCC TGAGTCAACT GGAGCAAGAA GGAAGGAGGC    3300

AGACTGATGG CGATTCCCTC TCACCCGGGA CTCTCCCCCT TTCAAGGAAA GTGAACCTTT    3360

AAAGTAAAGG CCTCATCTCC TTTATTGCAG TTCAAATCCT CACCATCCAC AGCAAGATGA    3420

ATTTTATCAG CCATGTTTGG TTGTAAATGC TCGTGTGATT TCCTACAGAA ATACTGCTCT    3480

GAATATTTTG TAATAAAGGT CTTTGCACAT GTGACCACAT ACGTGTTAGG AGGCTGCATG    3540

CTCTGGAAGC CTGGACTCTA AGCTGGAGCT CTTGGAAGAG CTCTTCGGTT TCTGAGCATA    3600

ATGCTCCCAT CTCCTGATTT CTCTGAACAG AAAACAAAAG AGAGAATGAG GGAAATTGCT    3660

ATTTTATTTG TATTCATGAA CTTGGCTGTA ATCAGTTATG CCGTATAGGA TGTCAGACAA    3720

TACCACTGGT TAAAATAAAG CCTATTTTTC AAATTTAAAA AAAAAAAAA AAAA           3774
```

(2) INFORMATION FOR SEQ ID NO:12:

(i) SEQUENCE CHARACTERISTICS:
        (A) LENGTH: 360 amino acids
        (B) TYPE: amino acid
        (D) TOPOLOGY: linear (ii) MOLECULE TYPE: protein (xi) SEQUENCE DESCRIPTION: SEQ ID NO:12:

```
Met Ser Gln Glu Arg Pro Thr Phe Tyr Arg Gln Glu Leu Asn Lys Thr
 1               5                  10                  15

Ile Trp Glu Val Pro Glu Arg Tyr Gln Asn Leu Ser Pro Val Gly Ser
                20                  25                  30

Gly Ala Tyr Gly Ser Val Cys Ala Ala Phe Asp Thr Lys Thr Gly Leu
            35                  40                  45

Arg Val Ala Val Lys Lys Leu Ser Arg Pro Phe Gln Ser Ile Ile His
        50                  55                  60

Ala Lys Arg Thr Tyr Arg Glu Leu Arg Leu Leu Lys His Met Lys His
    65                  70                  75                  80

Glu Asn Val Ile Gly Leu Leu Asp Val Phe Thr Pro Ala Arg Ser Leu
                85                  90                  95
```

```
Glu Glu Phe Asn Asp Val Tyr Leu Val Thr His Leu Met Gly Ala Asp
            100                 105                 110

Leu Asn Asn Ile Val Lys Cys Gln Lys Leu Thr Asp Asp His Val Gln
            115                 120                 125

Phe Leu Ile Tyr Gln Ile Leu Arg Gly Leu Lys Tyr Ile His Ser Ala
            130                 135                 140

Asp Ile Ile His Arg Asp Leu Lys Pro Ser Asn Leu Ala Val Asn Glu
145                 150                 155                 160

Asp Cys Glu Leu Lys Ile Leu Asp Phe Gly Leu Ala Arg His Thr Asp
                165                 170                 175

Asp Glu Met Thr Gly Tyr Val Ala Thr Arg Trp Tyr Arg Ala Pro Glu
            180                 185                 190

Ile Met Leu Asn Trp Met His Tyr Asn Gln Thr Val Asp Ile Trp Ser
            195                 200                 205

Val Gly Cys Ile Met Ala Glu Leu Leu Thr Gly Arg Thr Leu Phe Pro
            210                 215                 220

Gly Thr Asp His Ile Asn Gln Leu Gln Gln Ile Met Arg Leu Thr Gly
225                 230                 235                 240

Thr Pro Pro Ala Tyr Leu Ile Asn Arg Met Pro Ser His Glu Ala Arg
                245                 250                 255

Asn Tyr Ile Gln Ser Leu Thr Gln Met Pro Lys Met Asn Phe Ala Asn
            260                 265                 270

Val Phe Ile Gly Ala Asn Pro Leu Ala Val Asp Leu Leu Glu Lys Met
            275                 280                 285

Leu Val Leu Asp Ser Asp Lys Arg Ile Thr Ala Ala Gln Ala Leu Ala
            290                 295                 300

His Ala Tyr Phe Ala Gln Tyr His Asp Pro Asp Asp Glu Pro Val Ala
305                 310                 315                 320

Asp Pro Tyr Asp Gln Ser Phe Glu Ser Arg Asp Leu Leu Ile Asp Glu
                325                 330                 335

Trp Lys Ser Leu Thr Tyr Asp Glu Val Ile Ser Phe Val Pro Pro Pro
            340                 345                 350

Leu Asp Gln Glu Glu Met Glu Ser
            355                 360

(2) INFORMATION FOR SEQ ID NO:13:

(i) SEQUENCE CHARACTERISTICS:
        (A) LENGTH: 1381 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens
        (G) CELL TYPE: Monocyte (ix) FEATURE:
        (A) NAME/KEY: CDS
        (B) LOCATION: 227..1309

(xi) SEQUENCE DESCRIPTION: SEQ ID NO:13:

CGCCCCAGTC GCAGGGGCAC ATCCAGCCGC TGCGGCTGAC AGCAGCCGCG CGCGCGGGAG    60

TCTGCGGGGT CGCGGCAGCC GCACCTGCGC GGGCGACCAG CGCAAGGTCC CCGCCCGGCT   120
```

```
GGGCGGGCAG CAAGGGCCGG GGAGAGGGTG CGGGTGCAGG CGGGGGCCCC ACAGGGCCAC      180

CTTCTTGCCC GGCGGCTGCC GCTGGAAAAT GTCTCAGGAG AGGCCCACGT TCTACCGGCA      240

GGAGCTGAAC AAGACAATCT GGGAGGTGCC CGAGCGTTAC CAGAACCTGT CTCCAGTGGG      300

CTCTGGCGCC TATGGCTCTG TGTGTGCTGC TTTTGACACA AAAACGGGGT TACGTGTGGC      360

AGTGAAGAAG CTCTCCAGAC CATTTCAGTC CATCATTCAT GCAAAAGAA CCTACAGAGA       420

ACTGCGGTTA CTTAAACATA TGAAACATGA AAATGTGATT GGTCTGTTGG ACGTTTTTAC      480

ACCTGCAAGG TCTCTGGAGG AATTCAATGA TGTGTATCTG GTGACCCATC TCATGGGGGC      540

AGATCTGAAC AACATTGTGA AATGTCAGAA GCTTACAGAT GACCATGTTC AGTTCCTTAT      600

CTACCAAATT CTCCGAGGTC TAAAGTATAT ACATTCAGCT GACATAATTC ACAGGGACCT      660

AAAACCTAGT AATCTAGCTG TGAATGAAGA CTGTGAGCTG AAGATTCTGG ATTTTGGACT      720

GGCTCGGCAC ACAGATGATG AAATGACAGG CTACGTGGCC ACTAGGTGGT ACAGGGCTCC      780

TGAGATCATG CTGAACTGGA TGCATTACAA CCAGACAGTT GATATTTGGT CAGTGGGATG      840

CATAATGGCC GAGCTGTTGA CTGGAAGAAC ATTGTTTCCT GGTACAGACC ATATTGATCA      900

GTTGAAGCTC ATTTTAAGAC TCGTTGGAAC CCCAGGGGCT GAGCTTTTGA AGAAAATCTC      960

CTCAGAGTCT GCAAGAAACT ATATTCAGTC TTTGACTCAG ATGCCGAAGA TGAACTTTGC     1020

GAATGTATTT ATTGGTGCCA ATCCCCTGGC TGTCGACTTG CTGGAGAAGA TGCTTGTATT     1080

GGACTCAGAT AAGAGAATTA CAGCGGCCCA AGCCCTTGCA CATGCCTACT TTGCTCAGTA     1140

CCACGATCCT GATGATGAAC CAGTGGCCGA TCCTTATGAT CAGTCCTTTG AAAGCAGGGA     1200

CCTCCTTATA GATGAGTGGA AAGCCTGAC CTATGATGAA GTCATCAGCT TTGTGCCACC      1260

ACCCCTTGAC CAAGAAGAGA TGGAGTCCTG AGCACCTGGT TTCTGTTCTG TTGATCCCAC     1320

TTCACTGTGA GGGGAAGGCC TTTTCACGGG AACTCTCCAA ATATTATTCA AGTGCCAAAA     1380

A                                                                     1381
```

(2) INFORMATION FOR SEQ ID NO:14:

(i) SEQUENCE CHARACTERISTICS:
        (A) LENGTH: 360 amino acids
        (B) TYPE: amino acid
        (D) TOPOLOGY: linear (ii) MOLECULE TYPE: protein (xi) SEQUENCE DESCRIPTION: SEQ ID NO:14:

```
Met Ser Gln Glu Arg Pro Thr Phe Tyr Arg Gln Leu Asn Lys Thr
 1               5                  10                  15

Ile Trp Glu Val Pro Glu Arg Tyr Gln Asn Leu Ser Pro Val Gly Ser
                20                  25                  30

Gly Ala Tyr Gly Ser Val Cys Ala Ala Phe Asp Thr Lys Thr Gly Leu
                35                  40                  45

Arg Val Ala Val Lys Lys Leu Ser Arg Pro Phe Gln Ser Ile Ile His
            50                  55                  60

Ala Lys Arg Thr Tyr Arg Glu Leu Arg Leu Leu Lys His Met Lys His
65                  70                  75                  80

Glu Asn Val Ile Gly Leu Leu Asp Val Phe Thr Pro Ala Arg Ser Leu
                85                  90                  95

Glu Glu Phe Asn Asp Val Tyr Leu Val Thr His Leu Met Gly Ala Asp
                100                 105                 110

Leu Asn Asn Ile Val Lys Cys Gln Lys Leu Thr Asp Asp His Val Gln
            115                 120                 125
```

```
Phe Leu Ile Tyr Gln Ile Leu Arg Gly Leu Lys Tyr Ile His Ser Ala
    130                 135                 140

Asp Ile Ile His Arg Asp Leu Lys Pro Ser Asn Leu Ala Val Asn Glu
145                 150                 155                 160

Asp Cys Glu Leu Lys Ile Leu Asp Phe Gly Leu Ala Arg His Thr Asp
            165                 170                 175

Asp Glu Met Thr Gly Tyr Val Ala Thr Arg Trp Tyr Arg Ala Pro Glu
            180                 185                 190

Ile Met Leu Asn Trp Met His Tyr Asn Gln Thr Val Asp Ile Trp Ser
        195                 200                 205

Val Gly Cys Ile Met Ala Glu Leu Leu Thr Gly Arg Thr Leu Phe Pro
210                 215                 220

Gly Thr Asp His Ile Asp Gln Leu Lys Leu Ile Leu Arg Leu Val Gly
225                 230                 235                 240

Thr Pro Gly Ala Glu Leu Leu Lys Lys Ile Ser Ser Glu Ser Ala Arg
                245                 250                 255

Asn Tyr Ile Gln Ser Leu Thr Gln Met Pro Lys Met Asn Phe Ala Asn
                260                 265                 270

Val Phe Ile Gly Ala Asn Pro Leu Ala Val Asp Leu Leu Glu Lys Met
            275                 280                 285

Leu Val Leu Asp Ser Asp Lys Arg Ile Thr Ala Ala Gln Ala Leu Ala
        290                 295                 300

His Ala Tyr Phe Ala Gln Tyr His Asp Pro Asp Asp Glu Pro Val Ala
305                 310                 315                 320

Asp Pro Tyr Asp Gln Ser Phe Glu Ser Arg Asp Leu Leu Ile Asp Glu
                325                 330                 335

Trp Lys Ser Leu Thr Tyr Asp Glu Val Ile Ser Phe Val Pro Pro Pro
                340                 345                 350

Leu Asp Gln Glu Glu Met Glu Ser
                355                 360

(2) INFORMATION FOR SEQ ID NO:15:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:15:

CGCCCTCGAG ATGTCTCAGG AGAGGCCCAC G                                    31

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO
```

(xi) SEQUENCE DESCRIPTION: SEQ ID NO:16:

GCCAGTCCAA AATCCAGAAT C                                              21

(2) INFORMATION FOR SEQ ID NO:17:

(i) SEQUENCE CHARACTERISTICS:
        (A) LENGTH: 16 amino acids
        (B) TYPE: amino acid
        (D) TOPOLOGY: linear (ii) MOLECULE TYPE: protein (xi) SEQUENCE DESCRIPTION: SEQ ID NO:17:

Ile Thr Ala Ala Gln Ala Leu Ala His Ala Tyr Phe Ala Gln Tyr Cys
 1               5                  10                  15

(2) INFORMATION FOR SEQ ID NO:18:

(i) SEQUENCE CHARACTERISTICS:
        (A) LENGTH: 1100 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:18:

GCCGCTGGAA AATGTCTCAG GAGAGGCCCA CGTTCTACCG GCAGGAGCTG AACAAGACAA      60
TCTGGGAGGT GCCCGAGCGT TACCAGAACC TGTCTCCAGT GGGCTCTGGC GCCTATGGCT     120
CTGTGTGTGC TGCTTTTGAC ACAAAAACGG GGTTACGTGT GGCAGTGAAG AAGCTCTCCA     180
GACCATTTCA GTCCATCATT CATGCGAAAA GAACCTACAG AGAACTGCGG TTACTTAAAC     240
ATATGAAACA TGAAAATGTG ATTGGTCTGT TGGACGTTTT TACACCTGCA AGGTCTCTGG     300
AGGAATTCAA TGATGTGTAT CTGGTGACCC ATCTCATGGG GGCAGATCTG AACAACATTG     360
TGAAATGTCA GAAGCTTACA GATGACCATG TTCAGTTCCT TATCTACCAA ATTCTCCGAG     420
GTCTAAAGTA TATACATTCA GCTGACATAA TTCACAGGGA CCTAAAACCT AGTAATCTAG     480
CTGTGAATGA AGACTGTGAG CTGAAGATTC TGGATTTTGG ACTGGCTCGG CACACAGATG     540
ATGAAATGAC AGGCTACGTG GCCACTAGGT GGTACAGGGC TCCTGAGATC ATGCTGAACT     600
GGATGCATTA CAACCAGACA GTTGATATTT GGTCAGTGGG ATGCATAATG GCCGAGCTGT     660
TGACTGGAAG AACATTGTTT CCTGGTACAG ACCATATTAA CCAGCTTCAG CAGATTATGC     720
GTCTGACAGG AACACCCCCC GCTTATCTCA TTAACAGGAT GCCAAGCCAT GAGGCAAGAA     780
ACTATATTCA GTCTTTGACT CAGATGCCGA AGATGAACTT TGCGAATGTA TTTATTGGTG     840
CCAATCCCCT GGCTGTCGAC TTGCTGGAGA AGATGCTTGT ATTGGACTCA GATAAGAGAA     900
TTACAGCGGC CCAAGCCCTT GCACATGCCT ACTTTGCTCA GTACCACGAT CCTGATGATG     960
AACCAGTGGC CGATCCTTAT GATCAGTCCT TTGAAAGCAG GGACCTCCTT ATAGATGAGT    1020
GGAAAAGCCT GACCTATGAT GAAGTCATCA GCTTTGTGCC ACCACCCCTT GACCAAGAAG    1080
AGATGGAGTC CTGAGCACCT                                               1100

(2) INFORMATION FOR SEQ ID NO:19:

(i) SEQUENCE CHARACTERISTICS:
        (A) LENGTH: 9 amino acids
        (B) TYPE: amino acid -continued

```
        (D) TOPOLOGY: linear (ii) MOLECULE TYPE: protein (xi) SEQUENCE DESCRIPTION: SEQ ID NO:19:

Met Asp Tyr Lys Asp Asp Asp Lys
1               5
```

POLYNUCLEOTIDES ENCODING CYTOKINE SUPPRESSIVE ANTI-INFLAMMATORY DRUG BINDING PROTEINS

CROSS-REFERENCE TO RELATED APPLICATION

This application is a continuation application of U.S. application Ser. No. 08/250,975, filed on May 31, 1994, now U.S. Pat. No. 5,783,664, which was a continuation-in-part application of U.S. application Ser. No. 08/123,175, filed on Sep. 17, 1993, now abandoned, the contents of which are incorporated herein by reference.

FIELD OF THE INVENTION

This invention relates to drug binding proteins, to genes encoding same and to assays and methods for screening pharmaceuticals. More specifically, this invention relates to Cytokine Suppressive Anti-Inflammatory Drug (CSAID) binding proteins, to genes encoding same and to assays and screens useful in the evaluation and characterization of drugs of this pharmacologic class.

BACKGROUND OF THE INVENTION

Cytokines play an important role in regulating the cellular response during inflammation and other immune functions. Of particular interest are the cytokines interleukin-1 (IL-1, $\alpha$ and $\beta$) and tumor necrosis factor (TNF, $\alpha$ and $\beta$), which are the intercellular proteins involved in the initial step of the inflammatory response cascade (Arai, et al, *Ann. Rev. Biochem.* 59: 783–836 (1990)). Thus, there has been a substantial amount of research recently devoted to interfering with the production of IL-1 and TNF in response to an inflammatory stimulus.

One therapeutic approach involves suppressing the production of IL-1 and TNF at the level of transcription and/or translation and/or secretion. The activities associated with certain of pyridinyl imidazoles led to a class of compounds referred to as "CSAIDs", or Cytokine Suppressing Anti-Inflammatory Drugs (FIG. 1). These compounds appear to arrest the expression of IL-1 and TNF predominantly at the translational level, although a lesser effect on transcription has also been observed but effects on other steps cannot be ruled out.

The pyridinyl imidazole, 5-(4-pyridyl)-6(4-fluorophenyl)-2,3-dihydroimidazo(2,1-b)thiazole (SK&F 86002) was identified as the prototypic CSAID. The basis for its activity has been established and characterized (Lee, et al., *Int'l. J. Immunopharm.* 10(7): 835–843 (1988); *Agents and Actions* 27(¾): 277–279 (1989) and *Int'l. J. Immunother.* 6(1):1–12 (1990)). SAR studies (discussed herein) suggest that cytokine suppressive effect of the pyridinyl imidazoles represents a unique activity independent of their inhibitory effects on eicosanoid and leukotriene production. However, no compound of the initial series was selective for cytokine suppressive activity or was particularly potent.

Since the CSAIDs have substantial potential as novel anti-inflammatory therapeutic agents, there is significant interest in characterizing their mechanism of action at the molecular level, as well as obtaining compounds with increased selectivity and potency. Specifically, identification and characterization of the CSAID molecular target would enhance the understanding of the biochemical processes involved in inflammation and aid in the design and screening of more potent anti-inflammatory drugs. This invention discloses, inter alia, the purification and characterization of such CSAID binding proteins (CSBPs).

The DNAs of this invention, such as the specific sequences disclosed herein, are useful in that they encode the genetic information required for the expression of the novel CSBPs. Additionally, the sequences may be used as probes in order to isolate and identify any additional members of the CSBP family as well as forming the basis of antisense therapy for disease conditions which are characterized by atypical expression of the CSBP gene. The novel protein itself is useful directly as a therapeutic or diagnostic agent as well as a component in a screening system for compounds which are antagonists or agonists of CSAID binding activity. The protein is also useful for eliciting antibody production in heterologous species, said antibodies being useful for the aforesaid diagnostic, therapeutic and screening applications. These and additional uses for the reagents described herein will become apparent to those of ordinary skill in the art upon reading this specification.

BRIEF DESCRIPTION OF THE INVENTION

This invention provides isolated nucleic acid molecules encoding a CSAID binding protein, including mRNAs, DNAs, cDNAs as well as antisense analogs thereof and biologically active and diagnostically or therapeutically useful fragments thereof.

This invention also provides recombinant vectors, such as cloning and expression plasmids useful as reagents in the recombinant production of CSAID binding proteins or peptides, as well as recombinant prokaryotic and/or eukaryotic host cells comprising the CSBP encoding nucleic acid sequence.

This invention also provides methods of identifying ligands capable of binding to the CSBP by measuring the binding of the ligand to be identified relative to known ligands.

This invention also provides methods for screening drugs to identify compounds which interact with and bind to the CSBP. The binding protein may be in isolated form in solution, or in immobilized form, or may be genetically engineered to be expressed on the surface of recombinant host cells such as in phage display system or as fusion proteins. Alternatively, whole cells or cytosolic fractions comprising the CSBP may be employed in screening protocols. Regardless of the form of the binding protein, a plurality of compounds are contacted with the binding protein under conditions sufficient to form a compound/binding protein complex and compound capable of forming, enhancing or interfering with said complexes are detected.

This invention also provides nucleic acid probes comprising nucleic acid molecules of sufficient length to specifically hybridize to CSAID binding protein-like sequences.

This invention also provides an antisense oligonucleotide having a sequence capable of binding with mRNAs encoding the CSBP so as to prevent the translation of said MRNA.

This invention also provides transgenic non-human animals comprising or lacking a nucleic acid molecule encoding a CSBP. Also provided are methods for use of said transgenic animals as models for differential binding protein expression, mutation and SAR evaluation as well as in ligand and drug screens.

This invention also provides fusion proteins comprising a CSAID binding domain and a binding protein/ligand binding indicator domain capable of providing an analytically detectable signal. Also provided are methods of screening drugs by forming, enhancing or interfering with the detectable signal.

This invention also provides a method of screening compounds to identify those compounds which bind to a CSAID binding protein comprising: providing a recombinant host cell expressing on the surface thereof a CSAID binding protein, said protein being associated with a second component capable of providing a detectable signal in response to the binding of a compound to said protein; contacting a plurality of candidate compounds with said host cells under conditions sufficient to permit binding of compounds to the binding protein; and identifying those compounds capable of binding by detecting the signal produced by said second component.

BRIEF DESCRIPTION OF THE FIGURES

FIG. 13 illustrates the nucleic acid sequence (SEQ ID NO: 6) and amino sequence (SEQ ID NO: 7) of a portion of the CSAIDs Binding Protein.

FIG. 14 illustrates the nucleic acid sequence (SEQ ID NO: 8) of a second portion of the CSAIDs Binding Protein.

FIGS. 16A to 16B illustrate the cDNA and amino acid sequence cDNA sequence (SEQ ID NO: 18) and amino acid sequence (SEQ ID NO: 12) of one of the CSBPs disclosed herein.

FIG. 17 illustrates the difference in nucleotide and amino acid sequence between CSBP1 (SEQ ID NO: 12) and CSBP2 (SEQ ID NO: 14).

FIG. 19 illustrates the alignment of the amino acid sequences of CSBP-1 (SEQ ID NO: 12 ) and CSBP-2 (SEQ ID NO: 14) with selected members of the protein kinase family.

FIGS. 21A–21E illustrate the full length nucleic acid sequence of CSBP-1 cDNA (SEQ ID NO: 11).

FIGS. 22A–22B illustrate the full length nucleic acid sequence of CSBP-2 cDNA (SEQ ID NO: 13).

DETAILED DESCRIPTION OF THE INVENTION

Figure 1:
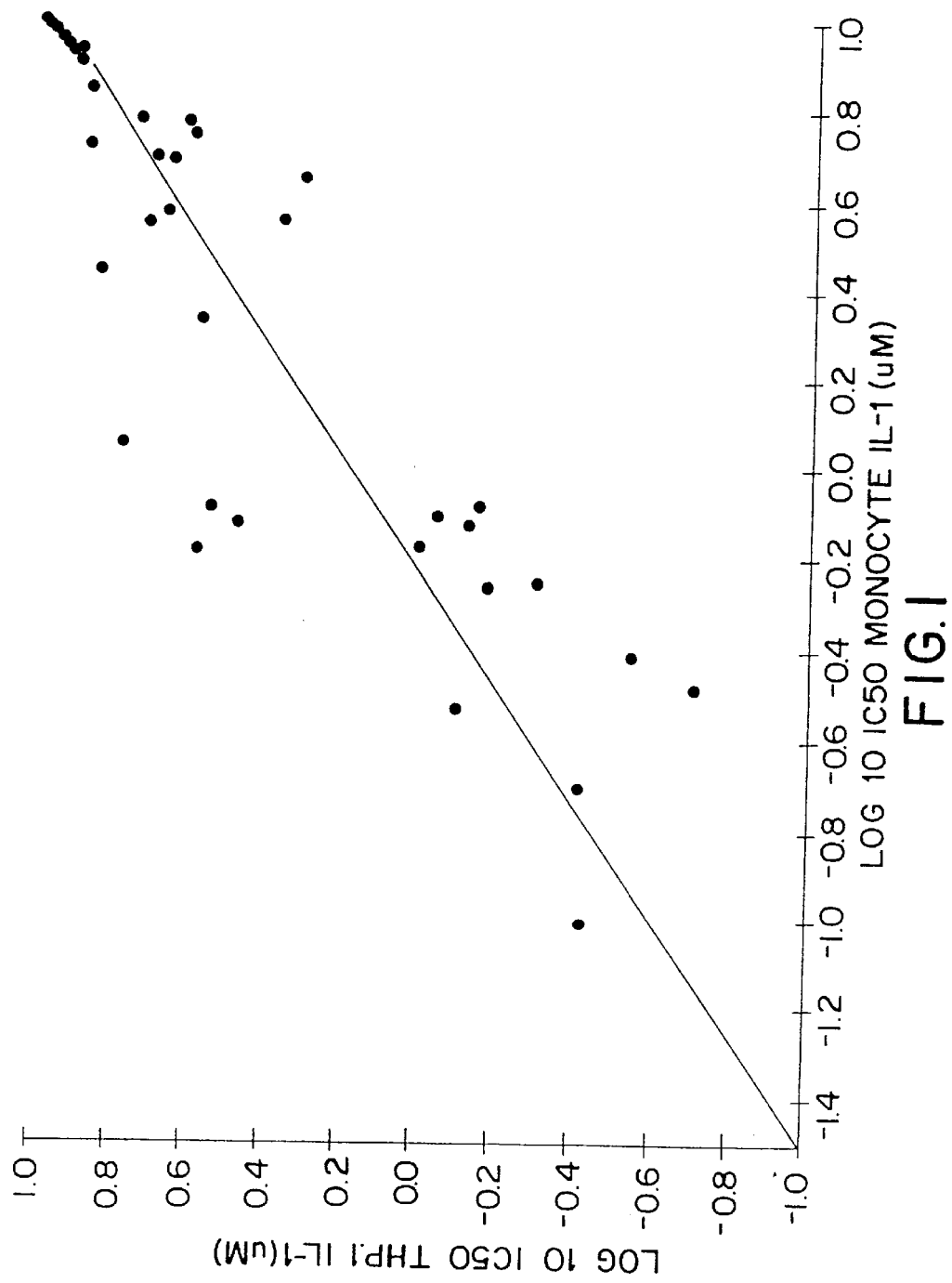
FIG. 1 illustrates the correlation of $IC_{50}$ of the pyridinyl imidazole CSAIDs for IL-1β biosynthesis in THP.1 cells and human monocytes. A Log-Log scatter plot of ~50 compounds with regard to their $IC_{50}$s for inhibiting IL-1 or TNF was generate Regression analysis was performed and the correlation coefficient is 0.881.

In further describing the present invention, the following additional terms will be employed, and are intended to be defined as indicated below.

An "antigen" refers to a molecule containing one or more epitopes that will stimulate a host's immune system to make a humoral and/or cellular antigen-specific response. The term is also used herein interchangeably with "immunogen."

The term "epitope" refers to the site on an antigen or hapten to which a specific antibody molecule binds. The term is also used herein interchangeably with "antigenic determinant" or "antigenic determinant site."

"Fusion protein" is a protein resulting from the expression of at least two operatively-linked heterologous coding sequences. The protein comprising a CSAIDs binding protein or fragment thereof and a second unrelated peptide sequence is an example of a fusion protein.

A coding sequence is "operably linked to" another coding sequence when RNA polymerase will transcribe the two coding sequences into a single mRNA, which is then translated into a single polypeptide having amino acids derived from both coding sequences. The coding sequences need not be contiguous to one another so long as the expressed sequence is ultimately processed to produce the desired protein.

"Recombinant" polypeptides refer to polypeptides produced by recombinant DNA techniques; i.e., produced from cells transformed by an exogenous DNA construct encoding the desired polypeptide. "Synthetic" polypeptides are those prepared by chemical synthesis.

A "replicon" is any genetic element (e.g., plasmid, chromosome, virus) that functions as an autonomous unit of DNA replication in vivo; i.e., capable of replication under its own control.

A "vector" is a replicon, such as a plasmid, phage, or cosmid, to which another DNA segment may be attached so as to bring about the replication of the attached segment.

A "double-stranded DNA molecule" refers to the polymeric form of deoxyribonucleotides (bases adenine, guanine, thymine, or cytosine) in a double-stranded helix, both relaxed and supercoiled. This term refers only to the primary and secondary structure of the molecule, and doe snot limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having the sequence homologous to the mRNA).

A DNA "coding sequence of" or a "nucleotide sequence encoding" a particular protein, is a DNA sequence which is transcribed and translated into a polypeptide when placed under the control of appropriate regulatory sequences.

A "promoter sequence" is a DNA regulatory region capable of binding RNA polymerase in a cell and initiating transcription of a downstream (3' direction) coding sequence. For purposes of defining the present invention, the promoter sequence is bound at the 3' terminus by a translation start codon (e.g., ATG) of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

DNA "control sequences" refers collectively to promoter sequences, ribosome binding sites, polyadenylation signals, transcription termination sequences, upstream regulatory domains, enhancers, and the like, which collectively provide for the expression (i.e., the transcription and translation) of a coding sequence in a host cell.

A control sequence "directs the expression" of a coding sequence in a cell when RNA polymerase will bind the promoter sequence and transcribe the coding sequence into mRNA, which is then translated into the polypeptide encoded by the coding sequence.

A "host cell" is a cell which has been transformed or transfected, or is capable of transformation or transfection by an exogenous DNA sequence.

A cell has been "transformed" by exogenous DNA when such exogenous DNA has been introduced inside the cell membrane. Exogenous DNA may or may not be integrated (covalently linked) into chromosomal DNA making up the genome of the cell. In prokaryotes and yeasts, for example, the exogenous DNA may be maintained on an episomal element, such as a plasmid. With respect to eukaryotic cells, a stably transformed or transfected cell is one in which the exogenous DNA has become integrated into the chromosome so that it is inherited by daughter cells through chromosome replication. This stability is demonstrated by the ability of the eukaryotic cell to establish cell lines or clones comprised of a population of daughter cell containing the exogenous DNA.

A "clone" is a population of cells derived from a single cell or common ancestor by mitosis. A "cell line" is a clone of a primary cell that is capable of stable growth in vitro for many generations.

Two DNA or polypeptide sequences are "substantially homologous" or "substantially the same" when at least about 85% (preferably at least about 90%, and most preferably at least about 95%) of the nucleotides or amino acids match over a defined length of the molecule. As used herein, substantially homologous also refers to sequences showing identity to the specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., "Current Protocols in Mol. Biol." Vol. I & II, Wiley Interscience, Ausbel, et al. (ed.) (1992). Protein sequences that are substantially the same can be identified by proteolytic digestion, gel electrophoresis and microsequencing.

The term "functionally equivalent" with respect to CSBP intends that the amino acid sequence of the subject protein is one that will display the CSAIDs binding activity disclosed herein.

A "heterologous" region of a DNA construct is an identifiable segment of DNA within or attached to another DNA molecule that is not found in association with the other molecule in nature. Thus, when the heterologous region encodes a receptor gene, the gene will usually be flanked by DNA that does not flank the gene in the genome of the source animal. Another example of a heterologous coding sequence is a construct where the coding sequence itself is not found in nature (e.g., synthetic sequences having codons different from the native gene). Allelic variation, alternative splicing or naturally occurring mutational events do not give rise to a heterologous region of DNA, as used herein.

Development of Molecular Reagents

Radioligand Synthesis

In order to isolate and purify the CSBP of this invention, it was first necessary to provide several labeled molecular reagents. The phenolic triaryl imidazole, Compound I, was chosen as an alternative radioligand because of its nanomolar potency and the relative ease of synthesis of the radiolabeled compound through catalytic reduction of the corresponding aryl bromide in the presence of tritium gas.

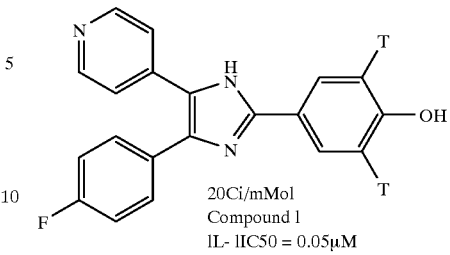

20Ci/mMol
Compound 1
IL-1IC50 = 0.05µM

Compound I was prepared according to the following reaction protocol:

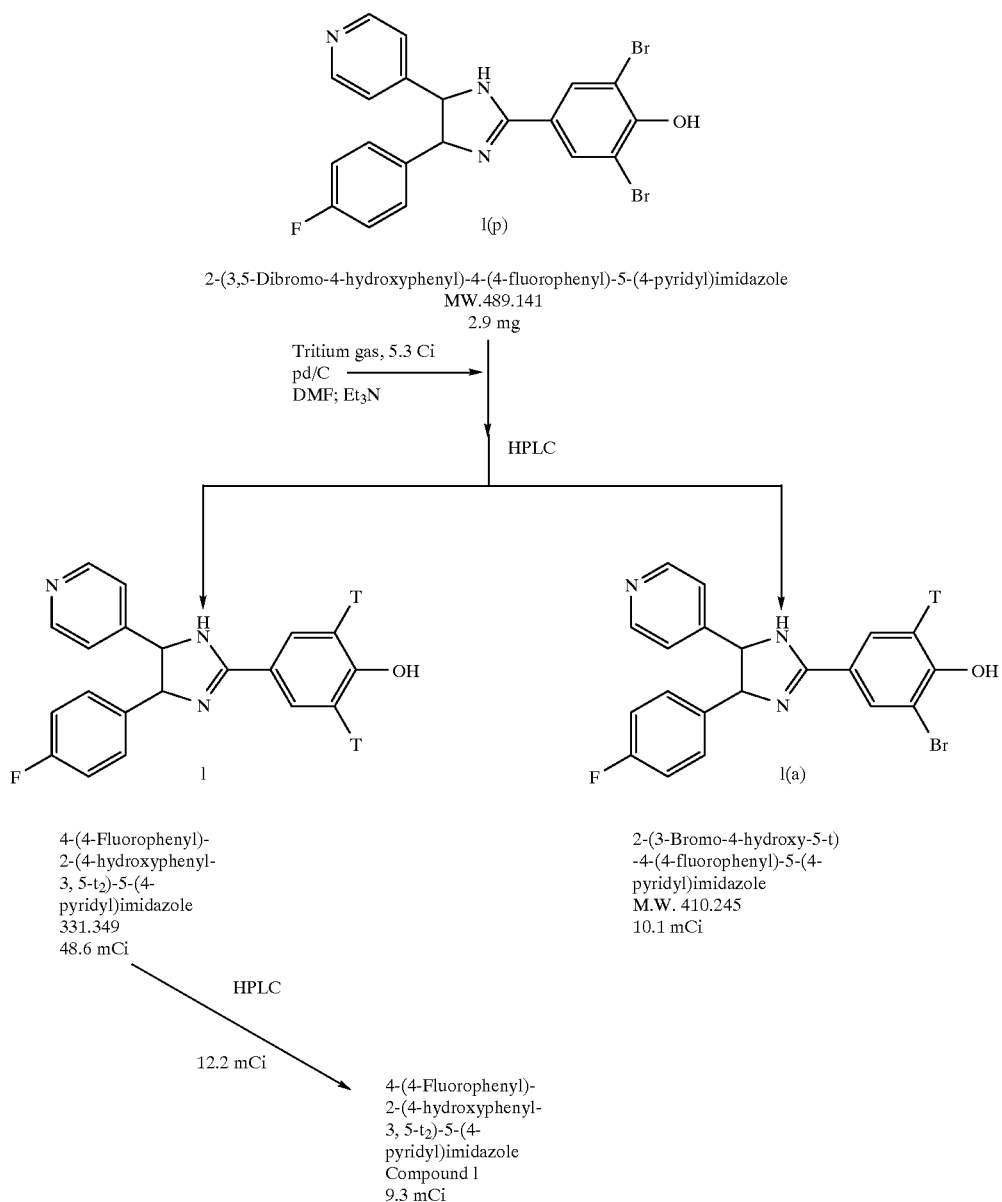

Preparation of 4-(Fluorophenyl)-2-(4-hydroxyphenyl-3,5-$t_2$)-5-(4-pyridyl) imidazole, (Compound I).

A 2.9 mg (0.0059 mmol) portion of 2(3,5-Dibromo-4-hydroxyphenyl)-4-(4-fluorophenyl)-5-(4-pyridyl) imidazole, Compound I(p), was dissolved in 0.95 mL of dry DMF and 0.05 mL of trimethylamine in a 2.4 mL round bottom flask equipped with a small magnetic stirring bar. A 1.7 mg portion of 5% Pd/C (Engelhard lot 28845) was added, and the flask was attached to the stainless steel tritium manifold. The mixture was degassed through four freeze-pump-thaw cycles, then tritium gas (5.3 Ci, 0.091 mmol) was introduced. The reaction mixture was allowed to warm to room temperature and was stirred vigorously for 20 h. The mixture was frozen in liquid nitrogen, the remaining tritium gas (2.4 Ci) was removed, and the flask was removed from the manifold. The reaction mixture was transferred, using 3×1 mL of methanol as rinsings, into a 10 mL round bottom flask, and the solvents were removed by static vacuum transfer. A 1.5 mL portion of methanol was added to the residue, then removed by static vacuum transfer. The latter process was repeated. Finally, the residue was suspended in 1.5 mL of ethanol and filtered through a syringe-tip Millipore filter (0.45 micron), along with 3×ca. 1 mL ethanol rinsings. The total filtrate volume was determined to be 3.9 mL, and the total radioactivity, 94.2 mCi. Solution was determined to be 3.9 mL, and the total radioactivity, 94.2 mCi. HPLC analysis of filtrate (Partisil 5 ODS-3, 4.6 mm I.D.×25 cm, 1 mL/min of 70:30:01 water/acetonitrile/trifluoroacetic acid, Radiomatic Flo-One Beta radio detector with 3 mL/min of Ecoscint-H cocktail through a 0.75 mL cell) showed the presence of Compound I ($R_t$=60 min. ca. 37% of total radioactivity), and a discrete intermediate presumed to be the monobromo derivative Compound Ia ($R_t$=11.8 min. ca. 9%).

The filtrate solution was evaporated to near dryness with a stream of nitrogen, and the residue was dissolved in about 1.2 mL of the HPLC mobile phase. The solution was separated by HPLC as shown below, and the peaks corresponding to Compounds I and Ia and SB collected separately.

| HPLC Method | |
| --- | --- |
| Column | Altex Ultrasphere 10 mm I.D. × 25 cm |
| Mobile Phase | 70:30:0.1 water/acetonitrile/trifluoroacetic acid |
| Flow Rate | 5 mL/min |
| UV detection | 210 nm |
| Injection Volumes | 0.05–0.4 m: |
| Retention Times | 7.8 min Compound I |
| | 24 min Compound Ia |

The pooled Compound I fractions totaled 32 mL in volume and the radioactive concentration was 1.52 mCi/mL (total 48.6 m Ci). The pooled SB Compound Ia [$^3$H] fractions (totaling 10.1 mCi) were evaporated to dryness and the residue was transferred quantitatively into a glass vial using 3.8 mL of absolute ethanol for further analysis.

An 8 mL (12.2 mCi) portion of Compound I was evaporated to dryness in vacuo at <35° C., then redissolved in 0.5 mL of mobile phase. The whole volume was injected into the HPLC system described above, and the appropriate peak was collected. Evaporation of the collected eluate in vacuo at <35° C. and transfer of the yellow residue into a vial with absolute ethanol provided a solution (3.8 mL, 2.44 mCi/mL) of Compound I. The portion of this solution used for NMR analyses was first evaporated to dryness using stream of nitrogen then taken up in $CD_3OD$.

Analysis of 4-(4-Fluorophenyl)-2-(4-hydroxyphenyl-3,5-$t_2$)-5-(4-pyridyl) imidazole, Compound I.

| Radiochemical Purity by HPLC | |
| --- | --- |
| Method | |
| Column | Ultrasphere Octyl, 5 µm, 4.6 mm I.D. × 25 cm, Beckman |
| Mobile Phase | 350:150:0.5(v/v/v) water/acetonitrile/trifluoroacetic acid |
| Flow Rate | 1.0 mL/min |
| Mass detection | UV at 210 nm |
| Radioactivity detection | Ramona-D radioactivity flow detector |
| Scintillator | Tru-Count (Tru-Lab Supply Co.) |
| Flow rate | 5.0 mL/min |
| Cell volume | 0.75 mL |
| Retention time | 7.7 min |
| Result | 98.7 |
| Radioactive Concentration by Scintillation Counting | |
| Method | |
| Scintillator | Ready Safe (Beckman Instruments, Inc.) |
| Instrument | TM Analytic model 6881 |
| Efficiency | Automated DPM calculation from quench curve |
| Result | 2.44 mCi/mL |
| Specific Activity by Mass Spectrometry | |
| Method | CI-MS, $NH_3$ reagent gas |
| Result | 20.0 Ci/mmol |
| | $^3$H Distribution: |
| | Unlabeled 44% |
| | Single Label 43% |
| | Double Label 13% |
| | $^3$H NMR[9] |
| Method | |
| Instrument | Brunker AM 400 |
| Experiment | Proton decoupled $^3$H NMR |
| | Proton non-decoupled $^3$H NMR |
| | Proton non-decoupled $^3$H NMR |
| Peak Referencing | Solvent Peak of methanol ∂3.3 |
| Solvent | Methanol-$d_4$ |
| Result | Tritium is incorporated exclusively on the carbon atoms ortho to aromatic hydroxyl group |

Analytical Summary

| Assay | Result |
| --- | --- |
| Radiochemical purity determined by HPLC | 98.7% |
| Radioactivity concentration determined by scintillation counting | 2.44 mCi/mL |
| Specific activity determined by mass spectrometry $^3$H NMR | 20.0 Ci/mmol agrees with the proposed structure |

Photoaffinity Radiolabeled Ligand

Additionally, a photoaffinity radiolabel was synthesized. Ideally, the radiophotoaffinity reagent should have a submicromolar binding affinity, a convenient site for the attachment of a radiolabel (preferable a gamma emitter) and allow for the positioning of the photoreactive group, (e.g. an azide) proximal to the binding site. The SAR leading to the proposal of Compound IV as the candidate for the photoaffinity reagent is illustrated in Table I below.

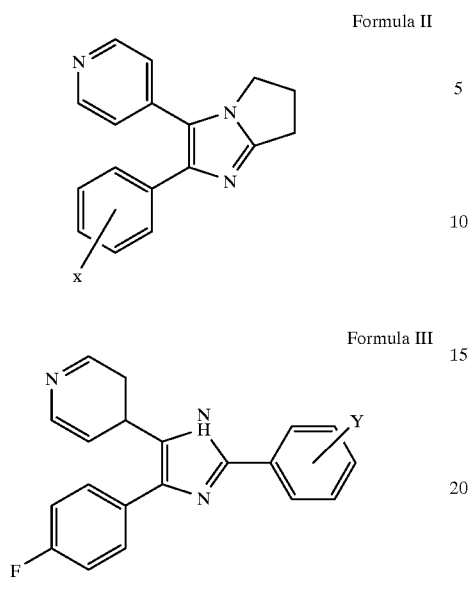

Formula II

Formula III

TABLE I

| Compound | X | Bio Assay IC$_{50}$, µM | Compound | Y | Bio Assay IC$_{50}$, µM |
|---|---|---|---|---|---|
| IIa | 4-F | >0.1 | IIIa | H | 0.15 |
| IIb | 4-H | 0.5 | IIIb | 4-N$_3$ | 0.05 |
| IIc | 4-Cl | 0.05 | IIIc | 3-I-4-NH$_2$ | 0.48 |
| IId | 3-Cl | 0.04 | IIId | 4-NH$_2$ | 0.28 |
| IIe | 2-Cl | 0.25 | | | |
| IIf | 4-I | 0.58 | | | |
| IIg | 3-I | 0.05 | | | |

In addition, a specific ELISA assay may also be usefully employed to determine IL-1β and TNFα levels (see: PCT Applications US93/00674 and US93/00675)

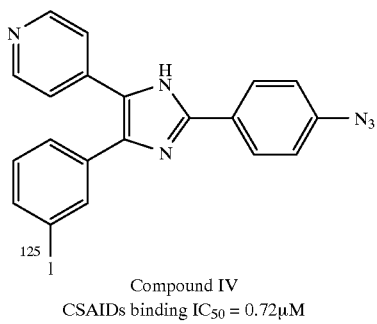

Compound IV
CSAIDs binding IC$_{50}$ = 0.72µM

The synthesis of radioiodinated photoaffinity label, Compound IV, employed a palladium-mediated stannylation of the aryl iodide and subsequent electrophilic radioiodination, according to the following protocol.

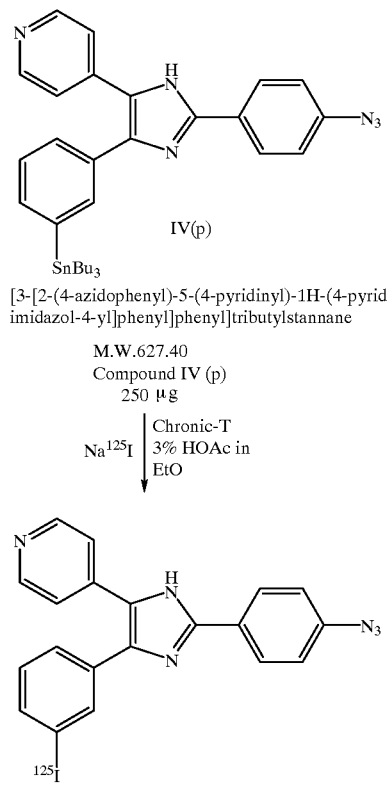

[3-[2-(4-azidophenyl)-5-(4-pyridinyl)-1H-(4-pyridimidazol-4-yl]phenyl]phenyl]tributylstannane M.W.627.40
Compound IV (p)
250 µg Na$^{125}$I | Chronic-T
3% HOAc in
EtO 4-[2-(4-azidophenyl)-5-(3-$^{125}$Iodo-phenyl)-1H-imidazol-4-yl]pyridine Compound IV
3.60 mCi Process Description Synthesis and purification of 4-[2-(4-azidophenyl)-5-(3-$^{125}$Iodo-phenyl)-1H-imidazol-4-yl]pyridine.

[3-[2-(4-Azidophenyl)-5-(4-pyridinyl)-1H imidazol-4-yl]phenyl]-tributylstannane, Compound IV (p) (250 µg, 0.398 µmol, was dissolved in 100 µL of 3% acetic acid in ethanol. To this solution was added 2.85 µg of chloramine-T hydrate (0.013 µmol) in 11.4 µL of water and 5.19 mCi of sodium [$^{125}$I]iodine in 45 µL of 0.1N sodium hydroxide. Another 50 µL of 3% acetic acid in ethanol was added to make the reaction mixture homogeneous. The reaction was stirred 60 minutes at room temperature (in the dark). The reaction was then blown to dryness under a stream of dry nitrogen and the residue partitioned between chloroform (1 mL) and saturated aqueous sodium bicarbonate (1 mL). The aqueous layer was extracted with chloroform (2×1 mL), the organic layers were combined and dried by passing through a pipet filled with granular sodium sulfate. The solvent was removed under stream of dry nitrogen; the residue was found to contain 4.36 mCi of iodine-125 (assayed on the Capintec dose calibrator). The aqueous layers were found to contain 310 µCi of iodine-125. The residue from the organic layer was taken up in 80 µL of HPLC mobile phase and purified on a Baker SiO$_2$ column, 5 µm, 4.6 mm I.D.×250 mm, eluted at 1.5 mL/min with 90:10:1 (v/v/v) hexane/isopropanol/triethylamine, with UV monitoring at 260 nm. The product fractions were combined and blown to dryness under a stream of dry nitrogen. The product was taken up in 3.0 mL of absolute ethanol. This procedure gave 3.60 mCi of Compound IV at a radiochemical purity of 99.0%, radioactive concentration of 1.20 mCi/mL and a specific activity of 1736 Ci/mmol.

Analysis of 4-[2-azidophenyl)-5-(3-iodo-$^{125}$I-phenyl)-1H-imidazol-4-yl]pyridine, Compound IV.

Radiochemical Purity by HPLC

Method

Column
Baker, Silica, 5 μm, 120A,
4.6 mm I.D.×25 cm.

Mobile Phase
90:10:1 (v/v/v)
hexane/isopropanol/triethylamine

Flow Rate
1.3 mL/min

Mass detection
UV at 260 nm

Radioactivity detection

Detector
β-RAM radioactivity flow detector

Scintillator
Tru-Count (Tru-Lab Supply Co.)

Flow rate
5.0 mL/min

Cell size
0.8 mL

Retention time
17.0 min

Result
99.0%

Mass Concentration by HPLC
Baker, Silica, 5 μm, 120A,

Method
4.6 mm I.D.×25 cm.

Column

Mobile Phase
90:10:1 (v/v/v)
hexane/isopropanol/triethylamine

Flow Rate
1.5 mL/min

Mass detection
UV at 260 nm

Retention time
11.2 min

Result
99.0%

Radioactive Concentration by Scintillation Counting—external standard method

Method

Solvent
Ready Safe (Beckman)

Instrument
TM Analytic model 6881

Efficiency
Automated DPM calculation from quench curve

Result
1.2 mCi/mL

Specific Activity Derived from Mass and Radioactive Concentrations
derived from mass and radioactive Method
concentrations Result
1736 Ci/mmol Analytical Summary

| Assay | Result |
| --- | --- |
| Radiochemical purity by HPLC | 99.0% |
| Massive concentration by HPLC | 0.32 μg/mL |
| Radioactive concentration | 1.2 mCi/mL |
| Specific activity derived from mass and radioactive concentrations | 1736 Ci/mmol |

The photoaffinity label has an $IC_{50}$ of 0.5–0.8 μM in a competitive binding assay and $IC_{50}$ of 3 μM in a CSAIDs bioassay.

CSAIDs Bioassay

The biological assay employed to evaluate CSAIDs activity was the IL-1 dependent EL-4/IL2 induction assay (Simon, P. L. et al., J. Immuno. Meth. 84: 85–94 (1985)). Briefly, Human monocytes were plated in 24-well plates in LPS-free RPMI 1640 media containing 1% human AB serum at a concentration of $10^6$ per milliliter per well and allowed to adhere for 1 h at 37° C.; non-adherent cells were removed by gentle washing. Test compounds or media were added to the cells 0 or 1 h before the addition of bacterial lipopolysaccharide (E. coli 001:B4; Difco, Detroit) at 10 ng/ml. The cultures were then incubated at various intervals as indicated at 37° C. in a humidified 5% $CO_2$ atmosphere. At the end of the incubation period, culture supernatants were collected. The residual adherent monocytes were lysed in a buffer containing 0.15M octyl-glucopyranoside, 25 mM Hepes, and 0.5 mM phenylmethylsulfonylfluoride in saline. Both supernatants and cell lysates were clarified by centrifugation and assayed for IL-1 activity.

IL-1 activity was measured by its ability to stimulate the secretion of IL-2 by EL-4 (ATCC TIB181) cells in the presence of A23187 ionophore. Serial dilutions of the samples were incubated with $10^5$ EL-4 cells in the presence of $2 \times 10^{-7}$M calcium ionophore A23187. After overnight incubation, 0.1 ml of a cell-free supernatant from each culture was taken and incubated with $10^4$ IL-2-dependent CTLL-20 (ATCC-TIB214) cells. Following an additional 20 hours of incubation, the cultures were pulsed with 1 μCi of tritiated thymidine for 4 h. The cells were then harvested onto glass-fibre filters and the radioactivity determined by liquid scintillation counting. All determinations of IL-1 activity were made in comparison to a standard.

CSAIDs Binding Assay

The next phase of the isolation and purification of CSBP required the development and validation of a cell-based CSAIDs binding assay. As mentioned above the early CSAID studies were conducted in human monocytes. A more convenient cell source, the human monocytic leukemia cell line, THP.1, (ATCC TIB 202) was selected and was shown to be an adequate surrogate cell source for mechanistic studies by virtue of its response to stimuli to produce IL-1 and TNF as well as a sensitivity towards CSAIDs comparable to human monocytes (FIG. 1).

Figure 2:
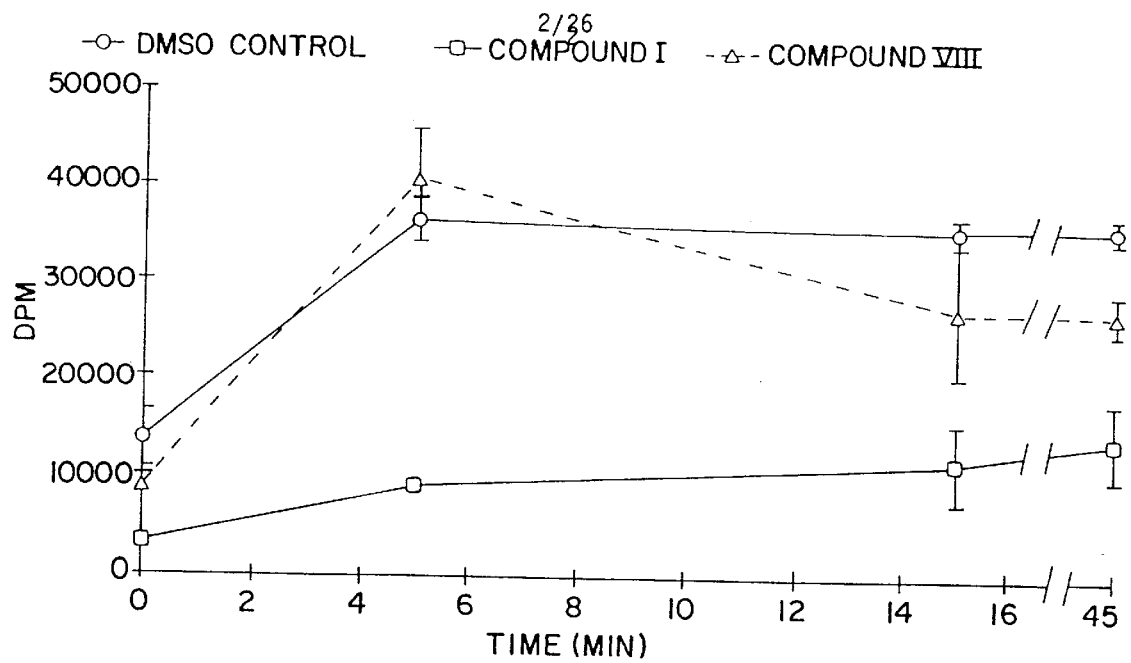
FIG. 2 illustrates the time dependent and reversible uptake of $^3$H-Compound I in intact THP.1 cells. 2 million THP.1 cells were incubated alone (appropriate solvent control) or with radiolabeled Compound I (50 nM) in the absence (0–0) or presence of excess non-radioactive ligand (50 μM) Compound I (square) and Compound VIII (triangle). At various intervals, the cells were centrifuged over a 8% sucrose cushion and the cell pellet was assessed for radioactivity by scintillation counting. Saturable binding was achieved at 15 minutes.

Radiolabeled Compound I was taken up by intact THP.1 cells in a time-dependent manner (FIG. 2). The uptake of the radiolabel was rapid and reached a maximum level at 3–5 minutes at 37° C. In addition, the uptake of radiolabel was saturable and specific.

Figure 3:
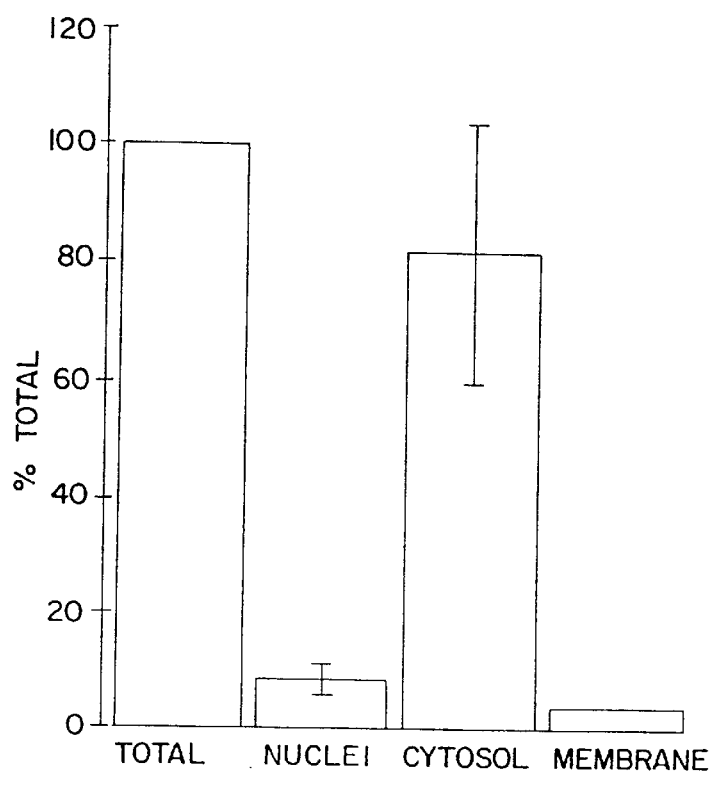
FIG. 3 illustrates the subcellular localization of binding activity. 10 million THP.1 cells were incubated with 50 nM radiolabeled Compound I for 30 minutes at 22° C. The cells were disrupted by dounce homogenization. The cell lysate was fractionated into nuclear, particulate and soluble fraction by differential centrifugation. The bulk of radioactivity was associated with the cytosolic fraction. An identical result was obtained in a binding assay using previously fractionated samples.

Upon subcellular fractionation of radiolabeled ligand loaded THP.1 cells, the predominant subcellular site of accumulation of the radioactivity was found to be the cytosol. (FIG. 3).

A specific and reproducible CSAID binding assay was developed using soluble cystosolic fraction from THP.1 cells and radiolabeled Compound I. In brief, THP.1 cytosol was routinely prepared from cell lysate obtained by nitrogen cavitation followed by a 10K×g low speed and a 100K×g high speed centrifugation, the supernatant of which was designated as the cytosolic fraction. THP.1 cytosol was incubated with appropriately diluted radioligand at room temperature for a pre-determined time to allow the binding to achieve equilibrium. The sample was added to a G-10 column and eluted with 20 mm TRN, 50 $\mu$M$\beta$-mercaptoethanol, $NaN_3$. The fraction encompassing the void volume was collected and the radioactivity was assessed by liquid scintillation counting. This was determined to reflect bound radioligand since the radioactive signal was abrogated by the presence of excess cold ligand in the incubation mixture or when there was no cytosolic fraction present.

More specifically, the CSAID Binding Assay is performed as follows:

Materials

Incubation buffer: 20 mM Tris, 1 mM $MgCl_2$, 20 $\mu$M Hepes, 0.02% $NaN_3$, store at 4° C. Elution buffer: 20 mM Tris, 50 $\mu$M 2-mercaptoethanol, $NaN_3$, store at 4° C.

G-10 Sephadex: add 100 g Sephadex G-10 (Pharmacia, Uppsala, Sweden) to 400 mL dd $H_2O$ and allow to swell at room temperature for 2 hours. Decant fines and wash 3 times. Add $NaN_3$ and QS with dd $H_2O$ to 500 mLs and store at 4° C.

Assemble Columns: Straw column, filter frit and tip (Konotes, SP 420160-000, 420162-002). Lowsorb tubes (Nunc) used in binding reaction. THP.1 cytosol spun at 15000 rpm for 5 min to clarify. THP.1 cytosol prepared by hypnotic treatment of cells and lysis by decompression in nitrogen. Nuclei and membrane fragments removed by differential centrifugation (10,000 g for 1 hour and 100,000 g for 1 hour).

Compounds: Non-radioactive Compound I with corresponding EtOH control (dilutions made in incubation buffer) and $^3$H-Compound I (dilutions in incubation buffer)

Method

A. Column Preparation

1. Begin 30 min before anticipated elution of reaction mixture.
2. Add 3 mL of G-10 slurry to column for bed vol of 1.5 ml.
3. Rinse with 7 mL elution buffer (fill to top of column)
4. Cut columns down to size.

B. Sample Incubation 1. 15 min incubation at 4° C.
2. Binding reaction mixture; 100 $\mu$L cytosol, 10 uL cold Compound I or EtOH control, 10 $\mu$L $^3$H-Compound I (molar concentration depends on nature of study).
3. "Free" control=100 $\mu$L incubation buffer in lieu of cytosol preparation.

C. Sample Elution

1. Elute at 4° C.
2. Add total reaction volume to G-10 column.
3. Add 400 $\mu$L elution buffer to column and discard eluate.
4. Add 500 $\mu$L elution buffer to column, collecting eluted volume in 20 ml scintillation vial.
5. Add 15 mL Ready Safe scintillation fluid.
6. Vortex and count in liquid scintillation counter for 5 minutes. Include a "total input counts control" (10 $\mu$L of labeled ligand).

D. Data Analysis

1. Plot DPMS as output in graphic form and analyze by regression analysis and "London ligand binding" software for the determination of IC 50 and Kd/Ki respectively.
2. Rank order the IC50s of the tested compounds in the CSAID bioassay and compare to that generated by the CSAID binding assay and establish a correlation curve.

Figure 4A:
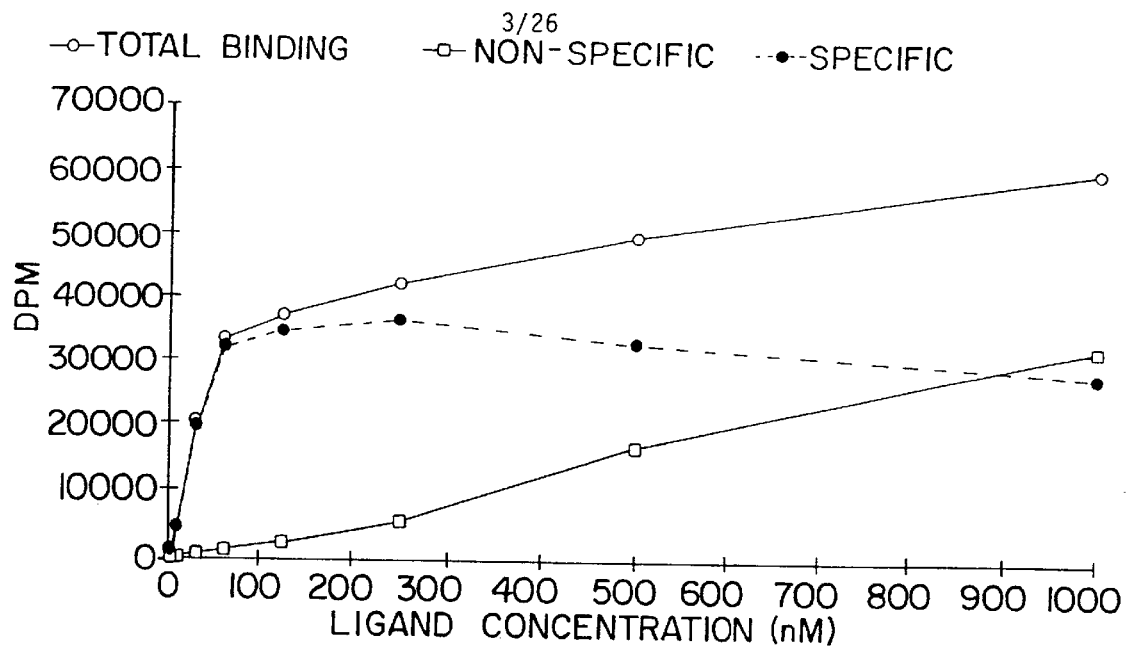
FIGS. 4A–4B illustrate the binding isotherm and Scatchard plot analysis of Compound I binding by THP.1 cytosol. Titration of radiolabeled Compound (0 to 1 μM) in the presence of constant excess cold ligand (50 μM) was performed in the binding assay using crude THP.1 cytosol. The specific binding is saturable. Scatchard plot analysis demonstrated a Kd of 3.6 nM, Bmax of 5 pmol/mg protein and a single site binding.
Figure 4B:
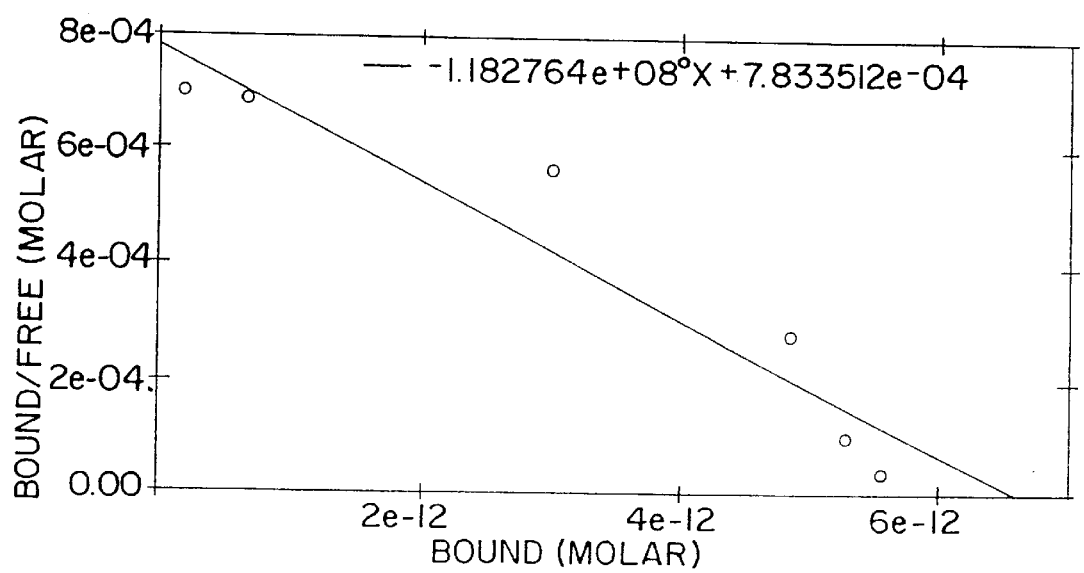

The binding assay was further validated by the following criteria:

THP.1 cytosol demonstrated saturable and specific binding of radiolabeled Compound I (FIG. 4).

Figure 5:
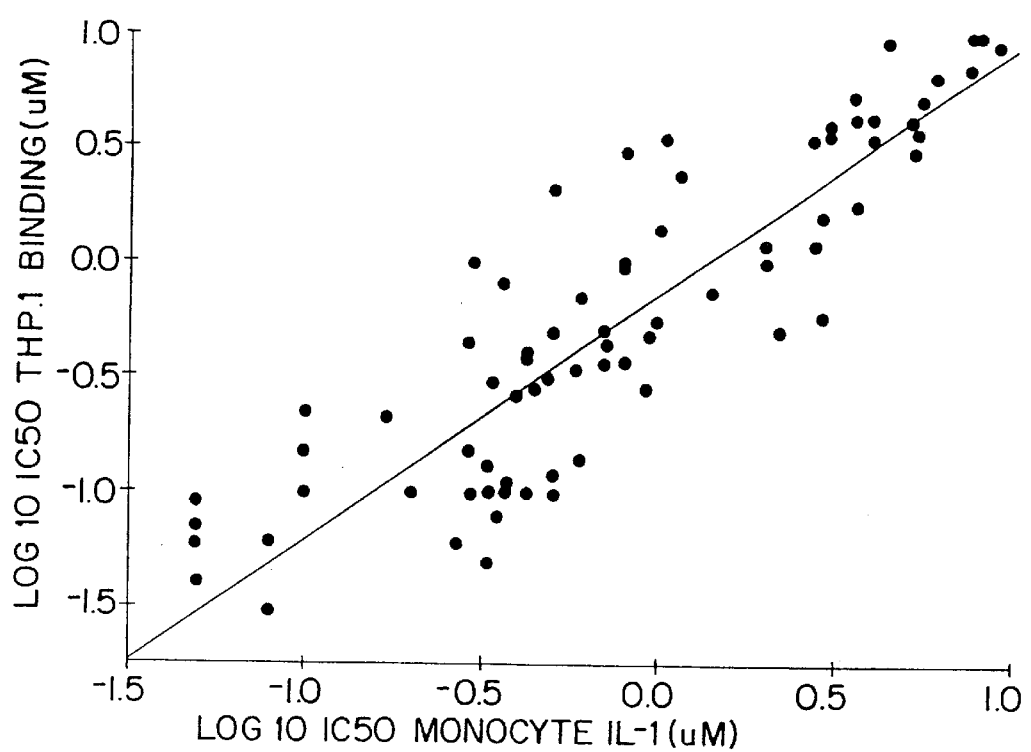
FIG. 5 illustrates the specificity of the CSAID binding activity. A large number of the pyridinyl imidazole compounds spanning three different structural classes with known $IC_{50}$s for cytokine synthesis inhibition were tested in a competitive binding assay in which radiolabeled Compound I was used. There was a high degree of correlation between the two activities (R=0.889) suggesting that the binding event is a necessary step in the inhibition of cytokine production.
Figure 6:
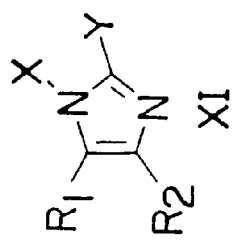
FIG. 6 illustrates the regioselectivity of the CSAIDs. Four pairs of regioisomeric forms of the CSAIDs were tested in the bioassay and the competitive binding assay. Only one isomeric form of the respective pair was active with identical $IC_{50}$s in both assays.

A substantial number of pyridinyl imidazole CSAIDs were tested in the radiolabel competitive binding assay. The rank order potency and the IC50s of the compounds was highly correlative to that determined by the human monocyte bioassay (FIG. 5). Furthermore, the competitive binding activity was regioselective (FIG. 6). These results underline the particular usefulness of the binding assay to the cytokine suppressive effects of these compounds and is considered particularly advantageous for SAR development and providing the means to help elucidate the molecular target.

Binding is highly specific for the pyridinyl imidazole CSAIDs. A series of non-structurally related compounds of varied pharmacological activities were tested in the competitive binding assay. They include the specific cyclooxygenase inhibitors, 5-lipoxygenase inhibitors, dual CO/LO inhibitors, PDE IV inhibitors, immunosuppressive macrolides, steroids, and others (Table II). None of the compounds tested at 100 $\mu$M demonstrated competitive binding.

A list of non-pyridinyl imidazole CSAIDs, related anti-inflammatory or immunosuppressive compounds tested in the competitive CSAID binding assay is provided in Table II. Unless otherwise indicated, no competitive binding was observed up to 100 $\mu$M.

TABLE II

| Cyclooxygenase Inhibitors | Steroid |
|---|---|
| • Indomethacin | • Dexamethasone |
| • Naproxen | |
| Selective 5-Lipoxygenase Inhibitors | Novel Anti-Inflammatories |
| • Hydroxyurea class | • IX270 |
| • Aminophenol class | • Tenidap (IC50 = 139 $\mu$M) |
| | • Romazarit |
| 5-Lipoxygenase Translocation Inhibitor | Peroxisome Proliferators |
| • MK886 | • Wyeth 14643 |
| | • Clofibrate |
| Dual Inhibitors | AH Receptor Agonists |
| • Phenidone | • 3-Methylcholanthrene |
| • NDGA (IC50 = 154 $\mu$M) | • $\beta$Naphthoflavone |
| Immunosuppressives | Miscellaneous |
| • FK506 | • Tibenelast |
| • Azaspirane | • Tetrandrine |
| • Rapamycin & Analogs | |
| PDE$_{IV}$ Inhibitor | |
| • Rolipram | |

Figure 7:
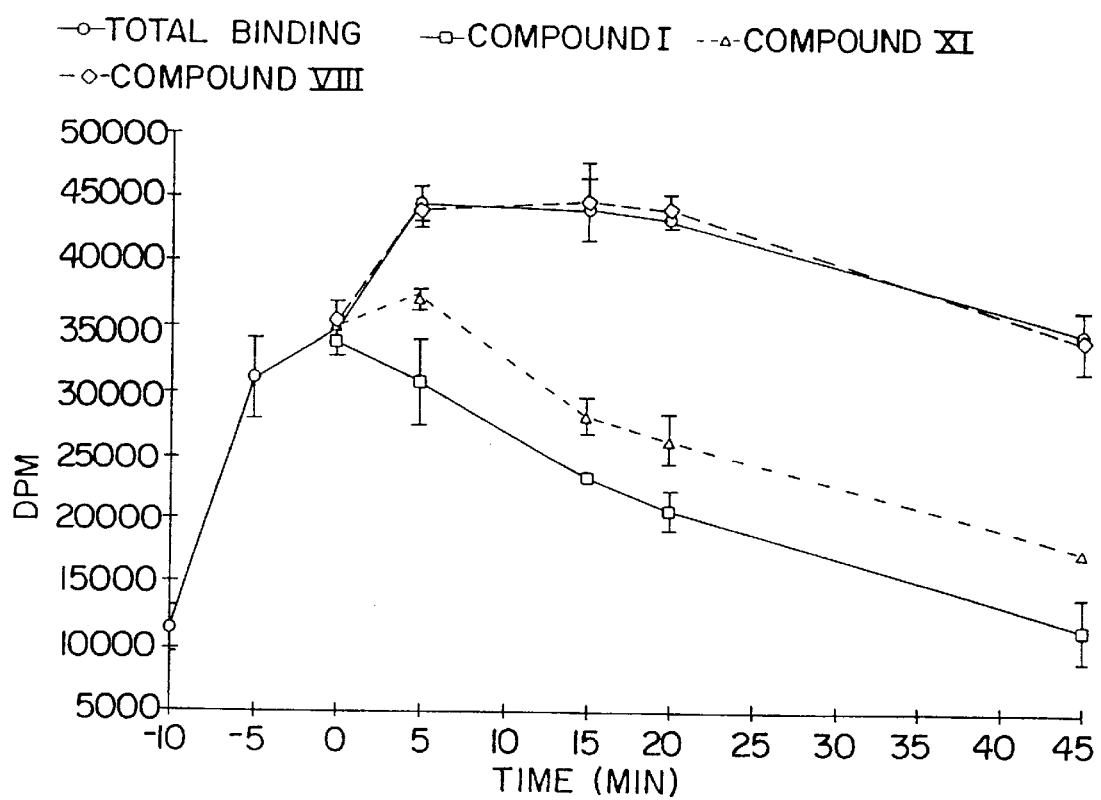
FIG. 7 illustrates that the binding of radiolabeled SB 202190 is saturable, specific and reversible. THP.1 cytosol was in cubated with 50 nM radiolabeled SB Compound I for 15 minutes to allow saturable binding to equilibrate, at which time 30 μM of the cold ligand was added and at various intervals, specific binding was determined. The binding is reversible with Compound VII and to a lesser extent, Compound XI and not at all with Compound VIII, the $IC_{50}$s of these compounds in the bioassay were 20 nM, 50 nM and >5 μM respectively.
Figure 8A:
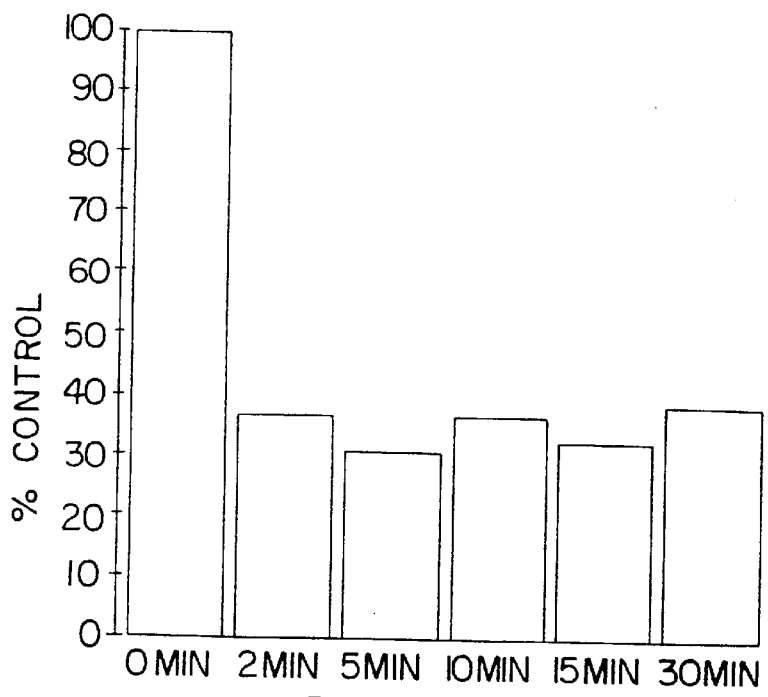
FIG. 8 illustrates the CSAID binding activity is protease and heat sensitive. THP.1 cytosol was subjected to trypsin (100 μg/ml) (Panel A) and heat (56° C.)(Panel B) treatment. Maximum abrogation of binding activity was achieved within 2 minutes after treatment with trypsin. The binding activity was abrogated after incubation at 56° C., showed a gradual loss at 37° C. and was relatively stable at 22° C. and 4° C.
Figure 8B:
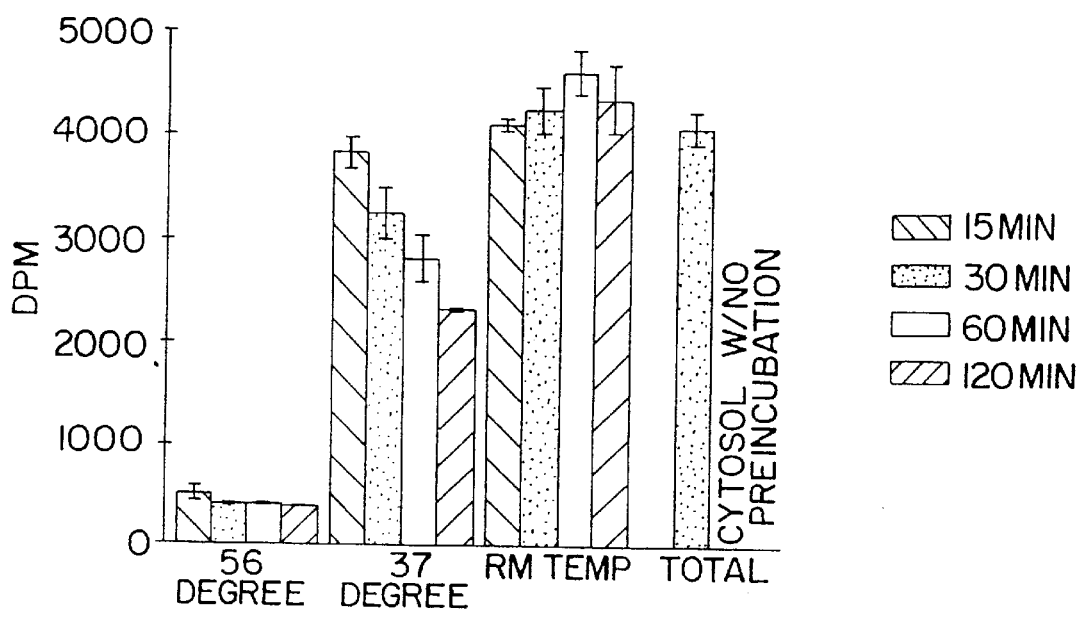

Having established a cell source and a binding assay, further characterization of CSBP established that the CSAID binding is saturable, specific and reversible (FIG. 7), follows a rapid on and off rate, the binding activity is sensitive to protease and heat treatment (FIG. 8) and is protein concentration dependent (data not shown).

The CSAID binding activity in human monocytes is indistinguishable from that determined for THP.1 by the criteria established for the binding activity listed above.

The binding is pH dependent with an optimal pH range from 5 to 8 and is independent of divalent cations and is sensitive to high salt concentration which is reversible.

Purification of CSBP

The purification of the CSBP from THP.1 cells was accomplished as follows:

Materials

The following compounds were synthesized by the methods outlined in PCT application, US93/00674 and US93/00675 both filed Jan. 13, 1993.

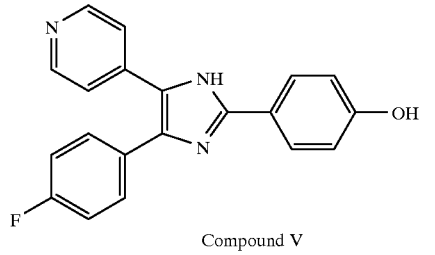

Compound V

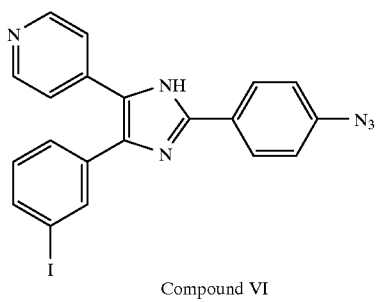

Compound VI

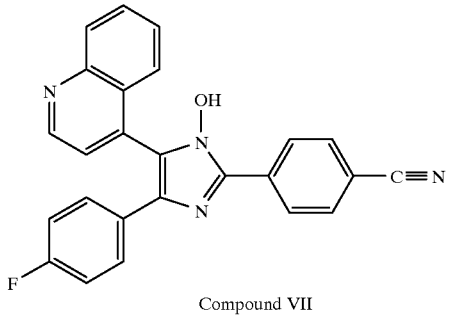

Compound VII

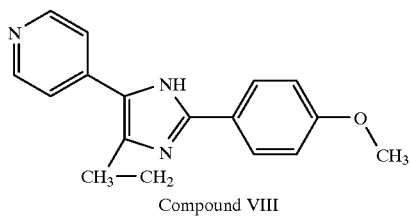

Compound VIII

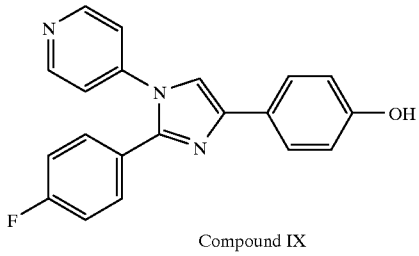

Compound IX

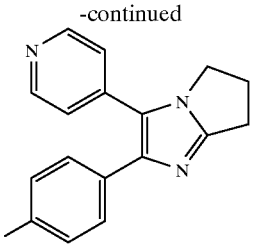

Compound X

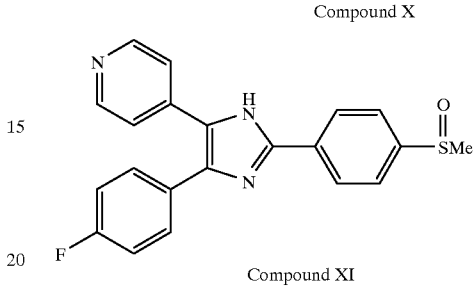

Compound XI

The radiolabeled compounds II and IV were prepared as described above. Polyclonal and monoclonal antibodies against actin (rabbit (cat #65-096) and mouse (cat. #69-100), respectively) were purchased from ICN Biomedicals. The peptide NH$_2$-Ile-Thr-Ala-Ala-Gln-Ala-Leu-Ala-His-Ala-Tyr-Phe-Ala-Gln-Tyr-Cys-COOH (Seq. I.D. No. 1) was synthesized by standard solid phase FMOC chemistry (see for example: Fields, G. B., et al. *Int'l. Peptide Protein Res.* 35: 161–214 (1990), purified and coupled to maleimide activated keyhole limpet hemocyanin (KLH) (Pierce Chemical Co. Cat #77105A) by conventional methods, and used to inoculate rabbits. All other chemicals were of reagent grade and unless otherwise specified, were not purchased from a particular vendor.

Growth of THP.1 Cells

THP.1 cells were grown and processed as follows:

THP.1 cells are grown in RPMI—1640 medium with 25 mM Hepes, 10% FBS (8% in reactors), 10 mM glutamine, and 0.05% pluronic F-68. The cells were passed on a ¾ days cycle with an average cell count of $2\times10^6$ (seeding density between $2\times10^5$ and $3\times10^5$). A high density cell recycle in shake flasks was used to scale-up the cells to the large reactors. In this process, the total volume of the shake flask was spun down and resuspended with the same volume of fresh medium. Therefore, seeding density increased with each passage, giving a higher density of cells per volume. The densities ranged from $6\times10^6$ to $12\times10^6$.

From the shake flasks, two scale-up procedures were used to obtain the required volumes. Initially, two 80L artisan reactors (60L working volume) were used. Every five days, 50L was taken out of both reactors and harvested. The cells were then fed with an additional 50L until the total required volume was reached. Alternatively, cells were grown in a 30L artisan and used to seed the 250L Abec reactor (totaling working volume was 150L). 120L was harvested every five days and the 30L left was refed. The seeding density was between $3\times10^5$ and $5\times10^5$. The pH for both types of reactors was controlled between 7.0 and 7.2. CO$_2$ was used as the controlling acid and sodium bicarbonate as the buffer. The D.O. was set at 30 percent for the Artisans reactors and 20 percent for the Abec reactor.

Preparation of THP.1 Cytosol

Cells were lysed by nitrogen cavitation in 20 mM TrisHCl pH 7.4, 1 mM MgCl$_2$, 1 mM PMSF, 1 μM pepstatin A and 1 μM leupeptin. Insoluble material was pelleted at 10,000×g for 10 min and the supernatant further clarified by a 100,000 ×g centrifugation for 1 h at 4° C. The supernatant from the final centrifugation was collected and is hereafter referred to as the THP.1 cytosol.

Measurement of CSAID Binding Activity

The same (typically 200 μg protein) was incubated with appropriately diluted $^3$H -Compound I (50 nM) at room temperature for 60 min to allow the binding to achieve equilibrium. Free ligand was separated from bound ligand on a 1.5 ml Sephadex G-10 column in 20 mM TrisHCl pH 7.4. The fraction encompassing the void volume was collected and the radioactivity was assessed by liquid scintillation counting. Protein concentrations were determined by the bicinchoninic acid assay (Pierce).

Superose 12 Chromatography

Approximately 100 to 250 ml of THP.1 cytosol was applied at 14.5 cm h$^{-1}$ to a 5L Superose 12 column (Pharmacia; 11.5×50 cm) equilibrated in 10 mM NaPO$_4$ pH 7.0 and 150 mM NaCl at 4° C. Fractions were collected (50 ml) and assayed for CSAID binding activity; a single peak of activity corresponding to an elution volume for a protein of $M_r$~50,000 was pooled (200 to 500 ml).

Hydroxylapatite Chromatography

The material from the Superose 12 column were applied at 30 cm h$^{-1}$ to a 160 ml Hydroxylapatite HA column (Cal. Biochem; 5.0×8.0 cm) equilibrated in 10 mM NaPO$_4$ pH 7.0 at room temperature. The column was eluted with a 10 to 200 mM NaPO$_4$ gradient over 2.5 column volumes. Fractions (30 ml) were collected and assayed for CSAIDs binding activity. A protein peak containing approximately 60% of the CSAID binding activity applied to the column was pooled (50 to 250 ml).

Radiophotoaffinity Labeling of CSBP

The following protocol was used for about 30 ml of sample but can be adapted for larger or smaller volumes. The hydroxylapatite pool was concentrated to about 30 ml using an Amicon stir cell (YM30 membrane, 70 psi N$_2$). Insoluble material in the concentrate was removed by centrifugation (10,000×g for 30 min in SS34 rotor at 4° C.). The supernatant (450 mg protein) was used in the labeling reactions, which were performed in 6-well microtiter plates (Nunc). Six reactions were carried out using the following reagents and protocol. Approx. 60 mg. of protein (4 ml) was added to 0.25 ml buffer (10 mM NaPO$_4$ pH 7.0, 150 mnM NaCl) and 0.25 ml 50 nM radioactive (i.e. "hot") $^{125}$I Compound IV (final concentration of 2.5 nM, 250 μCi) in dim light and allowed to stand on ice for 10 to 15 min. The microtiter plate was exposed to >300 nm light at a distance of 5 to 10 cm for 2 min while on ice. The reactions were chased with Compound IV (Compound VI being the "cold" (i.e. non-radioactive) form of Compound IV) as follows. A 1 mM stock of Compound VI was prepared by adding 0.3 ml 10 mM Compound VI to 2.7 ml 50% ethanol in 10 mM NaPO$_4$ pH 7.0 and 150 mM NaCl. Compound VI (0.5 ml 1 mM) was added to each labeling reaction in dim light and allowed to stand for 10 to 15 min on ice. The reactions were exposed to light as for the radioactive labeling. Unreacted Compounds IV and VI can be removed from labeled protein by the preparative isoelectric focusing or electrophoresis steps; or for samples of smaller volume, removed by gel filtration chromatography on Sephadex G-25 (1.6×12 cm) in 20 mM NaPO$_4$ pH 7.4 and 150 mM NaCl.

Analytical Electrophoresis. Autoradiography and Immunoblotting

Sodium dodecyl sulfate-polyacrylamide gel electrophoresis (SDS-PAGE) was performed under reducing conditions essentially as described by Smith B. J., *Meth. in Mol. Biol.*, Vol I, pp. 44–57 (1984). Samples were run on 0.75 mm thickness 16 cm (4% stacking, 10 or 12% separating) or 10 cm (12% pre-cast, Jule) stab gels using the Hoefer SE 600 or Mighty Small electrophoresis systems, respectively. Protein was stained by either coomassie blue R350 (Pharmacia) or silver (Silver Stain Plus, BioRad). Molecular weight protein standards were purchased from Amersham or Bio-Rad. For blotting, proteins were transferred to a polyvinylidene difluoride membrane (Millipore) in 192 mM glycine/25 mM Tri pH 8.3 and 20% (v/v) methanol using a Genie electrophoretic blotter (Idea Scientific) at 15 V. Protein labeled with $^{125}$I was visualized by autoradiography using Hyperfilm-MP (Amersham) after overnight exposures at –70° C. The membrane was blocked with 5% gelatin in 20 mM TrisHCl pH 7.5 and 500 mM NaCl before incubation with the appropriate antiserum diluted 1,000 to 5,000-fold in buffer. The antibody complexes were detected with anti-mouse or anti-rabbit immunoglobulin G (Amersham) coupled to horse radish peroxidase and visualized by luminol phosphorescence on Hyperfilm-ECL (Amersham).

Preparative Isoelectric Focusing

Preparative isoelectric focusing was performed using a Rainin RF3 recycling free flow focusing protein fractionator at 4° C. overnight, concentrated to about 3 ml with an Amicon stir cell (YM30 membrane, 70 psi N$_2$), and brought to 10% glycerol and 1% ampholyte (Pharmacia Ampholine or Pharmalyte pH 4 to 6) for a final volume of about 10 ml. Before the sample was applied to the RF$_3$, a 1% ampholyte/ 10% glycerol solution was pre-focused for 1 to 1.5 h (until the voltage, current, power and temperature were at baseline). The sample was injected into bubble port 14 using a needle and syringe. The system was allowed to equilibrate as for the pre-focusing before collecting 3 ml fractions. Labeled CSBP was identified by monitoring the radioactivity, and the appropriate fractions pooled.

Preparative SDS-Page

Preparative SDS-PAGE was performed using the BioRad Model 491 Preparative cell. The pooled fractions from the preparative isoelectric focusing were concentrated to 2 to 3 ml with an Amicon stir cell (YM30 membrane, 70 psi N$_2$). Approximately 2 to 2.5 ml of the concentrate was brought to about 3 ml in 100 mM Tris pH 6.8, 2% SDS, 100 mM 2-mercaptoethanol, 10% glycerol and 0.01% bromophenyl blue before incubating at 100° C. for 3 to 5 min. The sample was applied to the gel (2 cm 4% stacking gel, 6 cm 11% separating gel) and run at 40 mA in 192 mM glycine/25 mM Tris pH 8.3 and 0.1% SDS at room temperature. Fractions (2.5 ml) were collected and assayed for radioactivity in order to identify where labeled CSBP eluted from the gel.

Results

Partial Purification of CSBP

A typical partial purification of CSBP from THP.1 cytosol is summarized in Table III. As indicated, the recovery of activity is 20% and the level of purification is 3-fold. This was characteristic of CSBP recovery and purification during evaluation of a number of chromatography resins (anion and cation exchange, hydrophobic interaction with (NH$_4$)$_2$SO$_4$, blue sepharose, heparin sepharose, etc.); the purification scheme as listed in the Table III gave the best recovery and most reproducible results. Since attempts to purify CSBP further while following CSAID binding activity resulted in poor recovery of activity, this was as far as the purification was taken before photoaffinity labeling.

TABLE III

Purification of CSBP from THP.1 cytosol

| Sample | Activity, dpm[a] | Protein, mg | Specific Activity, dpm mg$^{-1}$ |
|---|---|---|---|
| THP.1 cytosol[b] | $5.0 \times 10^8$ | 6800 | $7.4 \times 10^4$ |
| Superose 12 | $1.6 \times 10^8$ | 1200 | $1.3 \times 10^5$ |
| Hydroxylapatite | $9.6 \times 10^7$ | 500 | $1.9 \times 10^5$ |

[a]activity is expressed as the $^3$H radioactivity (disintegration per minute, dpm) collected in the CSAID binding assayed as described above and corrected for the total sample.
[b]THP.1 cytosol was prepared from starting material equivalent to approximately $10^{11}$ cells.

Photoaffinity Labeling of CSBP

Figure 9:
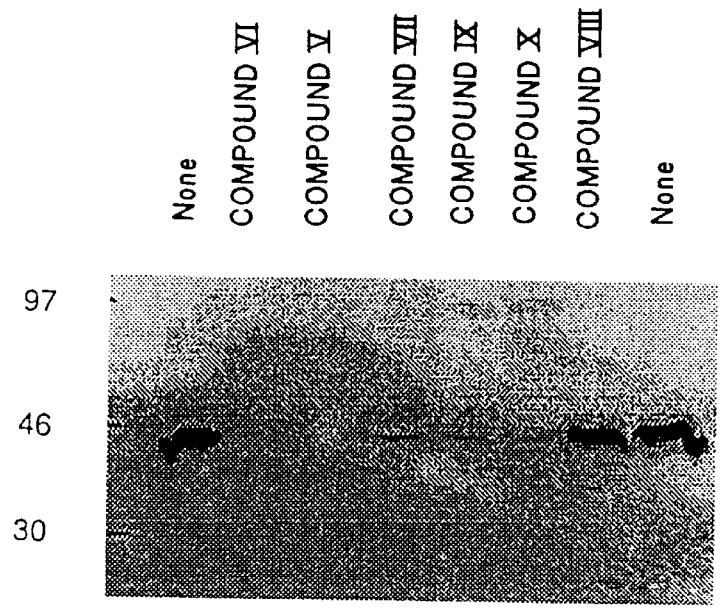
FIG. 9 illustrates the analysis of photoaffinity labeling of CSBP by SDS-PAGE and Autoradiography. Approximately 40 μg of protein was pre-incubated with the inhibitors listed above the gel at 10 μM before photoaffinity labeling with $^{125}$I Compound IV (2.5 nM). The reactions were analyzed by SDS-PAGE and autoradiography as described herein.

CSBP was covalently labeled with the $^{125}$I, aryl azide CSAID derivative Compound IV. The reaction was very specific as illustrated in FIG. 9, which shows that a single protein of $M_r$ 43,000 was labeled (the lanes labeled "None"). During the partial purification described above the CSAID binding activity eluted as a single peak from the Superose 12 gel filtration chromatography with a molecular weight corresponding to a protein of $M_r$ 45,000 to 50,000. Collectively, these two analyses indicate the CSBP is a single-chain, or "monomeric" protein of $M_r$ 43,000.

FIG. 9 also illustrates the specificity of the labeling. In the middle lanes of the gel, protein was preincubated with a non-radioactive CSAID (10 μM) before the photoaffinity labeling with $^{125}$I Compound IV (2.5 nM). The extent to which each CSAID competed with the photoaffinity label correlates well with its potency in a cellular assay. That is, the more potent the compound is in its ability to suppress IL-1 production in human monocytes, the more effectively it prevented photoaffinity labeling of the CSBP. Thus, CSBP is the protein labeled with Compound IV.

Purification of Labeled CSBP

Figure 10:
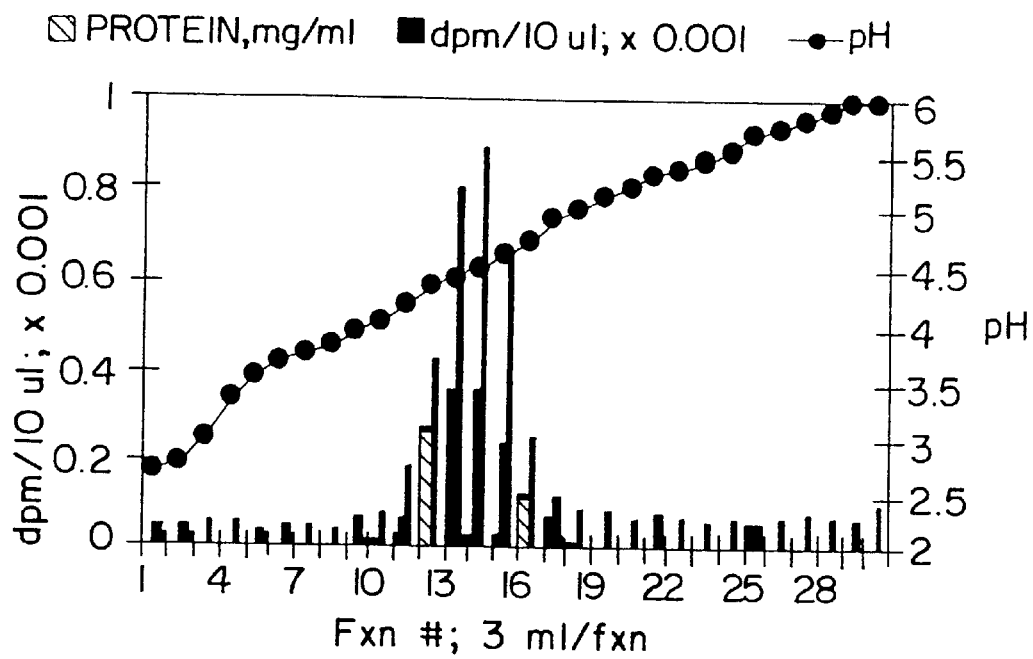
FIG. 10 illustrates that analysis of fractions from preparative isoelectric focusing. Protein labeled with $^{125}$I Compound IV was applied to the Rainin RF3 and analyzed as described herein.

In order to identify CSBP by its amino acid sequence, the labeled protein was further purified from the partially-purified CSBP used for photoaffinity labeling. The strategy to accomplish this was preparative isoelectric focusing, preparative SDS-PAGE and reversed-phase HPLC. The results of the preparative isoelectric focusing are shown in FIG. 10. The isoelectric point of the labeled protein corresponded to a pH of about 4.5. Western analysis indicated that some, but not all, of the actin was removed by this procedure. In addition, almost 70% of the protein applied eluted with the labeled protein (50% recovery of radioactivity). This was also demonstrated by SDS-PAGE and silver staining analysis (data not shown). Thus, for this application preparative isoelectric focusing did not provide a substantial purification of the desired protein.

Figure 11A:
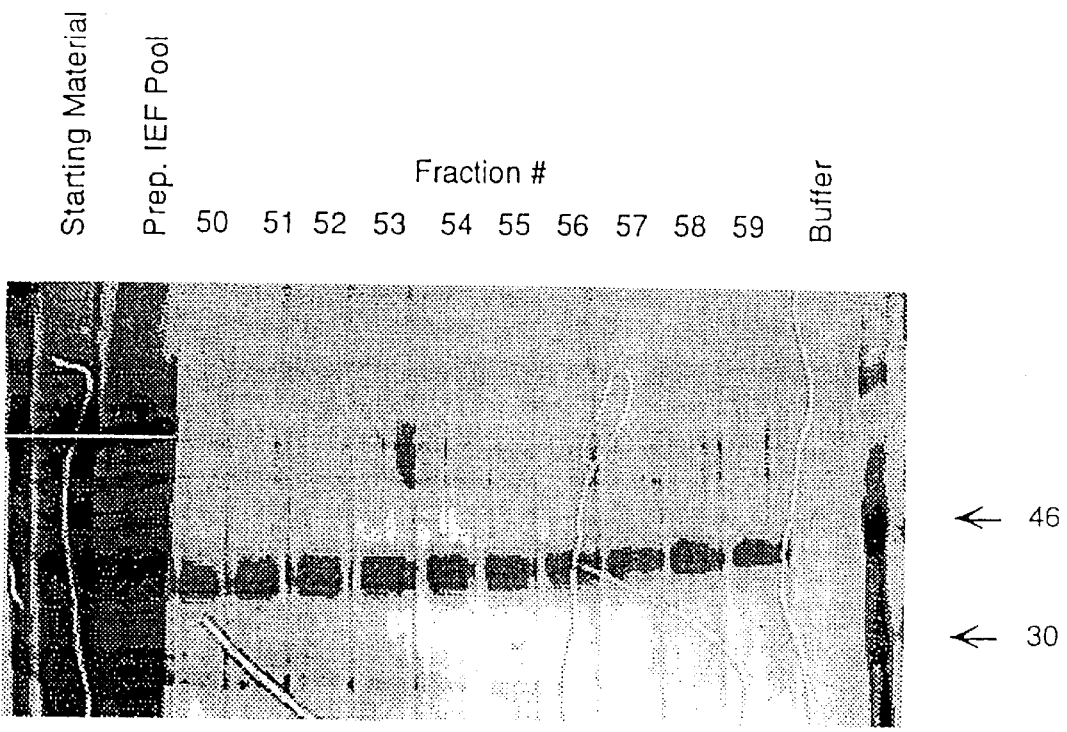
FIG. 11 illustrates the analysis of preparative SDS-PAGE fractions by (A) SDS-PAGE and Silver Staining, and (B) Radioactivity. Fractions were analyzed as described hereinbelow.
Figure 11B:
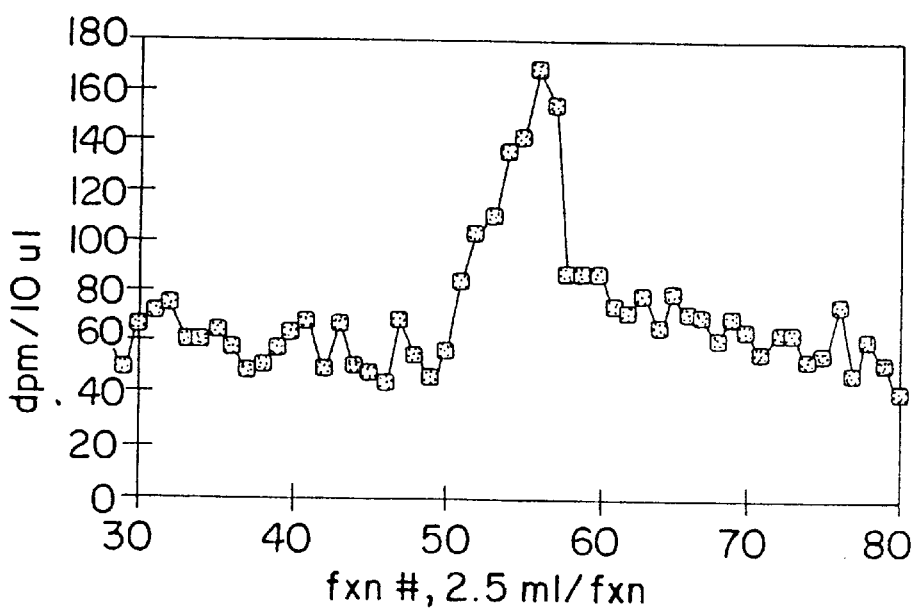

The most substantial purification of labeled CSBP was obtained by preparative SDS-PAGE. The material pooled from preparative isoelectric focusing was applied to a gel using the BioRad Model 491 Preparative Cell. As illustrated in FIG. 11, the radioactive fraction corresponding to a protein of about 43 kDa (fraction 56) has at least 90% of the non-radioactive protein removed by this procedure. In addition, unincorporated label is also removed.

Characterization of CSBP

Figure 12:
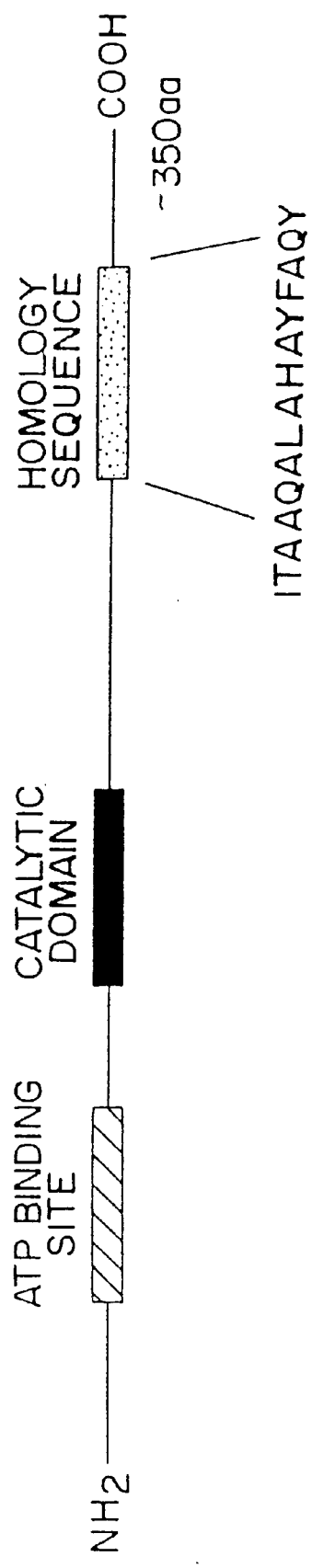
FIG. 12 illustrates the homology of unique amino acid sequence discovered during analysis of CSBP to MAP kinase. The peptide sequence (SEQ ID NO: 1) is listed below the linear representation of MAP kinase of the 15 residues; 9 identical (60%), 13 identical or homologous (87%).

After preparative SDS-PAGE, labeled CSBP was applied to reversed-phase HPLC, where a protein peak coeluting with the radioactivity was collected. Comparison of the protein concentration (determined by amino acid analysis) to the specific radioactivity of the sample demonstrated that only 10% of this protein was labeled (assuming a protein Mr of 43,000). N-terminal sequence analysis identified actin sequences corresponding to 30 to 40 amino acids downstream from the expected amino terminus. Internal sequence analysis following fragmentation with trypsin or CNBr generated approximately 90% actin sequences, but about 10% of the peptides gave unique sequences. One of the sequences from the tryptic digest had strong (85%) homology, but was not identical, to a C-terminal sequence found in a family of Ser/Thr protein kinases known as the mitogen-activated (MAP) kinases (FIG. 12; See also: Ray, L. B. & Sturgill, T. W., *Proc. Nat'l. Acad. Sci. (USA)*, 85:3753–3757 (1988)).

A peptide based on the sequence with homology to the MAP kinases was synthesized and used to inoculate rabbits for the production of antisera. Western analysis and autoradiography of labeled THP.1 cytosol 2-D gels demonstrated that 1) antibodies against actin or MAP kinases did recognize proteins on the blot, but not the radiolabeled protein; 2) the antibody prepared from the tryptic peptide recognized the radiolabeled protein. Thus, CSBP appears to have homology to, but is distinct from, the MAP kinases. Given the role of kinases in regulating translation (Pelech and Sanghera, *Science* 257:1355–66 (1992)) and the effect-of CSAIDs on IL-1 and TNF translation, a kinase is not inconsistent as the molecular target for CSAIDs.

Isolation and Characterization of the CSBP gene

This invention provides an isolated nucleic acid molecule encoding the human CSBP. Two amino-terminal peptide sequences were obtained from the protein fraction comigrating with the radioactive photoaffinity probe. One of these was derived from a trypsin digest of the radioactive protein fraction but was not itself radioactive, and had the sequence:

ILE THR ALA ALA GLN ALA LEU ALA HIS ALA TYR PHE ALA GLN TYR (Seq. I.D. No. 1)

The second was obtained from an 8 KDa cyanogen bromide fragment associated with radioactivity and had the sequence:

XXX (GLN) LEU LEU ASN ASN ILE (VALIPHE) LYS (PHE) GLN LYS LEU THR (Seq. I.D. No. 2)

where ( ) represents an uncertain assignment and / represents an uncertainty between two amino acids. XXX is an unknown amino acid. A search of Genbank indicated that peptide sequence I.D. No. 1 was homologous to the MAP kinase family of protein kinases, whereas peptide sequence I.D. No. 2 was unique. Based on these two sequences, two degenerate oligonucleotide DNA probes were synthesized using the genetic code to reverse translate the protein sequences, and tables of mammalian cell codon preferences (Grantham, R. et al., *Nucl. Acid Res.* 9: (1981)).

1. GCYCAYGCTAYTTYGCYCARTA (Seq. I.D. No. 3) and
2. AAYAAYATYKTBAARTTYCAAA (Seq. I.D. No. 4)

where Y=C or T
R=A or G
K=G or T
B=G, C or T

Hence the two mixed oligonucleotides consist of 128 and 384 unique sequences respectively. A cDNA library made from human monocytes treated with GM-CSF (Livi, G. P. et al., *Mol. Cell Biol.* 10: 2678–86 (1990)) in the commercial vector λZAP (Stratagene) which was screened at low stringency by hybridization to a 50:50 combination of the two synthetic oligonucleotide mixtures labeled with γ-32P ATP. Labeling of the oligonuleotides followed published methods (Current Protocols in Molecular Biology), typically labeling 3 μg of mixed oligonucleotide with 250 μCi γ-$^{32}$P ATP and using all of this in a 250 μl hybridization volume. The manufacturer's recommended conditions for plating and lifting phage were followed (see Stratagene λZAP protocol, Stratagene, La Jolla, Calif.) using the BB4 host strain. One additional step was to prewash the filterlifts at 65° C. in 2×SSPE/0.1%SDS twice for 30 min. prior to prehybridization to remove bacterial debris.

Subsequently, prehybridization and hybridization with the labeled oligonucleotide probes were performed at 37° C. for 24–7272 h in 6×SSPE, 5×Denhardt's solution, 0.1% SDS and 100 μg/ml phenol/chloroform extracted yeast tRNA. (20×SSPE is 3M NaCl, 0.2M NaH$_2$PO$_4$, 0.02M EDTA pH7.4.50×Denhardt's solution is 10 g polyvinylpyrrolidone (MW 40,000), 10 g Bovine serum albumin and 10 g Ficoll 400 per liter H$_2$O.

After hybridization the filters were washed twice under each of the following conditions.

1. 6×SSPE, 0.1% SDS, room temp, 10–15 min.
2. 6×SSPE, 0.1% SDS, 37° C., 10–15 min.
3. 3M tetramethylamnmonium chloride solution (500 g Me$_4$NCl, 1.38 liter H$_2$O, 73 ml 1M tris pH 8.0, 5.8 ml 0.5M EDTA, 7.3 ml; 20% SDS filtered through 0.45 μM filter), 37° C., 30 min (see: *Proc. Nat'l. Acad. Sci. USA* 82: 1585–1588 (1985) for a description of this technique).

Filters were exposed to Kodak film for 3–5 days in the presence of intensifying screens, and overlapping positives in duplicate filters picked and cycled through the same procedure until pure plaques obtained.

Phage was excised with M13 helper phage R408 in the recA⁻ *E. coli* host XL-1 blue according to manufacturers procedures (Stratagene).

After two subsequent rounds of replating and hybridization of positively hybridizing plaques using just the oligonuclcotide mixture #1, a single homogeneous phage was obtained which hybridized in a Southern blot with the oligonucleotide #1 (Seq. I.D. No. 3) but not with oligonucleotide #2 (Seq. I.D. No. 4). Sequencing of the DNA insert of this phage revealed an open reading frame at one end which encoded part of the No. 2 unique peptide sequence. I.D. No. 2 above. The amino sequence so encoded was:

Asn Ile Val Lys Cys Gln Lys Leu Thr. (Seq. I.D. No. 5).

The rest of the open reading frame (FIG. (13) Seq. I.D. No. 6 and 7 was homologous to several protein kinases including the cdc2 and the MAP kinase families. Based on this homology, it is predicted to be missing approximately 130 amino acids from the amino terminus which is obtained via a second round of library screening with the amino terminal region of the obtained cDNA clone.

The other end of the cDNA contains the poly A sequence corresponding to the 3' terminus of the MRNA from which it was obtained (FIG. 14, Seq. I.D. No. 8).

Accordingly, based on initial cDNA (FIG. 13), oligonucleotides (5'-CCTCGGAGAATTTGGTAGATAAGG-3' (Seq. I.D. No. 9) and 5'-AACA-TTGTGAAATGTCAGAAGCTTACAGATGACCAT-3' (Seq. I.D. No. 10)) were designed from the 5' end of the sense strand, and used to screen for cDNAs encoding the amino terminus of CSBP. The oligonucleotides were labelled at their 5' ends with polynucleotide kinase and γ-$^{32}$P-ATP. 10$^6$ plaques from a GM-CSF stimulated human monocyte library constructed in λZAP were screened on duplicate nitrocellulose filters which had been prewashed prior to hybridization in 2×SSPE, 0.1% SDS at 50° C. After blocking for 48 h with 50% formamide, 6×SSPE, 5×Denhardt's and 100 μg/ml sheared, denatured salmon sperm DNA, filters were hybridized in the same buffer with the above labelled oligonucleotides for 24 hours at 42° C. The filters were then washed twice with 2×SSPE, 0.1% SDS at room temperature, followed by two washes in 1×SSPE, 0.1% SDS at 42° C. and two washes in 0.5×SSPE, 0.1%

SDS at 42° C. before detection of hybridizing plaques by autoradiography. Positive plaques which appeared on duplicate filters were picked and replated and the procedure repeated twice until unique plaques could be isolated and phagernid DNA released according to manufacturer's protocol (Stratagene Cloning Systems, LaJolla, Calif.). The cDNAs were sequenced on an Applied Biosystems automated DNA sequencer (ABI 373A) using universal and specific oligonucleotide primers and Taq polymerase cycle sequencing, and the sequences merged and examined using Lasergene software on a Macintosh Ilci. Both strands were completely sequenced at least once in each cDNA clone.

Description of cDNAs

Figure 15:
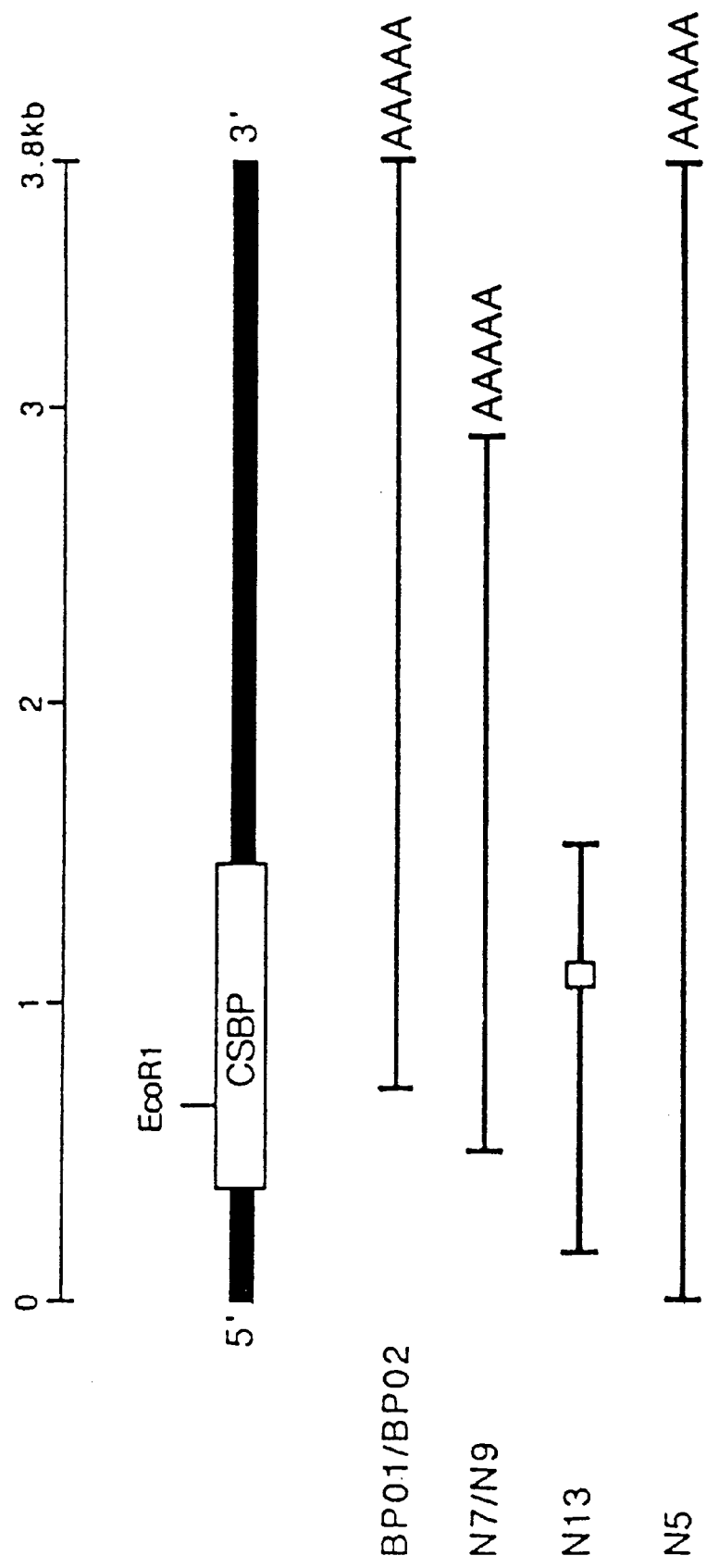
FIG. 15 illustrates diagramatically the various CSBP cDNAs described herein.

A summary of the cDNAs isolated is illustrated schematically in FIG. 15. There are four different cDNAs which have been completely sequenced and are identical in regions of overlap, with one exception to be described below. BP01/02 is the cDNA first isolated above, the partial sequence of which is given in FIGS. 13 and 14. The longest cDNA is 3.8 kb long (N5) Seq. I.D No. 11 (and SEQ ID NO: 12) and contains 370 nucleotides of 5' untranslated sequence, a 1.1 kb coding region and 2.4 kb of 3' untranslated sequence. The extreme 3' end is terminated by a poly A stretch characteristic of MRNA, and is preceded by the expected consensus sequence for polyadenylation. The N7 cDNA has a 3' untranslated region of only 1.4 kb terminating in a site and poly A run suggesting an alternative polyadenylation site. On a Northern blot a probe derived from the coding region hybridizes to an ca. 4.2 kb mRNA suggesting that the longest cDNA isolated is close to full length.

The coding translates into a protein of 360 amino acids with calculated molecular weight of 41.5 kDA, matching the size of the protein identified by photoaffinity crosslinking with $^{125}$I-labelled Compound IV (FIG. 16). The predicted isoelectric point (ca. 5.6) is also close to that observed (Ca. 5.0). Examination of the sequence indicates that it contains both the tryptic peptide sequence ITAAQ (boxed) (SEQ ID NO: 1) . . . and the cyanogen bromide sequence xxxLN-NIVK . . . (boxed) (SEQ ID NO: 14) obtained by sequencing of the CSAIDs binding protein in THP.1 cells. These sequences are preceded by the appropriate cleavage sites (arrows). The predicted size of the cynaogen bromide fragment (8 kDa) matches the size of the fragment which remains associated with the $^{125}$I-labelled radiophotoaffinity label [Compound IV] after cyanogen bromide treatment of the CSAIDs binding protein.

The N13 cDNA (FIG. 15) SEQ ID NO: 13 and SEQ ID NO: 14 is identical to the other three cDNAs with the exception of a 75 nucleotide region starting at position 1054 of the N5 cDNA. This difference results in a protein of identical size with amino acids 230–255 altered. (FIG. 17). The two different sequences are 43% identical at the nucleotide level, and 44% identical at the amino acid level. Without wishing to be bound by any particular theory, it is likely that the two variants result from alternative internal exon splicing, although allelic variation cannot be excluded. For ease of description, two proteins are referred to herein as CSBP1 (corresponding to the N5 cDNA) and CSBP2 (corresponding to the N13 cDNA).

Figure 18:
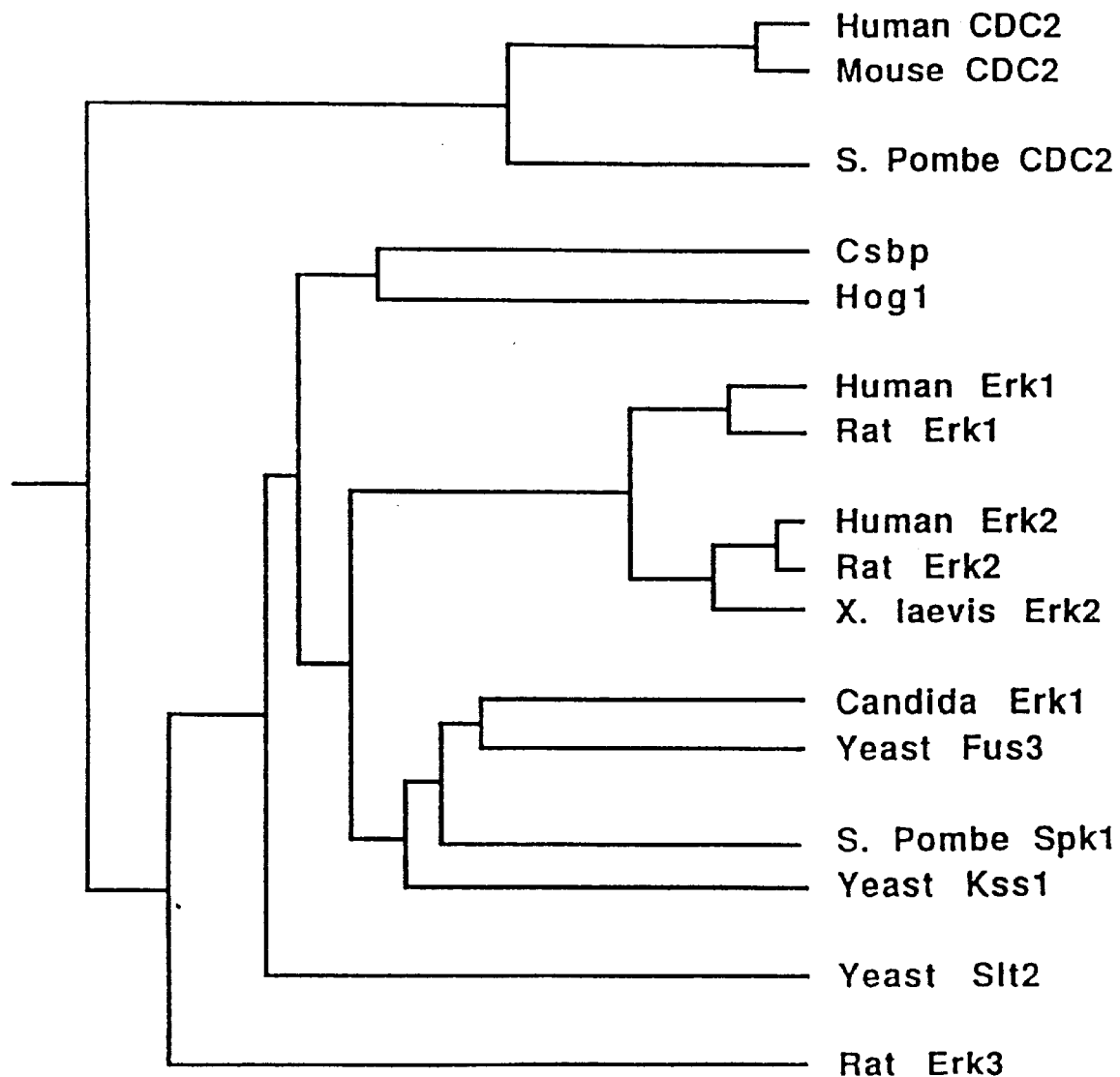
FIG. 18 illustrates a phylogenetic tree of various protein kinases.

Comparison of the CSBP sequence to proteins in the GenBank/EMBL or Swissprot databases indicated close homology to a family of proteins known as MAP (Mitogen Activated Protein) or erk (extracellular regulated) kinases (Boulton, et al., "Erks; A Family of Protein Serine-Threonine Kinases that are Activated and Tyrosine Phosphorylated in Response to Insulin and NGF", *Cell,* 65: 663–675 (1993). This family of protein kinases is conserved from yeast to man as indicated in the phylogenetic tree in FIG. 18 with the closest published homologue being the yeast HOG1 gene (Brewster et al., *Science* 259: 1760–63 (1993). An alignment of the CSBPs with selected members of this family (FIG. 19) shows a conservation of all 11 protein kinase motifs (I through XI), including residues identical in all protein kinases (bold) (Hanks et al., *Science*, 241: 42–52 (1988). Two boxed motifs in regions VI and VIHI indicate that the kinases phosphorylate serines and threonines I.D. Hence the CSBPs are protein kinases.

A threonine and tyrosine in a TxY sequence (asterisks) proximal to domain VIII are known to be regulatory phosphorylation sites for Erk 1 and Erk 2 (Payne, et al., *EMBO. J.*, 10: 885–892, 1991). These two residues are phosphorylated by MEK (MAPK or ERK Kinase) in response to various extracellular signals, resulting in an activation of the serine/threonine kinase activity of the MAP kinases (Kosako, et al., *EMBO. J.*, 12: 787–794 (1993). The conservation of these amino acids in the CSBPs suggests that they are also regulated by a MEK in response to extracellular stimuli such as LPS. These findings suggest that the CSBPs lie within a cascade of protein phosphorylation events which communicate cell surface stimuli to events such as translational regulation, within the cell. Much of the behavior of the CSBP in suitably stimulated cells can be predicted based on analogy with the known properties and behavior of the MAP kinases (Marshall, et al., *Curr. Opin. Genetics & Develop.*, 4: 82–89 (1994).

A multiple tissue Northern blot with a coding region cDNA probe suggests expression of CSBP MRNA in most tissues. A Southern blot at high stringency (0.1% SSPE, 0.1% SDS) suggested a single gene; however lower stringency washes may reveal closely related kinases. Gene mapping experiments using a panel of human/mouse hybrid cell lines available commercially indicated that the gene for CSBP resides on human chromosome 6.

Expression in *E. coli*

Figure 20:
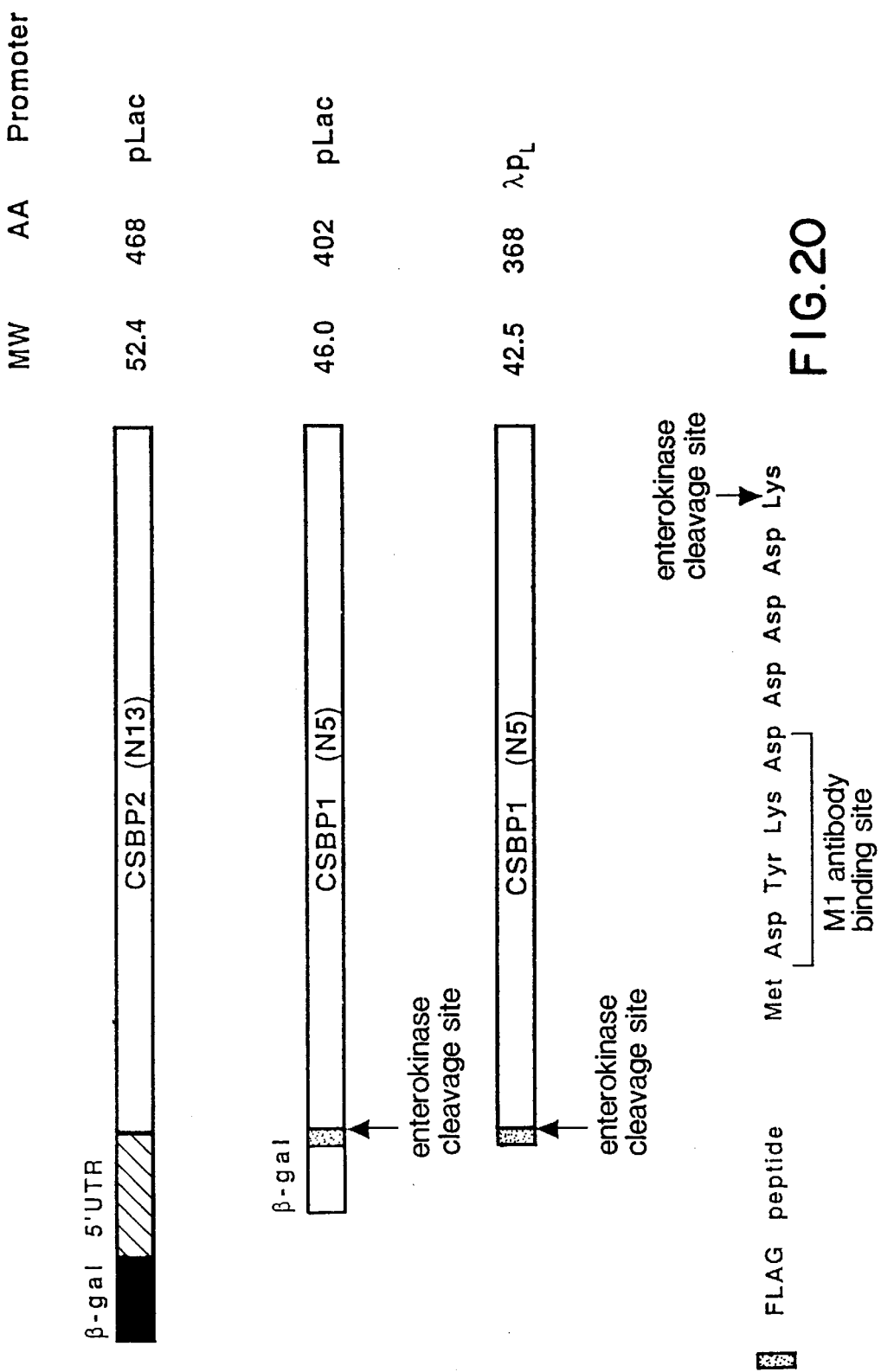
FIG. 20 illustrates the results of expression of CSBP in *E. coli*.

To confirm that the proteins encoded by the isolated cDNAs can bind to CSAIDs, the cDNAs were expressed in *E. coli* and yeast. In *E. coli* the CSBPs were expressed as fusion proteins with β-galactosidase and/or an enterokinase cleavable FLAG epitope tag (FIG. 20) (SEQ ID NO: 19) (FLAG is a commercial epitope for which reagents are available through IBI-Kodak). In the latter case this was achieved by the design of a synthetic oligonucleotide linker with an initiation site, antibody recognition sequence, and enterokinase cleavage site. Proteins were expressed under the control of either the pLac (e.g., Bluescript KS vector from Stratagene, LaJolla, Calif.) or λpL (Shatsman, et al., *N.Y. Acad. Sci.*, 478: 233–248 (1986)) promoters and the radiophotoaffinity probe [Compound IV] shown to specifically crosslink proteins of the expected sizes in cell lysates. Lysates also contain Compound IA specific binding activity. One can conclude that both CSBP1 and CSBP2 are the molecular targets of the CSAIDs within cells.

Protein expressed in *E. coli* was purified by passage over an affinity matrix containing a monoclonal antibody to the FLAG epitope according to manufacturer's instructions.

Expression in Yeast

An alternative system for expression of CSBP is *Saccharomyces cerevisiae*, not only for purification but also to assess function. The yeast HOG1 (High Osmolarity Glycerol response) gene, (Brewster et al., surpa) encodes a MAP kinase which is a close homologue of CSBP. Mutant hog1D strains show reduced growth on high-osmolarity medium and functional complementation of this phenotype with CSBP was tested.

CSBP2 was engineered for yeast expression as follows. A XhoI site was introduced at the initiation codon of CSBP2 by the polymerase chain reaction (Mullis, and Faloona, *Method in Enzymd.*, 155: 335–50 (1987) using the following oligonucleotide primers: 5'-cgccctcgagatgtctcaggagaggcccacg-3' SEQ ID NO: 15 and 3'-ctaagacctaaaacctgaccg-5', SEQ ID NO: 16. The 525-bp PCR fragment was digested with XhoI and BglII and subcloned into the same sites in p138NBU, a modification of p138NB (McHale et al., *Mol. Pharm.* 39: 109–113 (1991) in which the TRP1 selectable marker was replaced with URA 3. The resulting plasmid was then digested with BglII and SalI and ligated with a BglII XholI fragment containing the 3' end of CSBP2. The final construct contains partial 2 micron sequences for maintenance at high copy number, with CSBP2 rnRNA expression driven by the copper-inducible CUP1 promoter and terminated by the yeast CYC1 transcriptional terminator. Plasmid p138NBU-CSBPN13B was found encode the wild-type CSBP2 protein. Transformations of parent (YPH499 MATa ura3-52 lys2-801$^{am}$ ade2-101 trp1-D63 his3D200 leu2-D1) and hog1D (JBY10 [YPH499+hog1::TRP1]) strains (Brewster, et al., *J. Bacteriol.* 153: 163–168 (1983) Ura$^+$ prototrophs were isolated and grown to $^A$540 of 1.0 in synthetic complete medium lacking uracil (Hicks et al., *Genetics* 83: 245 (1976). CSBP2 expression was induced by the addition of 150 mM CuSO$_4$. Cells were harvested at 5 hr, resuspended 20 mM Tris-HC1 pH7, 1 mM MgCl$_2$, 1 mM phenylmethylsulfonylfluoride and disrupted by vortexing in the presence of 0.45 mm glass beads. Extracts were centrifuged at 1,500×g for 5 min at 4°.

Radiophotoaffinity probe (Compound IV) was shown to specifically crosslink a protein of the expected size in lysates of both p138NBU-CSBPN13A and p138NBU-CSBPN13B, which was not present in wild type or hog 1D strains containing control plasmid (p138NBU) and grown under similar conditions. Lysates also contained $^3$H Compound Ia specific binding activity. Therefore both CSBP1 (SEQ ID NO: 12) and CSBP2 (SEQ ID NO: 14) bind CSAIDS.

The proteins of this invention are preferably made by recombinant genetic engineering techniques. The isolated nucleic acids particularly the DNAs can be introduced into expression vectors by operatively linking the DNA to the necessary expression control regions (e.g. regulatory regions) required for gene expression. The vectors can be introduced into the appropriate host cells such as prokaryotic (e.g., bacterial), or eukaryotic (e.g., yeast or mammalian) cells by methods well known in the art (Ausubel et al.,supra) .The coding sequences for the desired proteins having been prepared or isolated, can be cloned into any suitable vector or replicon. Numerous cloning vectors are known to those of skill in the art, and the selection of an appropriate cloning vector is a matter of choice. Examples of recombinant DNA vectors for cloning and host cells which they can transform include the bacteriophage λ(*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (Bacillus), pIJ61 (Streptomyces), pUC6 (Streptomyces), YIp5 (Saccharomyces), a baculovirus insect cell system, , YCp19 (Saccharomyces). See, generally, "DNA Cloning": Vols. I & II, Glover et al., eds. IRL Press Oxford (1985) (1987) and; T. Maniatis et al. "Molecular Cloning", Cold Spring Harbor Laboratory (1982).

The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence may or may not contain a signal peptide or leader sequence. The subunit antigens of the present invention can be expressed using, for example, the *E. coli* tac promoter or the protein A gene (spa) promoter and signal sequence. Leader sequences can be removed by the bacterial host in post-translational processing. See, e.g., U.S. Pat. Nos. 4,431,739; 4,425,437; 4,338,397.

In addition to control sequences, it may be desirable to add regulatory sequences which allow for regulation of the expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

An expression vector is constructed so that the particular coding sequence is located in the vector with the appropriate regulatory sequences, the positioning and orientation of the coding sequence with respect to the control sequences being such that the coding sequence is transcribed under the "control" of the control sequences (i.e., RNA polymerase which binds to the DNA molecule at the control sequences transcribes the coding sequence). Modification of the sequences encoding the particular protein of interest may be desirable to achieve this end. For example, in some cases it may be necessary to modify the sequence so that it may be attached to the control sequences with the appropriate orientation; i.e., to maintain the reading frame. The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases, it may be desirable to add sequences which cause the secretion of the polypeptide from the host organism, with subsequent cleavage of the secretory signal. Alternatively, gene fusions may be created whereby the gene encoding the binding protein of interest is fused to a gene encoding a product with other desirable properties. For example, a fusion partner could provide known assayable activity (e.g. enzymatic) which could be used as an alternative means of selecting the binding protein. The fusion partner could be a structural element, such as a cell surface element such that the binding protein (a normally cytosolic component) could be displayed on the cell surface in the form of a fusion protein. It may also be desirable to produce mutants or analogs of the protein of interest. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis and the formation of fusion proteins, are well known to those skilled in the art. See, e.g., T. Maniatis et al., supra; *DNA Cloning*, Vols. I and II, supra; *Nucleic Acid Hybridization,* supra.

A number of prokaryotic expression vectors are known in the art. See, e, U.S. Pat. Nos. 4,578,355; 4,440,859; 4,436,815; 4,431,740; 4,431,739; 4,428,941; 4,425,437; 4,418,149; 4,411,994; 4,366,246; 4,342,832; see also U.K. Patent Applications GB 2,121,054; GB 2,008,123; GB 2,007,675; and European Patent Application 103,395. Yeast expression vectors are also known in the art. See, e.g., U.S. Pat. Nos. 4,446,235; 4,443,539; 4,430,428; see also European Patent Applications 103,409; 100,561; 96,491. pSV2neo (as described in *J. Mol. Appl. Genet.* 1:327–341) which uses the SV40 late promoter to drive expression in mammalian cells or pCDNA1neo, a vector derived from pCDNA1(*Mol. Cell Biol.* 7:4125–29) which uses the CMV promoter to drive expression. Both these latter two vectors can be employed for transient or stable(e.g. using G418 or hygromycin resistance) expression in mammalian cells. Insect cell expression systems, e.g., Drosophila, are also useful, see for example, PCT applications US 89/05155 and US 91/06838 as well as EP application 88/304093.3 and Baculovirus expression systems.

Depending on the expression system and host selected, the proteins of the present invention are produced by growing host cells transformed by an expression vector described above under conditions whereby the protein of interest is expressed. The protein is then isolated from the host cells and purified. If the expression system secretes the protein into growth media, the protein can be purified directly from the media. If the protein is not secreted, it is isolated from cell lysates or recovered from the cell membrane fraction. The selection of the appropriate growth conditions and recovery methods are within the skill of the art.

An alternative method to identify proteins of the present invention is by constructing gene libraries, using the resulting clones to transform *E. coli* and pooling and screening individual colonies using polyclonal serum or monoclonal antibodies to the desired binding protein.

The proteins of the present invention may also be produced by chemical synthesis such as solid phase peptide synthesis, using known amino acid sequences or amino acid sequences derived from the DNA sequence of the genes of interest. Such methods are known to those skilled in the art. Chemical synthesis of peptides is not particularly preferred.

The binding proteins of the present invention or their fragments comprising at least one epitope can be used to produce antibodies, both polyclonal and monoclonal. If polyclonal antibodies are desired, a selected mammal, (e.g., mouse, rabbit, goat, horse, etc.) is immunized with a binding protein of the present invention, or its fragment, or a mutated binding protein. Serum from the immunized animal is collected and treated according to known procedures. When serum containing polyclonal antibodies is used, the polyclonal antibodies can be purified by immunoaffinity chromatography or other known procedures.

Monoclonal antibodies to the proteins of the present invention, and to the fragments thereof, can also be readily produced by one skilled in the art. The general methodology for making monoclonal antibodies by using hybridoma technology is well known. Immortal antibody-producing cell lines can be created by cell fusion, and also by other techniques such as direct transformation of B lymphocytes with Ancogenic DNA, or transfection with Epstein-Barr virus. See, e a., M. Schreier et al., "Hybridoma Techniques" (1980); Hammerling et al., "Monoclonal Antibodies and T-cell Hybridomas" (1981); Kennett et al., "Monoclonal Antibodies" (1980); see also U.S. Pat. Nos. 4,341,761; 4,399,121; 4,427,783; 4,444,887; 4,452,570; 4,466,917; 4,472,500; 4,491,632; and 4,493,890. Panels of monoclonal antibodies produced against the protein of interest, or fragment thereof, can be screened for various properties; i.e., for isotype, epitope, affinity, etc. Alternatively, genes encoding the monoclonals of interest may be isolated from the hybridomas by PCR techniques known in the art and cloned and expressed in the appropriate vectors. Monoclonal antibodies are useful in purification, using immunoaffinity techniques, of the individual proteins against which they are directed. The antibodies of this invention, whether polyclonal or monoclonal have additional utility in that they may be employed reagents in immunoassays, RIA, ELISA, and the like. In addition they can be used to isolate the CSBP from human cells and determine the effect of different stimuli and compounds on the phosphorylation state and protein kinase activity of endogenous CSBP. The antibodies could be used to establish a tissue culture based assay for discovery or modification of novel compounds which block the phosphorylation or kinase activity of CSBP. An example of such an assay would be to incubate human monocytes or monocytic cell lines with a compound or compound mixture prior to treatment with LPS for a defined time period, followed by immunoprecipitation of CSBP with antibody and assessment of its phosphorylation state via immunoblot or chromatography or measurement of its kinase activity with appropriate protein or peptide substrate.

This invention provides a method for determining whether a ligand previously not known to bind to a CSBP can bind to such a protein. The method comprises contacting the ligand to be identified with cytosolic fraction from THP.1 cells and measuring its ability to compete with a known radioactive CSAID, as described above, in a CSAIDs binding assay. Alternative methods include contacting the ligand to be identified with a whole-cell expressing the coding sequence of a CSBP under conditions sufficient for binding of ligands previously identified as binding to such a receptor. In other embodiments cell membrane fractions comprising the CSBP fusions or isolated CSBP free or immobilized on solid supports may be used to measure binding of the ligand to be tested. When recombinant cells are used for purposes of expression of the CSBP it is preferred to use cells with little or no endogenous CSBP activity so that binding if any is due to the presence of the expressed protein of interest. As mentioned previously, a specifically designed indicator of receptor binding can be constructed. For example a fusion protein can be made by fusing the CSBP of this invention with a protein domain which is sensitive to CSBP/ligand binding. Such a domain referred to here as an indicator domain is capable, itself, or in association with accessory molecules, of generating an analytically detectable signal which is indicative of receptor ligand binding. A variation of this approach is to express CSBP as a fusion protein (e.g., fused to FLAG peptide) in THP.1 or other mammalian cells, and to use the fusion peptide as a means of isolating the recombinant CSBP after suitable stimulation and pretreatment of THP.1 cells. Such expression can be achieved with numerous mammalian expression vectors which utilize viral promoters, eg CMV, RSV and polyadenylation sequences, et. SV40, bovine growth hormone, and a selectable marker such as G418 or hygromycin for selection of stable transfectants.

Cytosolic preparations from transfected or transformed cells expressing such fusions may be employed. All of the above techniques that are useful for ligand identification are also useful in drug screening and drug development protocols.

Alternatively, the purified recombinant protein could be used to substitute for crude THP.1 cell lysates in a competitive binding assay with Compound Ia. This assay is useful to screen for novel compound which bind CSBP, or as a way to assess alterations to compound which is known to bind. The availability of purified protein allows alternative configurations of the assay from those described previously for the crude material. For example, if the protein is covalently linked to a tag, such a protein binding site for configuration in a colorimetic assay, e.g., conjugated antibody, or to an enzyme for direct detection of enzyme activity, e.g., horseradish peroxidase or alkaline phosphatase, binding to novel compounds displayed on a solid matrix could be detected. Such compounds could include low molecular weight organic molecules, peptides, peptoids, and proteins. In the latter case, the protein can be used as a way to isolate other proteins in its signaling cascade, for example, those that are in the pathway for activation of cytokine translation in activated monocytes. The protein may also be used to isolate naturally occurring regulatory molecules within mammalian cells that act by a CSAIDs binding mechanism. Finally, the protein can be used to identify target peptides displayed on the surface of phage.

The knowledge that the CSBPs encode protein kinases suggest that recombinant forms can be used to establish a protein kinase activity. Typically this would involve the direct incubation of CSBP with a protein or peptide substrate in the presence of $\gamma$-$^{32}$P-ATP, followed by the measurement of radioactivity incorporated into the substrate by separation and counting. Separation methods include immunoprecipitation, conjugation of substrate to a bead allowing separation by centrifugation or determination of incorporation by scintillation proximity assay, SDS-PAGE followed by autoradiography or biosensor analysis. While the specific substrates are not yet known, candidates include CSBP itself (autophosphorylation) and peptides related to known MAP kinase substrates. Other substances might be discovered by incubating CSBP with random peptides conjugated to solid supports or displayed by phage (see above) or by incubation of CSBP with mammalian cell lysates (e.g. THP.1 cell lysates) and $\gamma$-$^{32}$P-ATP, followed by separation of the labelled target proteins, and sequencing. Kinase activity may also be detected by use of antiphosphotyrosine antibodies. The protein kinase activity of CSBP may require incubation with a specific MEK. This may be achieved by preincubating CSBP with lysates from stimulated eukaryotic cells (e.g., LPS treated THP.1 cells) and ATP. Alternatively, it may be possible to isolate a more active form of CSBP from HOG1 deletion strains of yeast expressing the human CSBP and grown in high osmolarity conditions.

These assays permit the discovery and modification of compounds which inhibit CSBP kinase activity in vitro. Such compounds would be expected to block cytokine synthesis in a comparable fashion to the compounds described herein. They could also lead to the discovery of novel substrates which themselves may be viable targets for discovery of novel compounds which block cytokine production.

It is expected that CSBPs, like other MAP kinases, will be activated by a MEK, hence the recombinant protein would allow the establishment of a second assay which measures the ability of CSBP to be phosphorylated by putative MEKs. In this case fractions from stimulated cell lysates (eg THP.1 cells stimulated with LPS) are incubated with CSBP in the presence of $\gamma$-$^{32}$P-ATP, and the incorporation of $^{32}$P-label into CSBP measured by separation and counting. Separation can be achieved in a number of ways: one way is to use a CSBP fused to an peptide or protein and separate via affinity chromatography or immunoprecipitation with the peptide or protein directed antibody. Alternatively the CSBP can be directly conjugated to beads or bound through a fusion peptide or protein (e.g., FLAG (peptide), glutathionine-S-transferase) and separated by centrifugation after incubation with cell lysates. Also tyrosine phosphorylation of CSBP could be detected by immunoprecipitation or immunoblot with commercially available anti-phosphotyrosine antibodies.

These assays can be used to discover compounds which block the activation of CSBP protein kinase activity and to improve the potency of already discovered compounds. These compounds would be expected to have utility due to their blocking of cytokine synthesis. The assays are also useful to discover novel MEKs which themselves may become targets for novel compounds which would block cytokine synthesis.

The ability of human CSBP to rescue a HOGI deletion strain upon growth in conditions of high osmolarity allows for the direct screening of compounds which block CSBP activity in vivo. For example, compounds could be screened for their ability to block growth of a CSBP +/HOG1− yeast strain in high osmolarity but which have no effect on growth of the same strain in standard osmolarity or on a CSBP/ HOG1+ in high osmolarity. The sensitivity of the yeast based assay can be increased by introducing host mutations that affect the cell membrane and permeability (Gaber, et al., *Mol. Cell. Biol.* 9: 3447–3456. (1989).

In a compound screening embodiment of this invention, the CSBP in isolated, immobilized or cell bound form is contacted with a plurality of candidate molecules and those candidates are selected which bind to and interact with the protein. The binding or interaction can be measured directly by using radioactively labeled candidate of interest or indirectly by measuring an effect resulting from the interaction or binding of the candidate compound. Alternatively, the candidate compounds can be subjected to a competition screening assays, in which a known ligand, preferably labeled with an analytically detectable reagent, most notably radioactivity, is introduced with the compounds to be tested and the compound's capacity to inhibit or enhance the binding of the labeled ligand is measured. Compounds are screened for their increased affinity and selectivity for the CSBP.

To illustrate this aspect of the invention a natural product screen was performed.

The standard assay in which bound ligand is separated from free by exclusion chromatography using mini-columns was used to initiate a screening effort. Approximately 625 marine extracts, 202 microbial extracts and 233 extracts of plant material were tested for inhibition of $^3$H-Compound I binding to THP.1 cytosol. Two extracts were confirmed as antagonists of this binding, with $IC_{50}$'s of around 200 and 80 μg,/ml respectively. This low hit-rate (0.2%) coupled with the failure to observe inhibition by any of a selected group of "nuisance extracts" indicates that the assay is sufficiently selective and robust to support a screening effort. While the potency of these two hits is rather weak, they were nevertheless accepted as leads for isolation of their active principle so that the primary assay could be evaluated as well as identification of the bioactive compounds.

The two extracts were subsequently fractionated and characterized.

Further refinement of the binding assay to facilitate high throughout screening can be achieved by the minor modification of separating bound ligand from free ligand using spin columns.

This invention also contemplates pharmaceutical compositions comprising compounds when identified by the above methods and a pharmaceutically acceptable carrier. Pharmaceutical compositions of proteinaceous drugs of this invention are particularly useful for parenteral administration, i.e., subcutaneously, intramuscularly or intravenously. The compositions for parenteral administration will commonly comprise a solution of the compounds of the invention or a cocktail thereof dissolved in an acceptable carrier, preferably an aqueous carrier. A variety of aqueous carriers may be employed, e.g., water, buffered water, 0.4% saline, 0.3% glycine, and the like. These solutions are sterile and generally free of particulate matter. These solutions may be sterilized by conventional, well known sterilization techniques. The compositions may contain pharmaceutically acceptable auxiliary substances as required to approximate physiological conditions such as pH adjusting and buffering agents, etc. The concentration of the compound of the invention in such pharmaceutical formulation can very widely, i.e., from less than about 0.5%, usually at or at least about 1% to as much as 15 or 20% by weight and will be selected primarily based on fluid volumes, viscosities, etc., according to the particular mode of administration selected.

Thus, a pharmaceutical composition of the invention for intramuscular injection could be prepared to contain 1 mL sterile buffered water, and 50 mg of a compound of the invention. Similarly, a pharmaceutical composition of the invention for intravenous infusion could be made up to contain 250 ml of sterile Ringer's solution, and 150 mg of a compound of the invention. Actual methods for preparing parenterally administrable compositions are well known or will be apparent to those skilled in the art and are described in more detail in, for example, *Remington's Pharmaceutical Science,* 15th ed., Mack Publishing Company, Easton, Pa.

The compounds described herein can be lyophilized for storage and reconstituted in a suitable carrier prior to use. This technique has been shown to be effective with conventional proteins and art-known lyophilization and reconstitution techniques can be employed.

In situations where the identified drug is non-proteinaceous, it may be administered alone or in combination with pharmaceutically acceptable carriers. The proportion of which is determined by the solubility and chemical nature of the compound, chosen route of administration and standard pharmaceutical practice. For example, they may be administered orally in the form of tablets or capsules containing such excipients as starch, milk sugar, certain types of clay and so forth. They may be administered sublingually in the form of troches or lozenges in which the active ingredient is mixed with sugar and corn syrups, flavoring agents and dyes; and then dehydrated sufficiently to make it suitable for pressing into a solid form. They may be administered orally in the form of solutions which may be injected parenterally, that is, intramuscularly, intravenously or subcutaneously. For parenteral administration they may be used in the form of a sterile solution containing other solutes, for example, enough saline or glucose to make the solution isotonic.

The physician will determine the dosage of the present therapeutic agents which will be most suitable and it will vary with the form of administration and the particular compound chosen, and furthermore, it will vary with the particular patient under treatment. He will generally wish to initiate treatment with small dosages substantially less than the optimum dose of the compound and increase the dosage by small increments until the optimum effect under the circumstances is reached. It will generally be found that when the composition is administered orally, larger quantities of the active agent will be required to produce the same effect as a smaller quantity given parenterally. The compounds are useful in the same manner as other serotonergic agents and the dosage level is of the same order of magnitude as is generally employed with these other therapeutic agents. The therapeutic dosage will generally be from 1 to 10 milligrams per day and higher although it may be administered in several different dosage units. Tablets containing from 0.5 to 10 mg. of active agent are particularly useful.

Depending on the patient condition, the pharmaceutical composition of the invention can be administered for prophylactic and/or therapeutic treatments. In therapeutic application, compositions are administered to a patient already suffering from a disease in an amount sufficient to cure or at least partially arrest the disease and its complications. In prophylactic applications, compositions containing the present compounds or a cocktail thereof are administered to a patient not already in a disease state to enhance the patient's resistance.

Single or multiple administrations of the pharmaceutical compositions can be carried out with dose levels and pattern being selected by the treating physician. In any event, the pharmaceutical composition of the invention should provide a quantity of the compounds of the invention sufficient to effectively treat the patient.

The nucleic acid embodiment of this invention is particularly useful in providing probes capable of specific hybridization with human CSBP sequences. Probing technology is well known in the art and it is appreciated that the size of the probes can vary widely but it is preferred that the probe be at least 15 nucleotides in length. It is also appreciated that such probes can be and are preferably labeled with an analytically detectable reagent to facilitate identification of the probe. Useful reagents include but are not limited to radioactivity, fluorescent dyes or enzymes capable of catalyzing the formation of a detectable product. This invention contemplates, for example using receptor encoding probes in the diagnostic evaluation of disease states characterized by an abnormal, i.e. increased or decreased level of receptor gene expression. Alternatively, the probes can be used to identify individuals carrying chromosomal or molecular mutations in the gene encoding the receptor. Depending on the conditions employed by the ordinary skilled artisan, the probes can be used to identify and recover additional examples of this receptor (in its genomic or cDNA form) from other cell types and individuals. As a general rule the more stringent the hybridization conditions the more closely related genes will be that are recovered.

Also within the scope of this invention are antisense oligonucleotides predicated upon the sequences disclosed herein for the CSBP. Synthetic oligonucleotides or related antisense chemical structural analogs are designed to recognize and specifically bind to a target nucleic acid encoding the receptor gene and inhibit gene expression, e.g., the translation of the gene when the target nucleic acid is mRNA. Although not wishing to be bound to a particular theory for the mechanism of action of antisense drugs, it is believed that such drugs can act by one or more of the following mechanisms: by binding to MRNA and inducing degradation by endogenous nucleases such as RNase I or by inhibiting the translation of mRNA by inhibiting its binding to regulatory factors or ribosomal components necessary for productive protein synthesis. Additionally the antisense sequences can be use as components of a complex macromolecular arrays in which the sequences are combined with ribozyme sequences or reactive chemical groups and are used to specifically target mRNAs of interest and degrade or chemically modify said mRNAs. The general field of antisense technology is illustrated by the following disclosures which are incorporated herein by reference for purposes of background (Cohen, J. S., *Trends in Pharm. Sci.* 10:435 (1989) and Weintraub, H. M. *Scientific American* Jan.(1990) at page 40).

This invention also contemplates the use of the DNA sequences disclosed herein in gene therapy. Because CSBP is a protein kinase it is possible to make a site specific mutant which is inactive as a kinase but will block activation of the endogenous CSBP when coexpressed in the same cell, i.e., it is a dominant negative mutant (Kolch et al., *Nature* 349: 426–428 (1991). The DNA encoding this mutant protein could be used in gene therapy to reduce chronic inflammation. There are many vector and delivery systems available to direct DNA into target cells in vivo, e.g. adenovirus, retroviruses.

This invention also contemplates antibodies, monoclonal or polyclonal directed to epitopes corresponding to amino acid sequences disclosed herein from the CSBP. Particularly important regions of the receptor for immunological purposes are those regions associated with ligand binding domains of the protein. Antibodies directed to the regions are particularly useful in diagnostic and therapeutic applications because of their effect upon protein-ligand interaction. Methods for the production of polyclonal and monoclonal antibodies are well known, see for example Chap. 11 of Ausubel et al. (supra).

This invention also provides pharmaceutical compositions comprising an effective amount of antibody or fragment thereof directed against the CSBP to block binding of the naturally occurring ligands to that protein in order to treat or ameliorate disease states associated with protein activation.

Transgenic, non-human, animals may be obtained by transfecting appropriate fertilized eggs or embryos of a host with nucleic acids encoding the CSBP disclosed herein, see for example U.S. Pat. Nos. 4,736,866; 5,175,385; 5,175,384 and 5,175,386. The resultant transgenic animal may be used as a model for the study of CSBP/ligand interaction. Particularly, useful transgenic animals are those which display a detectable phenotype associated with the expression of the protein. Drugs may then be screened for their ability to reverse or exacerbate the relevant phenotype. This invention also contemplates operatively linking the CSBP coding gene to regulatory elements which are differentially responsive to various temperature or metabolic conditions, thereby effectively turning on or off the phenotypic expression in response to those conditions.

The nucleic acid probes disclosed herein can be used to clone the cognate version of the human CSBP gene from a desired experimental animal species; for example the murine version. Strains of mice can be developed in which said gene has been eliminated by conventional gene knock-out technology. The gene can then be substituted/or replaced by the human CSBP DNA of this invention to yield a mouse for screening candidate drugs in vivo. Similar gene knockout and human protein inhibition studies can also be performed with yeast.

The purified protein of this invention is also useful in a reagent for structural studies with and without bound drug candidates as a means for the rational design of novel drugs affecting CSBP. For example, the recombinant protein may be used to derive the structure of the protein alone or complexed with Compound Ia and related compounds through X-ray crystallography, NMR or modelling from published structures of related protein kinases, e.g., CSK. A structure fosters an understanding of how the inhibitory compounds bind, and can lead to the design or discovery of further compounds which can block CSBP activity and hence be inhibitors of cytokine synthesis. There are now several examples of such structure-based design for other protein targets, e.g., HIV protease. Given the similarity of CSBP to several other kinases (e.g. the MAP and CDC kinases), such structural information will be useful in designing novel compounds which inhibit other members of the kinase family.

What is claimed is:

1. An isolated polynucleotide encoding a cytokine suppressive antiinflammatory drug binding protein (CSBP) comprising a polynucleotide encoding a protein comprising an amino acid sequence selected from the group consisting of: SEQ ID NO: 12 and SEQ ID NO: 14, conservative substitution variants thereof and naturally occurring allelic variants thereof, said variants being further characterized as having kinase activity.

2. The isolated polynucleotide as claimed in claim 1, wherein said isolated polynucleotide is DNA or RNA.

3. An isolated polynucleotide comprising a polynucleotide encoding a protein comprising an amino acid sequence selected from the group consisting of SEQ ID NO: 12 and SEQ ID NO: 14, said protein being further characterized as having kinase activity.

4. The isolated polynucleotide as claimed in claim 3, wherein said isolated polynucleotide is DNA or RNA.

5. An isolated polynucleotide comprising a polynucleotide encoding a protein comprising an amino acid sequence selected from the group consisting of: SEQ ID NO: 1, conservative substitution variants thereof and naturally occurring allelic variants thereof said variants being further characterized as having kinase activity.

6. The isolated polynucleotide as claimed in claim 5, wherein said isolated polynucleotide is DNA or RNA.

7. An isolated polypeptide which is a CSBP comprising amino acids 227–261 of SEQ ID NO: 12.

8. An isolated polypeptide which is a CSBP comprising amino acids 262–304 of SEQ ID NO: 12.

9. An isolated polypeptide which is a CSBP comprising amino acids 262–304 of SEQ ID NO: 14.

10. An isolated polynucleotide comprising a polynucleotide encoding a protein consisting of an amino acid sequence selected from the group consisting of SEQ ID NO: 12 and SEQ ID NO: 14, said protein being further characterized as having kinase activity.

11. An isolated polynucleotide comprising a polynucleotide encoding a protein comprising the amino acid sequence set forth in SEQ ID NO: 1.

12. The isolated polynucleotide as claimed in claim 11 wherein said isolated polynucleotide is DNA or RNA.

13. An isolated polynucleotide comprising a polynucleotide encoding a protein consisting of the amino acid sequence set forth in SEQ ID NO: 1.

14. An expression vector comprising a nucleic acid molecule encoding a CSBP polypeptide, said polypeptide comprising an amino acid sequence selected from the group consisting of: SEQ ID NO: 12 and SEQ ID NO: 14 when said expression vector is present in a compatible host cell.

15. The expression vector as claimed in claim 14, wherein said nucleic acid molecule is RNA.

16. The expression vector as claimed in claim 14, wherein said nucleic acid molecule is DNA.

17. A host cell comprising the expression vector of claim 16.

18. A process for producing a recombinant host cell comprising the step of transforming or transfecting a cell with the expression vector of claim 16, such that the host cell, under appropriate culture conditions, produces a polypeptide comprising an amino acid sequence selected from the group consisting of: SEQ ID NO: 12 and SEQ ID NO: 14.

19. A recombinant host cell produced by the process of claim 18.

20. A process of producing a protein with the host cell of claim 19, wherein said host cell is cultured under appropriate culture conditions such that said polypeptide is produced.

21. A process of producing a polypeptide with the host cell of claim 20, wherein said polypeptide is selected from the group consisting of: SEQ ID NO: 12 and SEQ ID NO: 14.

22. An isolated polynucleotide comprising a polynucleotide sequence selected from the group consisting of: SEQ ID NO: 11 and SEQ ID NO: 13.

23. An isolated polynucleotide consisting of a polynucleotide sequence selected from the group consisting of: SEQ ID NO: 11 and SEQ ID NO: 13.

24. The isolated polynucleotide of claim 23, wherein said polynucleotide sequence comprises nucleotides 363–1442 of SEQ ID NO: 11.

25. The isolated polynucleotide of claim 23, wherein said polynucleotide sequence comprises nucleotides 209–1288 of SEQ ID NO: 13.

* * * * *